United States Patent [19]

Lunkenheimer et al.

[11] Patent Number: 5,482,956

[45] Date of Patent: Jan. 9, 1996

[54] METHOD OF TREATING PARASTIC PROTOZOA WITH SUBSTITUTED BENZIMIDAZOLES

[75] Inventors: Winfried Lunkenheimer, Wuppertal; Bernd Baasner, Bergisch Gladbach; Folker Lieb, Leverkusen; Axel Haberkorn, Wuppertal, all of Germany

[73] Assignee: Bayer Aktiengesellschaft, Leverkusen, Germany

[21] Appl. No.: 146,634

[22] Filed: Oct. 29, 1993

[30] Foreign Application Priority Data

Nov. 6, 1992 [DE] Germany .......... 42 37 617.3

[51] Int. Cl.⁶ .................. A61K 31/415
[52] U.S. Cl. .................. 514/394; 514/395
[58] Field of Search .................. 514/394, 395

[56] References Cited

U.S. PATENT DOCUMENTS

| | | | |
|---|---|---|---|
| 3,472,865 | 10/1969 | Newbold et al. | 548/310.4 |
| 3,725,554 | 4/1973 | Burton et al. | 514/394 |
| 3,738,994 | 6/1973 | Fiscer | 548/309.7 |
| 4,536,502 | 8/1985 | Giraudon et al. | 514/234.5 |
| 4,622,323 | 11/1986 | Giraudon et al. | 514/395 |
| 4,859,684 | 8/1989 | Raeymaekers et al. | 514/314 |

FOREIGN PATENT DOCUMENTS

| | | |
|---|---|---|
| 1439128 | 4/1965 | France . |
| 1476531 | 4/1965 | France . |
| 1545816 | 11/1969 | Germany . |
| 2047369 | 9/1970 | Germany . |
| 1670786 | 3/1971 | Germany . |
| 2736448 | 2/1978 | Germany . |
| 1022659 | 6/1964 | United Kingdom . |
| 1286603 | 9/1970 | United Kingdom . |
| 1213796 | 11/1970 | United Kingdom . |
| 1350528 | 4/1972 | United Kingdom . |
| 1505846 | 3/1975 | United Kingdom . |

OTHER PUBLICATIONS

The New Encyclopaedia Britannica, vol. 14, pp. 139–149 (1981).
Degradation of Pesticides, Desiccation and Defoliation, ACh–Receptors as Targets, p. 3 (1982).
Collier's Encyclopedia, vol. 19, pp. 433–435 (1975).
The New Encyclopedia Britannica, vol. 15, p. 130 (1981).
J. Americ. Chem. Soc. 75, 1292–1294, (1953).
Advances in Pharm. and Chemo., 11: 221–293 (1973).
Derwent Abstract, Week 8742, J6 2205–063–A (1976).
Derwent Abstract, Week 8627, J6 1103–873–A (1972).
Journal of Fluorine Chem., 56 (1992) 1–27.
Advances in the Chemistry of Mannich Base, 703–775 (1990).

Primary Examiner—Raymond Henley, III
Assistant Examiner—Kevin E. Weddington
Attorney, Agent, or Firm—Sprung Horn Kramer & Woods

[57] ABSTRACT

The present invention relates to the use of benzimidazoles of the formula (I)

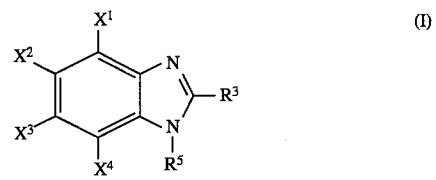

in which
$X^1$, $X^2$, $X_3$, $X^4$, $R^3$ and $R^5$ are described herein and these compounds are agents for combatting parasitic protozoa, in particular coccidia.

19 Claims, No Drawings

METHOD OF TREATING PARASITIC PROTOZOA WITH SUBSTITUTED BENZIMIDAZOLES

The present invention relates to the use of substituted benzimidazoles as agents for combating parasitic protozoa and in particular coccidia, as well as fish parasites and insect parasites.

Substituted benzimidazoles and their use as insecticides, fungicides and herbicides have already been disclosed (EP-OS (European Published Specification) 87 375 and 152 360, U.S. Pat. Nos. 3,472,865 and 3,576,818, 3,418,318 and EP-OS (European Published Specification) 260 744, 266 984, 181 826 and 239 508).

Polyhalogenated benzimidazoles and their action as anthelmintics, coccidiostats and pesticides have been disclosed disclosed (DE-OS (German Published Specification) 2 047 369). Nevertheless, their action is not satisfactory in all cases.

The present invention relates to the use of substituted benzimidazoles of the formula (I)

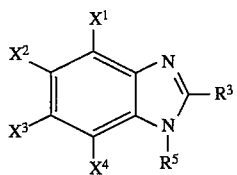

in which
$X^1$, $X^2$, $X^3$ and $X^4$ independently of one another in each case represent hydrogen, halogen, cyano or nitro, or represent in each case optionally substituted alkyl, alkoxy, alkylthio, alkylsulphinyl, alkylsulphonyl or cycloalkyl, or represent optionally substituted, fused dioxyalkylene, or represent hydroxycarbonyl, alkylcarbonyl, alkoxycarbonyl or cycloalkyloxycarbonyl, or represent in each case optionally substituted amino or aminocarbonyl, or represent in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but wherein at least one of the substituents $X^1$, $X^2$, $X^3$ and $X^4$ is other than hydrogen and halogen, $R^3$ represents fluoroalkyl and $R^5$ represents alkyl which is mono- or polysubstituted by identical or different substituents from the group comprising OH, CN, $NH_2$, cycloalkyl, alkenyl, alkinyl, alkoxy, halogenoalkoxy, alkylthio, halogenoalkylthio, alkenoxy, alkinoxy, aminocarbonyl, optionally substituted alkoxycarbonyl (alkO-CO-), optionally substituted alkoxycarbonyloxy (alkO-COO-), optionally substituted (het-)aryl, optionally substituted (het-)aryloxy, optionally substituted (het-)arylthio, optionally substituted (het-)arylsulphonyl, dialkoxyphosphonyl

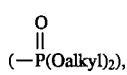

optionally substituted alkylcarbonyl (-CO-alkyl), optionally substituted (het-)arylcarbonyl (-CO-aryl), optionally substituted (het-)aryloxycarbonyl (arylO-CO-), optionally substituted (het-)arylcarbonyloxy (arylCOO-), aminosulphonyl (—$SO_2NH_2$), optionally substituted mono- or dialkylaminosulphonyl, acylated amino or monoalkylamino or optionally substituted dialkylamino, or $R^5$ furthermore represents optionally substituted alkoxycarbonyl, optionally substituted (het-)aryloxycarbonyl, (het-)arylsulphonyl, (het-)arylaminocarbonylaminocarbonyloxy (arylNH—CO—NH—COO—) or —$SO_2$—$NR^1R^2$, wherein $R^1$ and $R^2$ represents H or alkyl which is optionally substituted by one or more of the radicals mentioned above for $R^5$, as agents for combating parasitic protozoa and in particular coccidia.

The substituted benzimidazoles of the formula (I) are known in some cases and can be prepared by processes which are known per se.

The substituted benzimidazoles of the formula (I) are new in some cases and are the subject-matter of several patent applications which have been simultaneously submitted by the Applicant Company.

Formula (I) provides a general definition of the substituted benzimidazoles which can be used according to the invention. Preferred compounds of the formula (I) are those in which $X^1$, $X^2$, $X^3$ and $X^4$ independently of one another in each case represent hydrogen, fluorine, chlorine, bromine, iodine, cyano or nitro, or represent in each case straight-chain or branched alkyl, alkoxy, alkylthio, alkylsulphinyl or alkylsulphonyl having in each case 1 to 8 carbon atoms, or represent cycloalkyl having 3 to 8 carbon atoms, or represent in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, or represent divalent dioxyalkylene which has 1 to 5 carbon atoms and is optionally mono- or polysubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or furthermore represent hydroxycarbonyl, or represent in each case straight-chain or branched alkylcarbonyl or alkoxycarbonyl having in each case 1 to 6 carbon atoms in the alkyl part, or represent cycloalkyloxycarbonyl having 3 to 8 carbon atoms in the cycloalkyl part, or represent amino or aminocarbonyl, in each case optionally mono- or polysubstituted by identical or different substituents, possible substituents on the amino in each case being:

in each case straight-chain or branched alkyl having 1 to 6 carbon atoms, halogenoalkyl having 1 to 6 carbon atoms and 1 to 13 halogen atoms, alkoxyalkyl or alkylcarbonyl having in each case 1 to 6 carbon atoms in the individual alkyl parts, or arylcarbonyl, arylsulphonyl, arylaminocarbonyl or arylmethylsulphonyl having in each case 6 to 10 carbon atoms in the aryl part and in each case optionally mono- or polysubstituted in the aryl part by identical or different substituents, possible substituents on the aryl in each case being those mentioned for $R^1$;

or furthermore represent aryl, aryloxy, arylthio, arylsulphinyl, arylsulphonyl, arylsulphonyloxy, arylcarbonyl, aryloxycarbonyl, arylthiomethylsulphonyl or arylazo having in each case 6 to 10 carbon atoms in the aryl part and in each case optionally mono- or polysubstituted in the aryl part by identical or different substituents, possible possible substituents on the aryl in each case being those mentioned for $R^1$, but wherein at least one of the substituents $X^1$, $X^2$, $X^3$ and $X^4$ is other than hydrogen and halogen.

$R^3$ represents 1–15 fluoro-$C_1$–$C_7$-alkyl and $R^5$ represents $C_{1-14}$-alkyl which is mono- or polysubstituted by identical or different substituents from the group comprising OH, CN, $NH_2$, $C_5$–$C_{10}$-cycloalkyl, $C_2$–$C_6$-alkenyl, $C_1$–$C_6$-alkinyl, $C_{1-6}$-alkoxy, 1–5-halogeno-$C_{1-6}$-alkoxy, $C_{1-6}$-alkylthio, 1–5-halogeno-$C_{1-6}$-alkylthio, $C_{2-6}$-alkenoxy, $C_{3-6}$-alkinoxy, optionally substituted $C_{1-6}$-alkoxycarbonyl, alkoxycarbonyloxy and optionally substituted radicals from the group comprising phenyl, pyridyl, phenoxy, phenylthio, phenylsulphonyl, phenylazo, di($C_{1-4}$-alkoxy)phosphonyl

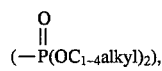
$(-P(OC_{1-4}alkyl)_2)$, $C_{1-6}$-alkylcarbonyl, benzoyl, aminocarbonyl

$(NH_2C-)$, aminosulphonyl ($NH_2SO_2$—), mono- or di($C_{1-6}$alkyl)-aminosulphonyl, acylated amino or acylated mono-($C_{1-6}$-alkyl)amino, phenoxycarbonyl, phenoxycarbonyloxy and di($C_{1-6}$)alkylamino, or $R^5$ furthermore represents the radicals of optionally substituted $C_{1-6}$-alkoxycarbonyl, phenylsulphonyl, optionally substituted phenoxycarbonyl, phenylaminocarbonylaminocarbonyloxy or —$SO_2$—$NR^1R^2$, wherein $R^1$ and $R^2$ represents hydrogen or $C_{1-4}$-alkyl which is optionally substituted by one of the radicals mentioned above for $R^5$.

The following substituents may be mentioned as substituents of the optionally substituted radicals: halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxyalkyl, alkoxyalkoxy, alkanoyl, alkoxycarbonyl or alkoximinoalkyl having in each case 1 to 4 carbon atoms in the individual alkyl parts, divalent dioxyalkylene having 1 to 4 carbon atoms and optionally mono- to hexa-substituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or phenyl which is optionally mono- to pentasubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms.

Acyl radicals which may be mentioned for the acylated radicals listed are the radicals $C_{1-6}$-alkoxycarbonyl, $C_{1-6}$-alkylcarbonyl, $C_{1-6}$-alkoxycarbonyloxy, $C_{1-6}$-alkylsulpho-nyl, benzoyl, which is optionally substituted by one of the abovementioned radicals, and $C_{1-6}$-alkenylcarbonyl.

The substituents in compounds of the formula (I) particularly preferably have the following meanings:

$R^3$ represents $C_{1-7}$-alkyl, in particular methyl or ethyl, which is halogenated by fluorine, $X^1$ and $X^4$ represent identical or different radicals from the group comprising H, $C_{1-4}$-alkyl, in particular methyl or ethyl, which is optionally perhalogenated by fluorine or chlorine, in particular trifluoromethyl, halogen, in particular chlorine or bromine, $C_{1-4}$-alkoxy, in particular methoxy, amino, acetylamino and —$COOR^6$;

$R^6$ represents $C_{1-4}$-alkyl, in particular methyl or ethyl, or cycloalkyl having up to 6 C atoms, in particular cyclohexyl; and one of the radicals $X^2$ or $X^3$ represents a radical from the group comprising CN, OH, COOH, $NO_2$, $NH_2$, optionally substituted radicals from the group comprising $C_{1-4}$-alkyl, in particular methyl, ethyl, propyl or t-butyl, cycloalkyl having up to 6 C atoms, in particular cyclohexyl, $C_{1-4}$-alkoxy, in particular methoxy or ethoxy, $C_{1-4}$-alkylthio, $C_{1-4}$-alkylsulphonyl, in particular methylsulphonyl, $C_{1-4}$-alkylsulphonyloxy, $C_{1-4}$-alkylcarbonyl, in particular acetyl, $C_{1-13}$-alkoxycarbonyl, cycloalkoxycarbonyl having up to 6 C atoms in the cycloalkyl part, in particular cyclohexyloxycarbonyl, phenoxy, phenylthio, phenylsulphonyl, phenylsulphonyloxy, benzoyl, phenoxycarbonyl, amino, which is acylated by benzoyl, phenylsulphonyl or phenylaminocarbonyl, which are in turn optionally substituted, of the radicals $C_{1-4}$-alkyl-O—CO—N($C_{1-4}$-alkyl)—$SO_2$—, di($C_{1-4}$-alkyl)-amino, aminocarbonyl

$(NH_2C-)$, or represents the radical phenyl-N=N—, and the other radical $X^2$ or $X^3$ represents hydrogen or halogen, in particular fluorine or chlorine.

Substituents of the optionally substituted radical which may be mentioned are halogen, in particular fluorine and chlorine, OH, $NH_2$, $NO_2$, CN, COOH, $C_{1-4}$-alkoxycarbonyl, in particular methoxycarbonyl, $C_{1-4}$-alkylcarbonyl, in particular acetyl, benzoyl, which is in turn optionally substituted by one of the radicals mentioned here, $C_{1-4}$-alkyl, in particular methyl or ethyl, $C_{1-4}$-alkoxy, in particular methoxy or ethoxy, $C_{1-4}$-alkylthio, in particular methylmercapto, trifluoromethyl, pentafluoroethyl, fluorochloroethyl, trichloroethyl, trifluoromethoxy, trichloromethoxy, trifluoromethylmercapto, methoxyethoxy, ethoxyethoxy, hydroxyethoxy, ethoxyethyl, methoxyethyl, hydroxyethyl, methylamino, ethylamino, dimethylamino, diethylamino, di(trifluoromethyl)-amino, phenyl and phenoxy, which can in turn carry one of the abovementioned radicals.

The radicals $X^2$ and $X^3$, together with the adjacent C atoms, can represent a dioxolanyl or dioxanyl ring which can be substituted by halogen, such as fluorine or chlorine, or $C_{1-4}$-halogenoalkyl, such as trifluoromethyl or trifluoroethyl, or represent optionally substituted phenyl or represent rings of the formulae

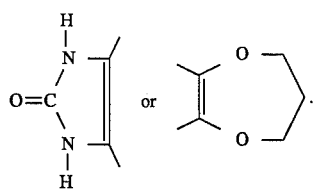

R⁵ represents methyl or ethyl, which is substituted by OH, CN, $C_{1-4}$-alkoxy, such as methoxy, ethoxy, propoxy or t-butoxy, $C_{1-4}$-halogenoalkoxy, such as trifluoromethoxy, pentafluoroethoxy or fluoropropoxy, $C_{2-4}$-alkoxycarbonyl, such as methoxycarbonyl, ethoxycarbonyl, propoxycarbonyl or t-butoxycarbonyl, phenyl, benzoyl, benzylcarbonyl or pyridyl which is optionally substituted by halogen, such as fluorine, chlorine, bromine, $NO_2$ or $C_{1-4}$-alkyl, such as methyl, or a radical of the formula

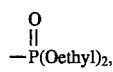

or represents aminosulphonyl, mono- or di($C_{1-4}$-alkyl)aminosulphonyl, mono- or di($C_{1-4}$-halogenoalkyl)aminosulphonyl, aminocarbonyl, amino or mono-($C_{1-4}$-alkyl)amino, which can be acylated by $C_{1-4}$-alkoxycarbonyl, such as ethoxycarbonyl or methoxycarbonyl, acetyl, $C_{2-4}$-alkenylcarbonyl or di($C_{1-4}$-alkyl)amino;

or R⁵ furthermore represents the radicals aminosulphonyl ($NH_2SO_2$-), mono- or di($C_{1-4}$-alkylamino)sulphonyl, which are optionally substituted by halogen, such as fluorine or chlorine, $C_{1-4}$-alkoxycarbonyl, such as ethoxycarbonyl or methoxycarbonyl, or phenylsulphonyl which is optionally substituted by one of the radicals mentioned earlier above.

Especially preferred compounds of the formula (I) are those in which the radicals have the following meanings:

R³ represents 1-7-halogeno-$C_{1-4}$-alkyl, in particular pentafluoroethyl, trifluoromethyl, fluoro-ethyl or difluoroethyl, and especially trifluoromethyl.

X¹ and X⁴ represent hydrogen, halogen, in particular chlorine or bromine, $C_{1-4}$-alkyl, in particular methyl, 1-7-halogeno-$C_{1-4}$-alkyl, in particular trifluoromethyl, $C_{1-4}$alkoxy, in particular methoxy, or $NH_2$ which is optionally substituted by acetyl;

one of the radicals X² or X³ represents a radical from the group comprising 1-7-halogeno-$C_{1-4}$-alkyl, in particular trifluoromethyl, phenyl, $C_{1-6}$-alkyl, cycloalkyl having up to 6 C atoms, in particular cyclohexyl, $NO_2$ and a radical of the formula

—A—B wherein A represents a divalent radical of the formula
—O—, —S—, —O—$SO_2$—(B), —$SO_2$—(B),

—NH—(B),

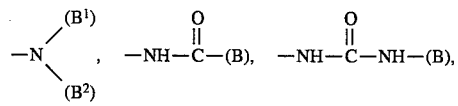

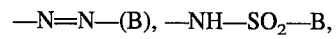

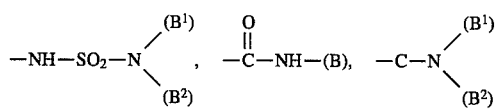

and

B (or B¹ and B₂) represents hydrogen or $C_{1-6}$-alkyl which is optionally substituted by halogen, in particular chlorine or bromine, $C_{1-4}$-alkoxy, $C_{1-4}$-alkylthio, aryloxy, in particular phenoxy, arylthio, in particular phenylthio, or aryl, in particular phenyl, wherein the aryl radicals in turn are optionally substituted by halogen, in particular chlorine or bromine, $C_{1-4}$-alkyl or 1-7 -halogeno-$C_{1-4}$-alkyl, in particular trifluoromethyl; or B furthermore represents aryl, in particular phenyl, which is optionally substituted by $C_{1-4}$-alkyl, halogen, in particular chlorine, $C_{1-4}$ -alkoxy-$C_{1-4}$-alkyl, $C_{1-4}$-alkoxy-$C_{1-4}$-alkoxy, $NO_2$, carbonyl-$C_{1-4}$-alkoxy (-COOalk), 1-7-halogeno-$C_{1-4}$-alkyl, in particular trifluoromethyl, or halogen-substituted or halogenoalkyl-substituted dioxanyl or dioxolanyl, or B furthermore represents cycloalkyl having up to 6 C atoms, in particular cyclohexyl, or represents $C_{1-4}$-alkoxycarbonyl, in particular methoxycarbonyl; and the other radical X² or X³ represents hydrogen or halogen, in particular chlorine or bromine.

The radicals X² or X³, together with the adjacent C atoms, can represent rings of the following formulae:

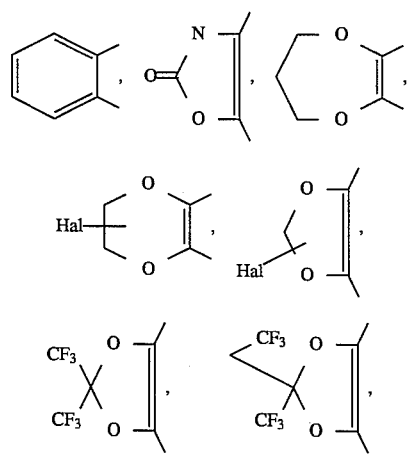

Hal represents fluorine or chlorine and

R⁵ represents the preferred or particularly preferred radicals mentioned earlier above.

Compounds which can be used according to the invention are the following new substituted benzimidazoles of the general formula (Ia)

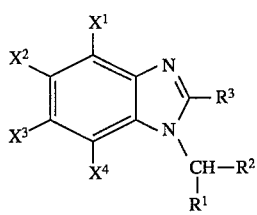

(Ia)

in which
R¹ represents hydrogen, alkyl or alkoxy, or represents optionally substituted aryl, R² represents hydroxyl or cyano, or represents in each case optionally substituted alkyl, alkenyl, alkinyl, alkoxy, alkenyloxy, alkinyloxy, alkylthio, amino, aminocarbonyl, alkylcarbonyl, alkoxycarbonyl, alkylcarbonyloxy, dialkoxyphosphonyl, (hetero)aryl, (hetero)arylcarbonyl, (hetero)aryloxycarbonyl, (hetero)arylcarbonyloxy or (hetero)arylaminocarbonylaminocarbonyloxy and R³ represents fluoroalkyl and X¹, X², X³ and X⁴ independently of one another in each case represent hydrogen, halogen, cyano or nitro, or represent in each case optionally substituted alkyl, alkoxy, alkylthio, alkylsulphinyl, alkylsulphonyl or cycloalkyl, or represent optionally substituted, fused dioxyalkylene, or represent hydroxycarbonyl, alkylcarbonyl, alkoxycarbonyl or cycloalkyloxycarbonyl, or represent in each case optionally substituted amino or aminocarbonyl, or represent in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but wherein at least one of the substituents X¹, X², X³ or X⁴ represents halogenoalkyl, with the exception of the chloromethyl radical, halogenoalkoxy, halogenoalkylthio, halogenoalkylsulphinyl, halogenoalkylsulphonyl or alkylsulphonyl, or represents optionally substituted, fused dioxyalkylene, or represents hydroxycarbonyl, alkylcarbonyl, alkoxycarbonyl or cycloalkyloxycarbonyl, or represents in each case optionally substituted amino or aminocarbonyl, or represents in each case optionally substituted aryl, arylthio, arylsulphinyl, arylsulphonyl, arylsulphonyloxy, arylcarbonyl, aryloxycarbonyl, arylazo or arylthiomethylsulphonyl.

Where appropriate, depending on the nature and number of substituents, the compounds of the formula (Ia) can exist as geometric and/or optical isomers or regioisomers or isomer mixtures thereof with variant compositions.

The new substituted benzimidazoles of the general formula (Ia) are obtained by a process in which a) 1H-benzimidazoles of the formula (IIa)

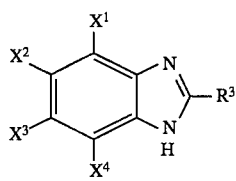

(IIa)

in which
R³, X¹, X², X³ and X⁴ have the abovementioned meaning, are reacted with compounds of the formula (IIIa)

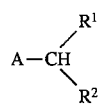

(IIIa)

in which
A represents a suitable leaving group,
R¹ has the abovementioned meaning and
R² has the abovementioned meaning, if appropriate in the presence of a diluent and if appropriate in the presence of a reaction auxiliary.

Preferred compounds of the formula (Ia) are those in which

R¹ represents hydrogen, or represents in each case straight-chain or branched alkyl or alkoxy having in each case 1 to 8 carbon atoms, or represents phenyl which is optionally mono- or polysubstituted by identical or different substituents, possible substituents being:

halogen, cyano, nitro, in each case straight-chain or branched alkyl, alkoxy, alkylthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched alkoxyalkyl, alkoxyalkoxy, alkanoyl, alkoxycarbonyl or alkoximinoalkyl having in each case 1 to 6 carbon atoms in the individual alkyl parts, divalent dioxyalkylene having 1 to 5 carbon atoms, which is optionally mono-or polysubstituted by identical or different substituents from the group comprising halogen and/or straight-chain or branched alkyl having 1 to 6 carbon atoms and/or straight-chain or branched halogenoalkyl having 1 to 6 carbon atoms and 1 to 13 identical or different halogen atoms, or phenyl which is optionally mono- or polysubstituted by identical or different substituents from the group comprising halogen and/or straight-chain or branched alkyl having 1 to 6 carbon atoms and/or straight-chain or branched halogenoalkyl having 1 to 6 carbon atoms and 1 to 13 identical or different halogen atoms, R² represents hydroxyl or cyano, or represents alkyl, alkenyl, alkinyl, alkoxy, alkenyloxy, alkinyloxy, alkylthio, alkylcarbonyl, alkoxycarbonyl, alkylcarbonyloxy or dialkoxyphosphonyl having in each case up to 8 carbon atoms in the individual alkyl or alkenyl or alkinyl parts and in each case optionally mono- or polysubstituted by identical or different substituents, possible substituents in each case being: halogen or straight-chain or branched alkoxy having 1 to 8 carbon atoms, or aryl having 6 to 10 carbon atoms or heteroaryl having 2 to 9 carbon atoms and 1 to 5 hetero atoms—in particular nitrogen, oxygen and/or sulphur—which are in each case optionally mono- or polysubstituted by identical or different substituents, possible substituents on the aryl or heteroaryl being those mentioned for R¹, R² furthermore represents amino or aminocarbonyl, in each case optionally mono- or disubstituted by identical or different substituents, possible substituents in each case being:

formyl, straight-chain or branched alkyl having 1 to 8 carbon atoms, straight-chain or branched alkenyl having 2 to 8 carbon atoms or straight-chain or branched alkylsulphonyl having 1 to 8 carbon atoms, carbamoyl, thiocarbamoyl or sulphamoyl, in each case optionally mono- or disubstituted by identical or different straight-chain or branched alkyl radicals having 1 to 8 carbon atoms, cycloalkyl, cycloalkylcarbonyl or cycloalkyloxycarbonyl having in each case 3 to 8 carbon atoms in the cycloalkyl part, alkylcarbonyl, alkenylcarbonyl, alkoxycarbonyl, alkenyloxycarbonyl, alkylthio-carbonyl, alkoxythiocarbonyl or alkylthio-thiocarbonyl having in each case 1 to 8 carbon atoms in the individual straight-chain or branched alkyl parts, in each case divalent and cyclic alkanediylcarbonyl or alkanediyloxycarbonyl having in each case 2 to 6 carbon atoms in the alkanediyl part, arylalkyl, arylalkylcarbonyl or arylalkyloxycarbonyl having in each case 6 to 10 carbon atoms in the aryl part and 1 to 8 carbon atoms in the straight-chain or branched alkyl part and in each case optionally mono- or polysubstituted in the aryl part by identical or different substituents, or aryl, arylcarbonyl or aryloxycarbonyl having in each case 6 to 10 carbon atoms in the aryl part and in each case optionally mono- or polysubstituted in the aryl part by identical or different substituents, possible substituents on the aryl in each case being those mentioned for $R^1$, or $R^2$ furthermore represents aryl, arylcarbonyl, aryloxycarbonyl, arylcarbonyloxy or arylaminocarbonylaminocarbonyloxy having in each case 6 to 10 carbon atoms in the aryl part and in each case optionally monoor polysubstituted by identical or different substituents, possible substituents on the aryl in each case being those mentioned for $R^1$, or $R^2$ furthermore represents heteroaryl, heteroarylcarbonyl, heteroaryloxycarbonyl, heteroarylcarbonyloxy or heteroarylaminocarbonylaminocarbonyloxy having in each case 2 to 9 carbon atoms and 1 to 5 identical or different hetero atoms—in particular nitrogen, oxygen and/or sulphur—in the heteroaryl part and in each case optionally mono- or polysubstituted by identical or different substituents, possible substituents on the heteroaryl in each case being the substituents on the aryl mentioned for $R^1$, and $R^3$ represents perfluoroalkyl or partly fluorinated alkyl having 1 to 25 C atoms and up to 50 F atoms and $X^1$, $X^2$, $X^3$ and $X^4$ independently of one another in each case represent hydrogen, fluorine, chlorine, bromine, iodine, cyano or nitro, or represent in each case straight-chain or branched alkyl, alkoxy, alkylthio, alkylsulphinyl or alkylsulphonyl having in each case 1 to 8 carbon atoms, or represent cycloalkyl having 3 to 8 carbon atoms, or represent in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, or represent divalent dioxyalkylene having 1 to 5 carbon atoms, which is optionally mono- or polysubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or furthermore represent hydroxycarbonyl, or represent in each case straight-chain or branched alkylcarbonyl or alkoxycarbonyl having in each case 1 to 6 carbon atoms in the alkyl part, or represent cycloalkyloxycarbonyl having 3 to 8 carbon atoms in the cycloalkyl part, or represent amino or aminocarbonyl, in each case optionally mono- or polysubstituted by identical or different substituents, possible substituents on the amino in each case being:

in each case straight-chain or branched alkyl having 1 to 6 carbon atoms, halogenoalkyl having 1 to 6 carbon atoms and 1 to 13 halogen atoms, alkoxyalkyl or alkylcarbonyl having in each case 1 to 6 carbon atoms in the individual alkyl parts, or arylcarbonyl, arylsulphonyl, arylaminocarbonyl or arylmethylsulphonyl having in each case 6 to 10 carbon atoms in the aryl part and in each case optionally mono- or polysubstituted in the aryl part by identical or different substituents, possible substituents on the aryl in each case being those mentioned for $R^1$, or furthermore represent aryl, aryloxy, arylthio, arylsulphinyl, arylsulphonyl, arylsulphonyloxy, arylcarbonyl, aryloxycarbonyl, arylthiomethylsulphonyl or arylazo having in each case 6 to 10 carbon atoms in the aryl part and in each case optionally monoor polysubstituted in the aryl part by identical or different substituents, possible possible substituents on the aryl in each case being those mentioned for $R^1$, and wherein at least one of the substituents $X^1$, $X^2$, $X^3$ or $X^4$ represents in each case straight-chain or branched halogenoalkyl (with the exception of the chloromethyl radical), halogenoalkoxy, halogenoalkylthio, halogeno-alkylsulphinyl or halogenoalkylsulphonyl having in each case 1 to 6 carbon atoms and 1 to 13 identical or different halogen atoms, or represents straight-chain or branched alkylsulphonyl having 1 to 6 carbon atoms, or represents divalent dioxyalkylene having 1 to 5 carbon atoms, which is optionally mono- or polysubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or furthermore represents hydroxycarbonyl, or represents in each case straight-chain or branched alkylcarbonyl or alkoxycarbonyl having in each case 1 to 6 carbon atoms in the alkyl part, or represents cycloalkyloxycarbonyl having 3 to 8 carbon atoms in the cycloalkyl part, or represents amino or aminocarbonyl, in each case optionally mono- or polysubstituted by identical or different substituents, possible substituents on the amino in each case being:

in each case straight-chain or branched alkyl having 1 to 6 carbon atoms, halogenoalkyl having 1 to 6 carbon atoms and 1 to 13 halogen atoms, alkoxyalkyl or alkylcarbonyl having in each case 1 to 6 carbon atoms in the individual alkyl parts, or arylcarbonyl, arylsulphonyl, arylaminocarbonyl or arylmethylsulphonyl having in each case 6 to 10 carbon atoms in the aryl part and in each case optionally mono- or polysubstituted in the aryl part by identical or different substituents, possible substituents on the aryl in each case being those mentioned for $R^1$; or furthermore represents aryl, arylthio, arylsulphinyl, arylsulphonyl, arylsulphonyloxy, arylcarbonyl, aryloxycarbonyl, arylthiomethylsulphonyl or arylazo having in each case 6 to 10 carbon atoms in the aryl part and in each case optionally mono- or polysubstituted in the aryl part by identical or different substituents, possible possible substituents on the aryl in each case being those mentioned for $R^1$.

Particularly preferred compounds of the formula (Ia) are those in which $R^1$ represents hydrogen, or represents in each case straight-chain or branched alkyl or alkoxy having in each case 1 to 6 carbon atoms, or represents phenyl which is optionally mono- to trisubstituted by identical or different substituents, possible substituents being:

halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxyalkyl, alkoxyalkoxy, alkanoyl, alkoxycarbonyl or alkoximinoalkyl having in each case 1 to 4 carbon atoms in the individual alkyl parts, divalent dioxyalkylene having 1 to 4 carbon atoms, which is optionally mono- to hexasubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or phenyl which is optionally mono- to pentasubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, $R^2$ represents hydroxyl or cyano, or represents alkyl, alkenyl, alkinyl, alkoxy, alkenyloxy, alkinyloxy, alkylthio, alkylcarbonyl, alkoxycarbonyl, alkylcarbonyloxy or dialkoxyphosphonyl having in each case up to 6 carbon atoms in the individual alkyl or alkenyl or alkinyl parts and in each case optionally mono- to pentasubstituted by identical or different halogen substituents, or represents alkyl, alkenyl, alkinyl, alkoxy, alkenyloxy, alkinyloxy, alkylthio, alkylcarbonyl, alkoxycarbonyl, alkylcarbonyloxy or dialkoxyphosphonyl having in each case up to 6 carbon atoms in the individual alkyl or alkenyl or alkinyl parts and in each case optionally mono- to trisubstituted by identical or different substituents, possible substituents in each case being:

straight-chain or branched alkoxy having 1 to 6 carbon atoms, or aryl having 6 or 10 carbon atoms or heteroaryl having 2 to 9 carbon atoms and 1 to 4 hetero atoms—in particular nitrogen, oxygen and/or sulphur—which are in each case optionally mono- to trisubstituted by identical or different substituents, possible substituents on the aryl or heteroaryl being those mentioned for $R^1$, or $R^2$ furthermore represents amino or aminocarbonyl, in each case optionally mono- or disubstituted by identical or different substituents, possible substituents in each case being:

formyl, straight-chain or branched alkyl having 1 to 6 carbon atoms, straight-chain or branched alkenyl having 2 to 6 carbon atoms or straight-chain or branched alkylsulphonyl having 1 to 6 carbon atoms, carbamoyl, thiocarbamoyl or sulphamoyl, in each case optionally mono- or disubstituted by identical or different straight-chain or branched alkyl radicals having 1 to 6 carbon atoms, cycloalkyl, cycloalkylcarbonyl or cycloalkyloxycarbonyl having in each case 3 to 7 carbon atoms in the cycloalkyl part, alkylcarbonyl, alkenylcarbonyl, alkoxycarbonyl, alkenyloxycarbonyl, alkylthio-carbonyl, alkoxythiocarbonyl or alkylthio-thiocarbonyl having in each case 1 to 6 carbon atoms in the individual straight-chain or branched alkyl parts, in each case divalent and cyclic alkanediylcarbonyl or alkanediyloxycarbonyl having in each case 2 to 5 carbon atoms in the alkanediyl part, arylalkyl, arylalkylcarbonyl or arylalkyloxycarbonyl having in each case 6 or 10 carbon atoms in the aryl part and 1 to 6 carbon atoms in the straight-chain or branched alkyl part and in each case optionally mono- to trisubstituted in the aryl part by identical or different substituents, or aryl, arylcarbonyl or aryloxycarbonyl having in each case 6 or 10 carbon atoms in the aryl part and in each case optionally mono- to trisubstituted in the aryl part by identical or different substituents, possible substituents on the aryl in each case being those mentioned for $R^1$, or $R^2$ furthermore represents aryl, arylcarbonyl, aryloxycarbonyl, arylcarbonyloxy or arylaminocarbonylaminocarbonyloxy having in each case 6 or 10 carbon atoms in the aryl part and in each case optionally monoto pentasubstituted by identical or different substituents, possible substituents on the aryl in each case being those mentioned for $R^1$, or $R^2$ furthermore represents heteroaryl, heteroarylcarbonyl, heteroaryloxycarbonyl, heteroarylcarbonyloxy or heteroarylaminocarbonylaminocarbonyloxy having in each case 2 to 9 carbon atoms and 1 to 4 identical or different hetero atoms—in particular nitrogen, oxygen and/or sulphur—in the heteroaryl part and in each case optionally mono- to pentasubstituted by identical or different substituents, possible substituents on the heteroaryl in each case being the substituents on the aryl mentioned for $R^1$, and $R^3$ represents $CF_3$, $C_2F_5$ or $C_7F_{15}$ and $X^1$, $X^2$, $X^3$ and $X^4$ independently of one another in each case represent hydrogen, fluorine, chlorine, bromine, cyano or nitro, or represent in each case straight-chain or branched alkyl, alkoxy, alkylthio, alkylsulphinyl or alkylsulphonyl having in each case 1 to 6 carbon atoms, or represent cycloalkyl having 3 to 7 carbon atoms, or represent in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, or represent divalent dioxyalkylene having 1 to 4 carbon atoms, which is optionally mono- to hexasubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or furthermore represent hydroxycarbonyl, or represent in each case straight-chain or branched alkylcarbonyl or alkoxycarbonyl having in each case 1 to 4 carbon atoms in the alkyl part, or represent cycloalkyloxycarbonyl having 3 to 7 carbon atoms in the cycloalkyl part, or represent amino or aminocarbonyl, in each case optionally mono- or disubstituted by identical or different substituents, possible substituents on the amino in each case being:

in each case straight-chain or branched alkyl having 1 to 4 carbon atoms, halogenoalkyl having 1 to 4 carbon atoms and 1 to 9 halogen atoms, alkoxyalkyl or alkylcarbonyl having in each case 1 to 4 carbon atoms in the individual alkyl parts, or arylcarbonyl, arylsulphonyl, arylaminocarbonyl or arylmethylsulphonyl having in each case 6 or 10 carbon atoms in the aryl part and in each case optionally mono- to pentasubstituted in the aryl part by identical or different substituents, possible substituents on the aryl in each case being those mentioned for $R^1$; or furthermore represent aryl, aryloxy, arylthio, arylsulphinyl, arylsulphonyl, arylsulphonyloxy, arylcarbonyl, aryloxycarbonyl, arylthiomethylsulphonyl or arylazo having in each case 6 or 10 carbon atoms in the aryl part and in each case optionally monoto pentasubstituted in the aryl part by identical or different substituents, possible possible substituents on the aryl in each case being those mentioned for $R^1$, and wherein at least one of the substituents $X^1$, $X^2$, $X^3$ or $X^4$ represents in each case straight-chain or branched halogenoalkyl (with the exception of the chloromethyl radical), halogenoalkoxy, halogenoalkylthio, halogenoalkylsulphinyl or halogenoalkylsulphonyl having in each case 1 to 4 carbon atoms and 1 to 9 identical or different halogen atoms, or represents straight-chain or branched alkylsulphonyl having 1 to 4 carbon atoms, or represents divalent dioxyalkylene having 1 to 4 carbon atoms, which is optionally mono- to hexasubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or furthermore represents hydroxycarbonyl, or represents in each case straight-chain or branched alkylcarbonyl or alkoxycarbonyl having in each case 1 to 4 carbon atoms in the alkyl part, or represents cycloalkyloxycarbonyl having 3 to 7 carbon atoms in the cycloalkyl part, or represents amino or aminocarbonyl, in each case optionally mono- or disubstituted by identical or different substituents, possible substituents on the amino in each case being:

in each case straight-chain or branched alkyl having 1 to 4 carbon atoms, halogenoalkyl having 1 to 4 carbon atoms and 1 to 9 halogen atoms, alkoxyalkyl or alkylcarbonyl having in each case 1 to 4 carbon atoms in the individual alkyl parts, or arylcarbonyl, arylsulphonyl, arylaminocarbonyl or arylmethylsulphonyl having in each case 6 or 10 carbon atoms in the aryl part and in each case optionally mono- to pentasubstituted in the aryl part by identical or different substituents, possible substituents on the aryl in each case being those mentioned for $R^1$; or furthermore represents aryl, arylthio, arylsulphinyl, arylsulphonyl, arylsulphonyloxy, arylcarbonyl, aryloxycarbonyl, arylthiomethylsulphonyl or arylazo having in each case 6 or 10 carbon atoms in the aryl part and in each case optionally mono- to pentasubstituted in the aryl part by identical or different substituents, possible possible substituents on the aryl in each case being those mentioned for $R^1$.

Aryl radicals which may be mentioned are phenyl, naphthyl, pyridyl, thiophenyl, inranyl, pyrrolyl and piperidinyl.

Phenyl, naphthyl, pyridyl, thiophenyl, euranyl, pyrrolyl, piperidinyl are mentioned as acyl radicals.

Especially preferred compounds of the formula (Ia) are those in which $R^1$ represents hydrogen, or represents in each case straight-chain or branched alkyl or alkoxy having in each case 1 to 4 carbon atoms, or represents phenyl which is optionally mono- or disubstituted by identical or different substituents, possible substituents being:

halogen, cyano, nitro, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxyalkyl, alkoxyalkoxy, alkanoyl, alkoxycarbonyl or alkoximinoalkyl having in each case 1 to 3 carbon atoms in the individual alkyl parts, divalent dioxyalkylene having 1 to 3 carbon atoms, which is optionally mono- to tetrasubstituted by identical or different substituents from the group comprising halogen and/or straight-chain or branched alkyl having 1 to 3 carbon atoms and/or straight-chain or branched halogenoalkyl having 1 to 3 carbon atoms and 1 to 7 identical or different halogen atoms, or phenyl which is optionally mono- to trisubstituted by identical or different substituents from the group comprising halogen and/or straight-chain or branched alkyl having 1 to 3 carbon atoms and/or straight-chain or branched halogenoalkyl having 1 to 3 carbon atoms and 1 to 7 identical or different halogen atoms, $R^2$ represents hydroxyl or cyano, or represents alkyl, alkenyl, alkinyl, alkoxy, alkenyloxy, alkinyloxy, alkylthio, alkylcarbonyl, alkoxycarbonyl, alkylcarbonyloxy or dialkoxyphosphonyl having in each case up to 4 carbon atoms in the individual alkyl or alkenyl or alkinyl parts and in each case optionally mono- to trisubstituted by identical or different halogen atoms— in particular fluorine, chlorine and/or bromine—or represents alkyl, alkenyl, alkinyl, alkoxy, alkenyloxy, alkinyloxy, alkylthio, alkylcarbonyl, alkoxycarbonyl, alkylcarbonyloxy or dialkoxyphosphoryl having in each case up to 4 carbon atoms in the individual alkyl or alkenyl or alkinyl parts and in each case optionally mono- or disubstituted by identical or different substituents, possible substituents in each case being:

straight-chain or branched alkoxy having 1 to 3 carbon atoms, or phenyl which is optionally mono- or disubstituted by identical or different substituents, possible substituents on the phenyl being those mentioned for $R^1$, or $R^2$ furthermore represents amino or aminocarbonyl, in each case optionally mono- or disubstituted by identical or different substituents, possible substituents in each case being:

formyl, straight-chain or branched alkyl having 1 to 4 carbon atoms, straight-chain or branched alkenyl having 2 to 4 carbon atoms or straight-chain or branched alkylsulphonyl having 1 to 4 carbon atoms, carbamoyl, thiocarbamoyl or sulphamoyl, in each case optionally mono- or disubstituted by identical or different straight-chain or branched alkyl radicals having 1 to 4 carbon atoms, cycloalkyl, cycloalkylcarbonyl or cycloalkyloxycarbonyl having in each case 3 to 6 carbon atoms in the cycloalkyl part, alkylcarbonyl, alkenylcarbonyl, alkoxycarbonyl, alkenyloxycarbonyl, alkylthio-carbonyl, alkoxythiocarbonyl or alkylthio-thiocarbonyl having in each case 1 to 4 carbon atoms in the individual straight-chain or branched alkyl parts, in each case divalent and cyclic alkanediylcarbonyl or alkanediyloxycarbonyl having in each case 2 to 4 carbon atoms in the alkanediyl part, phenylalkyl, phenylalkylcarbonyl or phenylalkyloxycarbonyl having in each case 1 to 4 carbon atoms in the straight-chain or branched alkyl part and in each case optionally mono- or disubstituted in the phenyl part by identical or different substituents, or phenyl, phenylcarbonyl or phenyloxycarbonyl, in each case optionally mono- or disubstituted in the phenyl pare by identical or different substituents, possible substituents on the phenyl in each case being those mentioned for $R^1$, or $R^2$ furthermore represents phenyl, phenylcarbonyl, phenyloxycarbonyl, phenylcarbonyloxy or phenylaminocarbonylaminocarbonyloxy, in each case optionally mono- to trisubstituted by identical or different substituents, possible substituents on the phenyl in each case being those mentioned for $R^1$, or $R^2$ furthermore represents heteroaryl, heteroarylcarbonyl, heteroaryloxycarbonyl, heteroarylcarbonyloxy or heteroarylaminocarbonylaminocarbonyloxy having in each case 2 to 9 carbon atoms and 1 to 3 identical or different hetero atoms—in particular nitrogen, oxygen and/or sulphur—in the heteroaryl part and in each case optionally mono- to trisubstituted by identical or different substituents, possible substituents on the heteroaryl in each case being the substituents on the phenyl mentioned for $R^1$. Heteroaryl which may be mentioned is pyridyl, furanyl, thiophenyl, piperidinyl and pyrrolyl, $R^3$ represents $CF_3$ and $X^1$, $X^2$, $X^3$ and $X^4$ independently of one another in each case represent hydrogen, chlorine, bromine, cyano or nitro, or represent in each case straight-chain or branched alkyl, alkoxy, alkylthio, alkylsulphinyl or alkylsulphonyl having in each case 1 to 4 carbon atoms, or represent cycloalkyl having 3, 5 or 6 carbon atoms, or represent in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, or represent divalent dioxyalkylene having 1 to 3 carbon atoms, which is optionally mono- to tetrasubstituted by identical or different substituents from the group comprising halogen and/or straight-chain or branched alkyl having 1 to 3 carbon atoms and/or straight-chain or branched halogenoalkyl having 1 to 3 carbon atoms and 1 to 7 identical or different halogen atoms, or furthermore represent hydroxycarbonyl, or represent in each case straight-chain or branched alkylcarbonyl or alkoxycarbonyl having in each case 1 to 3 carbon atoms in the alkyl part, or represent cycloalkyloxycarbonyl having 3, 5 or 6 carbon atoms in the cycloalkyl part, or represent amino or aminocarbonyl, in each case optionally mono- or disubstituted by identical or different substituents, possible substituents on the amino in each case being:

in each case straight-chain or branched alkyl having 1 to 3 carbon atoms, halogenoalkyl having 1 to 3 carbon atoms and 1 to 7 halogen atoms, alkoxyalkyl or alkylcarbonyl having in each case 1 to 3 carbon atoms in the individual alkyl parts, or phenylcarbonyl, phenylsulphonyl, phenylaminocarbonyl or phenylmethylsulphonyl, in each case optionally monoto trisubstituted in the phenyl part by identical or different substituents, possible substituents on the phenyl in each case being those mentioned for $R^1$; or furthermore for phenyl, phenyloxy, phenylthio, phenylsulphinyl, phenylsulphonyl, phenylsulphonyloxy, phenylcarbonyl, phenyloxycarbonyl, phenylthiomethylsulphonyl or phenylazo, in each case optionally mono- to trisubstituted in the phenyl part by identical or different substituents, possible possible substituents on the phenyl in each case being those mentioned for $R^1$, and wherein at least one of the substituents $X^1$, $X^2$, $X^3$ or $X^4$ represents in each case straight-chain or branched halogenoalkyl (with the exception of the chloromethyl radical), halogenoalkoxy, halogenoalkylthio, halogenoalkylsulphinyl or halogenoalkylsulphonyl having in each case 1 to 3 carbon atoms and 1 to 7 identical or different halogen atoms, or represents straight-chain or branched alkylsulphonyl having 1 to 3 carbon atoms, or represents divalent dioxyalkylene having 1 to 3 carbon atoms, which is optionally mono- to tetrasubstituted by identical or different substituents from the group comprising halogen and/or straight-chain or branched alkyl having 1 to 3 carbon atoms and/or straight-chain or branched halogenoalkyl having 1 to 3 carbon atoms and 1 to 7 identical or different halogen atoms, or furthermore represents hydroxycarbonyl, or represents in each case straight-chain or branched alkylcarbonyl or alkoxycarbonyl having in each case 1 to 3 carbon atoms in the alkyl part, or represents cycloalkyloxycarbonyl having 3, 5 or 6 carbon atoms in the cycloalkyl part, or represents amino or aminocarbonyl, in each case optionally mono- or disubstituted by identical or different substituents, possible substituents on the amino in each case being:

in each case straight-chain or branched alkyl having 1 to 3 carbon atoms, halogenoalkyl having 1 to 3 carbon atoms and 1 to 7 halogen atoms, alkoxyalkyl or alkylcarbonyl having in each case 1 to 3 carbon atoms in the individual alkyl parts, or phenylcarbonyl, phenylsulphonyl, phenylaminocarbonyl or phenylmethylsulphonyl, in each case optionally monoto trisubstituted in the phenyl part by identical or different substituents, possible substituents on the phenyl in each case being those mentioned for $R^1$; or furthermore represents phenyl, phenylthio, phenylsulphinyl, phenylsulphonyl, phenylsulphonyloxy, phenylcarbonyl, phenyloxycarbonyl, phenylthiomethylsulphonyl or phenylazo, in each case optionally mono- to trisubstituted in the phenyl part by identical or different substituents, possible possible substituents on the phenyl in each case being those mentioned for $R^1$.

The following substituted benzimidazoles of the general formula (Ia) may be mentioned specifically:

(Im)

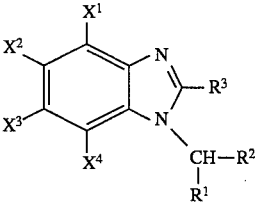

| $X^1$ | $X^2$ | $X^3$ | $X^4$ | $R^1$ | $R^2$ |
|---|---|---|---|---|---|
| Br | H | $Cl-CH_2-SO_2-$ | H | H | $\begin{array}{c} C_2H_5 \\ | \\ N \\ | \\ COOC_2H_5 \end{array}$ |
| Br | H | $C_6H_5-S-CH_2-SO_2-$ | H | H | $\begin{array}{c} C_2H_5 \\ | \\ N \\ | \\ COOC_2H_5 \end{array}$ |
| H | $p\text{-}CH_3-C_6H_4-SO_2-O-$ | $p\text{-}CH_3-C_6H_4-SO_2-O-$ | H | H | $\begin{array}{c} C_2H_5 \\ | \\ N \\ | \\ COOC_2H_5 \end{array}$ |
| Br | H | $C_6H_5-O-CO-$ | H | H | $\begin{array}{c} C_2H_5 \\ | \\ N \\ | \\ COOC_2H_5 \end{array}$ |
| Br | H | 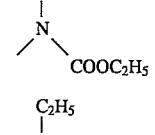 | H | H | $\begin{array}{c} C_2H_5 \\ | \\ N \\ | \\ COOC_2H_5 \end{array}$ |
| Br | H | $n\text{-}C_6H_{13}-O-CO-$ | H | H | $\begin{array}{c} C_2H_5 \\ | \\ N \\ | \\ COOC_2H_5 \end{array}$ |
| Br | H | $C_6H_5-CO-$ | H | H | $\begin{array}{c} C_2H_5 \\ | \\ N \\ | \\ COOC_2H_5 \end{array}$ |
| Br | H | $F_3C-S-$ | H | H | $\begin{array}{c} C_2H_5 \\ | \\ N \\ | \\ COOC_2H_5 \end{array}$ |
| Cl | H | $F_3C-S-$ | H | H | $\begin{array}{c} C_2H_5 \\ | \\ N \\ | \\ COOC_2H_5 \end{array}$ |
| $COO-C_6H_5$ | H | $F_3C-O-$ | H | H | $-O-C_2H_5$ |
| 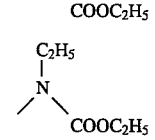 | H | $CF_3$ | H | H | $\begin{array}{c} C_2H_5 \\ | \\ N \\ | \\ COOC_2H_5 \end{array}$ |
| 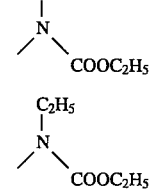 | H | $F_3C-O-$ | H | H | $\begin{array}{c} C_2H_5 \\ | \\ N \\ | \\ COOC_2H_5 \end{array}$ |
| Br | H | $ClFCH-CF_2-S-$ | H | H | $\begin{array}{c} C_2H_5 \\ | \\ N \\ | \\ COOC_2H_5 \end{array}$ |

-continued (Im)

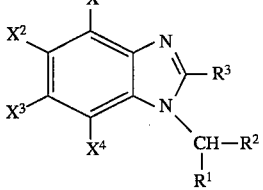

| X¹ | X² | X³ | X⁴ | R¹ | R² |
|---|---|---|---|---|---|
| Br | H | ClFCH—CF$_2$—S— | H | H | —O—C$_2$H$_5$ |
| Br | H | F$_3$C—CHF—CF$_2$—S— | H | H | —N(C$_2$H$_5$)(COOC$_2$H$_5$) |
| Br | H | F$_3$C—CHF—CF$_2$—S— | H | H | —O—C$_2$H$_5$ |
| CF$_3$ | H | CF$_3$ | H | H | —N(C$_2$H$_5$)(COOC$_2$H$_5$) |
| CF$_3$ | H | CF$_3$ | H | H | —O—C$_2$H$_5$ |
| COO-n-C$_3$H$_7$ | H | CF$_3$ | H | H | —N(C$_2$H$_5$)(COOC$_2$H$_5$) |
| COO-i-C$_3$H$_7$ | H | CF$_3$ | H | H | —N(C$_2$H$_5$)(COOC$_2$H$_5$) |
| COO-n-C$_4$H$_9$ | H | CF$_3$ | H | H | —N(C$_2$H$_5$)(COOC$_2$H$_5$) |
| COO-s-C$_4$H$_9$ | H | CF$_3$ | H | H | —N(C$_2$H$_5$)(COOC$_2$H$_5$) |
| COO—C$_6$H$_5$ | H | CF$_3$ | H | H | —N(C$_2$H$_5$)(COOC$_2$H$_5$) |
| COO-s-C$_4$H$_9$ | H | F$_3$C—O— | H | H | —O—C$_2$H$_5$ |
| COO-n-C$_3$H$_7$ | H | CF$_3$ | H | H | —O—C$_2$H$_5$ |
| COO-i-C$_3$H$_7$ | H | CF$_3$ | H | H | —O—C$_2$H$_5$ |
| COO-n-C$_4$H$_9$ | H | CF$_3$ | H | H | —O—C$_2$H$_5$ |
| COO-s-C$_4$H$_9$ | H | CF$_3$ | H | H | —O—C$_2$H$_5$ |
| COO—C$_6$H$_5$ | H | CF$_3$ | H | H | —O—C$_2$H$_5$ |
| COO-n-C$_3$H$_7$ | H | F$_3$C—O— | H | H | —N(C$_2$H$_5$)(COOC$_2$H$_5$) |
| COO-i-C$_3$H$_7$ | H | F$_3$C—O— | H | H | —N(C$_2$H$_5$)(COOC$_2$H$_5$) |
| COO-n-C$_4$H$_9$ | H | F$_3$C—O— | H | H | —N(C$_2$H$_5$)(COOC$_2$H$_5$) |

-continued (Im)

| X¹ | X² | X³ | X⁴ | R¹ | R² |
|---|---|---|---|---|---|
| COO-s-C₄H₉ | H | F₃C—O— | H | H | $\text{C}_2\text{H}_5-\text{N}(-)-\text{COOC}_2\text{H}_5$ |
| COO—C₆H₅ | H | F₃C—O— | H | H | $\text{C}_2\text{H}_5-\text{N}(-)-\text{COOC}_2\text{H}_5$ |
| COO-n-C₃H₇ | H | F₃C—O— | H | H | —O—C₂H₅ |
| COO-i-C₃H₇ | H | F₃C—O— | H | H | —O—C₂H₅ |
| COO-n-C₄H₉ | H | F₃C—O— | H | H | —O—C₂H₅ |

If, for example, 6(6)-phenyl-2-trifluoromethyl-benzimidazole and chloromethyl ethyl ether are used as starting compounds, the course of the reaction of the process for the preparation of the compound Ia can be represented by the following equation:

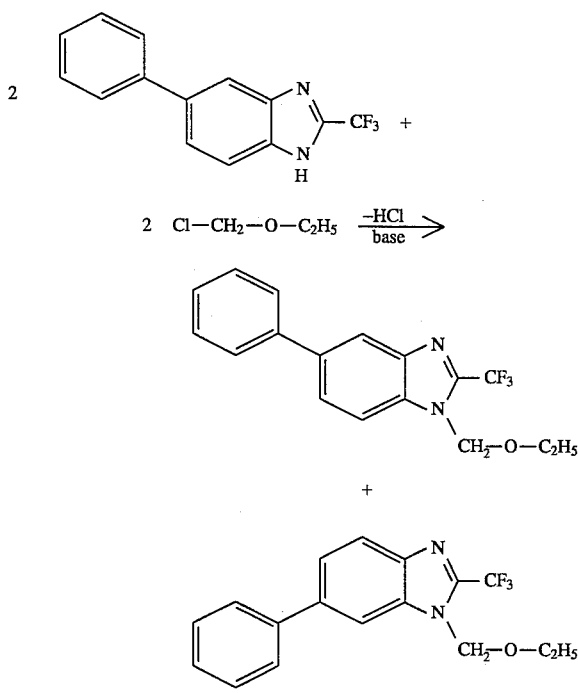

Formula (IIa) provides a general definition of the 1H-benzimidazoles required as starting substances for carrying out the process. In this formula (IIa), X¹, X², X³ and X⁴ preferably represent those radicals which have already been mentioned as preferred for these substituents in connection with the description of the compounds of the formula (Ia). The 1H-benzimidazoles of the formula (IIa) are known or are obtainable by processes analogous to known processes (compare, for example, J.Amer.Chem. Soc. 75, 1292 (1953); and U.S. Pat. No. 3,576,818).

Formula (IIIa) provides a general definition of the compounds furthermore required as starting substances for carrying out the process. In this formula (IIIa), R¹ and R² preferably represent those radicals which have already been mentioned as preferred for these substituents in connection with the description of the substances of the formula (I) according to the invention.

A preferably represents a leaving radical customary in alkylating agents, preferably halogen, in particular chlorine, bromine or iodine, or in each case optionally substituted alkylsulphonyloxy, alkoxysulphonyloxy or arylsulphonyloxy, such as, in particular, methanesulphonyloxy, trifluoromethanesulphonyloxy, methoxysulphonyloxy, ethoxysulphonyloxy or p-toluenesulphonyloxy.

A furthermore also represents an alcohol, alkanoyloxy or alkoxy group, such as, for example, a hydroxyl, acetoxy or methoxy group.

The compounds of the formula (IIIa) are known or are obtainable by processes analogous to known processes (compare, for example, DE 20 40 175; DE 21 19 518; and Synthesis 1973, 703).

Possible diluents for carrying out the process are inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, methylene chloride, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric acid triamide; or esters, such as methyl acetate or ethyl acetate, or bases, such as pyridine, or organic acids, such as formic acid or acetic acid.

The process is preferably carried out in the presence of a suitable reaction auxiliary. Possible reaction auxiliaries are all the customary inorganic or organic bases. These include, for example, alkaline earth metal or alkali metal hydrides, hydroxides, amides, alcoholates, acetates, carbonates or bicarbonates, such as, for example, sodium hydride, sodium amide, lithium diethylamide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, organolithium compounds, such as n-butyllithium, and tertiary amines, such as trimethylamine, triethylamine, tributylamine, diisopropyl-ethylamine, tetramethylguanidine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

In the cases where A in formula (III) represents an alcohol group, alkanoyloxy or an alkoxy group, possible reaction auxiliaries are also organic or inorganic acids, such as, for example, sulphuric acid, hydrochloric acid, p-toluenesulphonic acid, perfluorobutanesulphonic acid or strongly acid ion exchangers.

If appropriate, the process can also be carried out in a two-phase system, such as, for example, water/toluene or water/methylene chloride, if appropriate in the presence of a suitable phase transfer catalyst. Examples of such catalysts which may be mentioned are: tetrabutylammonium iodide, tetrabutylammonium bromide, tetrabutylammonium chloride, tributyl-methylphosphonium bromide, trimethyl-$C_{13}/C_{15}$-alkylammonium chloride, trimethyl-$C_{13}/C_{15}$-alkylammonium bromide, dibenzyl-dimethyl-ammonium methyl sulphate, dimethyl-$C_{12}/C_{14}$-alkylbenzylammonium chloride, dimethyl-$C_{12}/C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

The reaction temperatures can be varied within a substantial range in carrying out the process. The reaction is in general carried out at temperatures between −70° C. and +200° C., preferably at temperatures between 0° C. and 130° C.

The process is usually carried out under normal pressure. However, it is also possible to carry out the process under increased or reduced pressure.

For carrying out the process, in general 1.0 to 5.0 mol, preferably 1.0 to 2.5 mol, of compound of the formula (IIIa) and if appropriate 0.01 to 5.0 mol, preferably 1.0 to 3.0 mol, of reaction auxiliary are employed per mole of 1H-benzimidazole of the formula (IIa).

In a particular embodiment, it is also possible first to silylate the 1H-benzimidazoles of the formula (IIa) in a prior reaction step with the aid of customary silylation processes, for example with hexamethyldisilazane or trimethylsilyl chloride, if appropriate in the presence of a suitable catalyst, such as, for example, sulphuric acid, trifluoroacetic acid, ammonium sulphate, imidazole or saccharin, at temperatures between −20° C. and +50° C., and to react the 1-trimethylsilylbenzimidazoles thus obtainable with alkylating agents of the formula (IIa) by the process according to the invention in a subsequent second stage. In this case, it is advantageous to add tin tetrachloride as a catalyst for the alkylation reaction (compare, for example, Chem. Heterocycl. Com. USSR 24, 514 (1988)).

The reaction is carried out and the reaction products are worked up and isolated by known processes (in this context, compare also the preparation examples.

The end products of the formula (Ia) are purified with the aid of customary processes, for example by column chromatography or by recrystallisation.

Compounds which can be used according to the invention are also the new substituted benzimidazoles of the general formula (Ib)

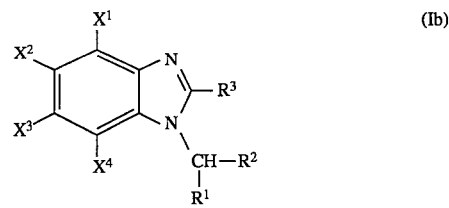

in which
R¹ represents hydrogen or alkyl, or represents optionally substituted aryl,
R² represents hydroxyl, cyano or alkoxy, or represents optionally substituted amino,
R³ represents perhalogenoalkyl and
X¹, X², X³ and X⁴ independently of one another in each case represent hydrogen, halogen or nitro, or represent optionally substituted aryloxy, but wherein at least one of the substituents X¹, X², X³ or X⁴ is other than hydrogen,
excluding the compound 1-cyanomethyl-2-trifluoromethyl-5,6-dichlorobenzimidazole.

Where appropriate, depending on the nature and number of substituents, the compounds of the formula (Ib) can exist as geometric and/or optical isomers or regioisomers or isomer mixtures thereof with varying compositions.

The new substituted benzimidazoles of the general formula (Ib) are obtained by a process in which 1H-benzimidazoles of the formula (IIb)

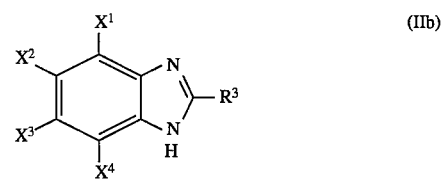

in which
R³, X¹, X², X³ and X⁴ have the abovementioned meaning, are reacted with compounds of the formula (IIIb)

in which
A represents a suitable leaving group,
R¹ has the abovementioned meaning and
R² has the abovementioned meaning,
if appropriate in the presence of a diluent and if appropriate in the presence of a reaction auxiliary.

Preferred compounds of the formula (Ib) are those in which
R¹ represents hydrogen, or represents straight-chain or branched alkyl having 1 to 8 carbon atoms, or represents phenyl which is optionally mono- or polysubstituted by identical or different substituents, possible substituents being:

halogen, cyano, nitro, in each case straight-chain or branched alkyl, alkoxy, alkylthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched alkoxyalkyl, alkoxyalkoxy, alkanoyl, alkoxycarbonyl or alkoximinoalkyl having in each case 1 to 6 carbon atoms in the individual alkyl parts, divalent dioxyalkylene having 1 to 5 carbon atoms, which is optionally mono- or polysubstituted by identical or different substituents from the group comprising halogen and/or straight-chain or branched alkyl having 1 to 6 carbon atoms and/or straight-chain or branched halogenoalkyl having 1 to 6 carbon atoms and 1 to 13 identical or different halogen atoms, or phenyl which is optionally mono- or polysubstituted by identical or different substituents from the group comprising halogen and/or straight-chain or branched alkyl having 1 to 6 carbon atoms and/or straight-chain or branched halogenoalkyl having 1 to 6 carbon atoms and 1 to 13 identical or different halogen atoms, $R^2$ represents hydroxyl, cyano or alkoxy having 1 to 8 carbon atoms, or represents amino which is optionally mono- or disubstituted by identical or different substituents, possible substituents being: straight-chain or branched alkyl having 1 to 8 carbon atoms, straight-chain or branched alkenyl having 2 to 8 carbon atoms, cycloalkyl having 3 to 8 carbon atoms, alkoxycarbonyl, alkylthio-carbonyl, alkoxy-thiocarbonyl or alkylthio-thiocarbonyl having in each case 1 to 8 carbon atoms in the individual straight-chain or branched alkyl parts, divalent, cyclic alkanediyloxycarbonyl having 2 to 6 carbon atoms in the alkanediyl part, or arylalkyl or aryl having in each case 6 to 10 carbon atoms in the aryl part and, where appropriate, 1 to 6 carbon atoms in the straight-chain or branched alkyl part, in each case optionally mono- or polysubstituted by identical or different substituents, possible substituents on the aryl in each case being those mentioned for $R^1$, $R^3$ represents straight-chain or branched perhalogenoalkyl having 1 to 8 carbon atoms and 1 to 17 identical or different halogen atoms and $X^1$, $X^2$, $X^3$ and $X^4$ independently of one another in each case represent hydrogen, fluorine, chlorine, bromine, iodine or nitro, or represent aryloxy having 6 to 10 carbon atoms in the aryl part, which is optionally mono- or polysubstituted in the aryl part by identical or different substituents, possible substituents on the aryl being those mentioned for $R^1$ but wherein at least one of the substituents $X^1$, $X^2$, $X^3$ or $X^4$ is other than hydrogen, excluding the compound 1-cyanomethyl-2-trifluoromethyl-5,6-dichlorobenzimidazole.

Particularly preferred compounds of the formula (Ib) are those in which $R^1$ represents hydrogen, or represents straight-chain or branched alkyl having 1 to 6 carbon atoms, or represents phenyl which is optionally mono- to trisubstituted by identical or different substituents, possible substituents being:

halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxyalkyl, alkoxyalkoxy, alkanoyl, alkoxycarbonyl or alkoximinoalkyl having in each case 1 to 4 carbon atoms in the individual alkyl parts, divalent dioxyalkylene having 1 to 4 carbon atoms, which is optionally mono- to hexasubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or phenyl which is optionally mono- to pentasubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, $R^2$ represents hydroxyl, cyano or alkoxy having 1 to 6 carbon atoms, or represents amino which is optionally mono- or disubstituted by identical or different substituents, possible substituents being:

straight-chain or branched alkyl having 1 to 6 carbon atoms, straight-chain or branched alkenyl having 2 to 6 carbon atoms, cycloalkyl having 3 to 7 carbon atoms, alkoxycarbonyl, alkylthio-carbonyl, alkoxythiocarbonyl or alkylthio-thiocarbonyl having in each case 1 to 6 carbon atoms in the individual straight-chain or branched alkyl parts, divalent, cyclic alkanediyloxycarbonyl having 2 to 5 carbon atoms in the alkanediyl part, or arylalkyl or aryl having in each case 6 or 10 carbon atoms in the aryl part and, where appropriate, 1 to 6 carbon atoms in the straight-chain or branched alkyl part, in each case optionally mono- to pentasubstituted by identical or different substituents, possible substituents on the aryl in each case being those mentioned for $R^1$, $R^3$ represents straight-chain or branched perhalogenoalkyl having 1 to 6 carbon atoms and 1 to 13 halogen atoms and $X^1$, $X^2$, $X^3$ and $X^4$ independently of one another in each case represent hydrogen, fluorine, chlorine, bromine, iodine or nitro, or represent aryloxy having 6 or 10 carbon atoms in the aryl part, which is optionally mono- to pentasubstituted in the aryl part by identical or different substituents, possible possible substituents on the aryl being those mentioned for $R^1$, but wherein at least one of the substituents $X^1$, $X^2$, $X^3$ or $X^4$ is other than hydrogen, excluding the compound 1-cyanomethyl-2-trifluoromethyl-5,6-dichlorobenzimidazole.

Preferred aryl radicals which may be mentioned are phenyl and naphthyl.

Especially preferred compounds of the formula (Ib) are those in which $R^1$ represents hydrogen, or represents straight-chain or branched alkyl having 1 to 4 carbon atoms, or represents phenyl which is optionally mono- or disubstituted by identical or different substituents, possible substituents being:

halogen, cyano, nitro, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxyalkyl, alkoxyalkoxy, alkanoyl, alkoxycarbonyl or alkoximinoalkyl having in each case 1 to 3 carbon atoms in the individual alkyl parts, divalent dioxyalkylene having 1 to 3 carbon atoms, which is optionally mono- to tetrasubstituted by identical or different substituents from the group comprising halogen and/or straight-chain or branched alkyl having 1 to 3 carbon atoms and/or straight-chain or branched halogeno alkyl having 1 to 3 carbon atoms and 1 to 7 identical or different halogen atoms, or phenyl which is optionally mono- to trisubstituted by identical or different substituents from the group comprising halogen and/or straight-chain or branched alkyl having 1 to 3 carbon atoms and/or straight-chain or branched halogenoalkyl having 1 to 3 carbon atoms and 1 to 7 identical or different halogen atoms, $R^2$ represents hydroxyl, cyano or alkoxy having 1 to 6 carbon atoms, or represents amino which is optionally mono- or disubstituted by identical or different substituents, possible substituents being:
  straight-chain or branched alkyl having 1 to 4 carbon atoms, straight-chain or branched alkenyl having 2 to 4 carbon atoms, cycloalkyl having 3 to 6 carbon atoms, alkoxycarbonyl, alkylthio-carbonyl, alkoxythiocarbonyl or alkylthio-thiocarbonyl having in each case i to 4 carbon atoms in the individual straight-chain or branched alkyl parts, divalent, cyclic alkanediyloxycarbonyl having 2 to 4 carbon atoms in the alkanediyl part, or phenylalkyl or phenyl having, where appropriate, 1 to 3 carbon atoms in the straight-chain or branched alkyl part, in each case optionally mono- or disubstituted by identical or different substituents, possible substituents on the phenyl in each case being those mentioned for $R^1$, $R^3$ represents straight-chain or branched perhalogenoalkyl having 1 to 4 carbon atoms and 1 to 9 halogen atoms, or represents cyano and $X^1$, $X^2$, $X^3$ and $X^4$ independently of one another in each case represent hydrogen, chlorine, bromine or nitro, or represent phenyloxy which is optionally mono- to trisubstituted in the phenyl part by identical or different substituents, possible substituents on the phenyl in each case being those mentioned for $R^1$, but wherein at least one of the substituents $X^1$, $X^2$, $X^3$ or $X^4$ is other than hydrogen, excluding the compound 1-cyanomethyl-2-trifluoromethyl-5,6-dichlorobenzimidazole.

The following substituted benzimidazoles of the general formula (Ib) may be mentioned specifically:

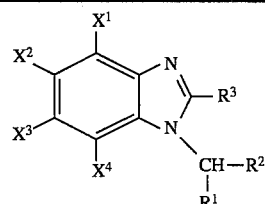

(Ib)

| $X^1$ | $X^2$ | $X^3$ | $X^4$ | $R^1$ | $R^2$ | $R^3$ |
|---|---|---|---|---|---|---|
| Br | H | Cl | H | H | N($C_2H_5$)($COOC_2H_5$) | $CF_3$ |
| Br | H | Br | H | H | N($C_2H_5$)($COOC_2H_5$) | $CF_3$ |
| H | Cl | Cl | H | H | N($C_2H_5$)($COOC_2H_5$) | $CF_3$ |
| Br | H | $NO_2$ | H | H | N($C_2H_5$)($COOC_2H_5$) | $CF_3$ |
| Cl | H | Cl | H | H | N($C_2H_5$)($COOC_2H_5$) | $CF_3$ |
| Cl | H | Br | H | H | N($C_2H_5$)($COOC_2H_5$) | $CF_3$ |

-continued (Ib)

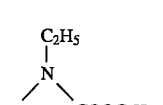

| X¹ | X² | X³ | X⁴ | R¹ | R² | R³ |
|---|---|---|---|---|---|---|
| H | H | NO$_2$ | H | H | $\begin{array}{c}C_2H_5\\ \diagdown\\ N\\ \diagup\phantom{xxx}\diagdown\\ \phantom{xx}COOC_2H_5\end{array}$ | CF$_3$ |
| Cl | H | 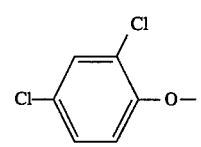 | H | H | $\begin{array}{c}C_2H_5\\ \diagdown\\ N\\ \diagup\phantom{xxx}\diagdown\\ \phantom{xx}COOC_2H_5\end{array}$ | CF$_3$ |
| Br | H | Cl | H | H | —O—C$_2$H$_5$ | CF$_3$ |
| Br | H | Br | H | H | —O—C$_2$H$_5$ | CF$_3$ |
| H | Cl | Cl | H | H | —O—C$_2$H$_5$ | CF$_3$ |
| Br | H | NO$_2$ | H | H | —O—C$_2$H$_5$ | CF$_3$ |
| Cl | H | Cl | H | H | —O—C$_2$H$_5$ | CF$_3$ |
| Cl | H | Br | H | H | —O—C$_2$H$_5$ | CF$_3$ |
| H | H | NO$_2$ | H | H | —O—C$_2$H$_5$ | CF$_3$ |
| Br | H | C$_6$H$_5$O | H | H | —O—C$_2$H$_5$ | CF$_3$ |
| Cl | H | 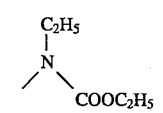 | H | H | —O—C$_2$H$_5$ | CF$_3$ |
| Cl | H | 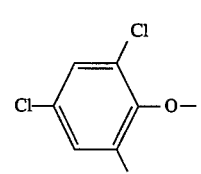 | H | H | —O—C$_2$H$_5$ | CF$_3$ |
| Br | H | Cl | H | H | $\begin{array}{c}C_2H_5\\ \diagdown\\ N\\ \diagup\phantom{xxx}\diagdown\\ \phantom{xx}COOC_2H_5\end{array}$ | C$_2$F$_5$ |
| Br | H | Br | H | H | $\begin{array}{c}C_2H_5\\ \diagdown\\ N\\ \diagup\phantom{xxx}\diagdown\\ \phantom{xx}COOC_2H_5\end{array}$ | C$_2$F$_5$ |
| H | Cl | Cl | H | H | $\begin{array}{c}C_2H_5\\ \diagdown\\ N\\ \diagup\phantom{xxx}\diagdown\\ \phantom{xx}COOC_2H_5\end{array}$ | C$_2$F$_5$ |
| Br | H | NO$_2$ | H | H | $\begin{array}{c}C_2H_5\\ \diagdown\\ N\\ \diagup\phantom{xxx}\diagdown\\ \phantom{xx}COOC_2H_5\end{array}$ | C$_2$F$_5$ |
| Cl | H | Cl | H | H | $\begin{array}{c}C_2H_5\\ \diagdown\\ N\\ \diagup\phantom{xxx}\diagdown\\ \phantom{xx}COOC_2H_5\end{array}$ | C$_2$F$_5$ |

-continued

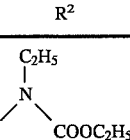

(Ib)

| X¹ | X² | X³ | X⁴ | R¹ | R² | R³ |
|---|---|---|---|---|---|---|
| Cl | H | Br | H | H | $\underset{\underset{COOC_2H_5}{N}}{C_2H_5}$ | $C_2F_5$ |
| H | H | $NO_2$ | H | H | $\underset{\underset{COOC_2H_5}{N}}{C_2H_5}$ | $C_2F_5$ |
| Br | H | $C_6H_5O$ | H | H | $\underset{\underset{COOC_2H_5}{N}}{C_2H_5}$ | $C_2F_5$ |
| Cl | H | 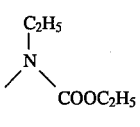 | H | H | $\underset{\underset{COOC_2H_5}{N}}{C_2H_5}$ | $C_2F_5$ |
| Cl | H | 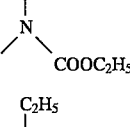 | H | H | $\underset{\underset{COOC_2H_5}{N}}{C_2H_5}$ | $C_2F_5$ |
| Br | H | Cl | H | H | $-O-C_2H_5$ | $C_2F_5$ |
| Br | H | Br | H | H | $-O-C_2H_5$ | $C_2F_5$ |
| H | Cl | Cl | H | H | $-O-C_2H_5$ | $C_2F_5$ |
| Br | H | $NO_2$ | H | H | $-O-C_2H_5$ | $C_2F_5$ |
| Cl | H | Cl | H | H | $-O-C_2H_5$ | $C_2F_5$ |
| Cl | H | Br | H | H | $-O-C_2H_5$ | $C_2F_5$ |
| H | H | $NO_2$ | H | H | $-O-C_2H_5$ | $C_2F_5$ |
| Br | H | $C_6H_5O$ | H | H | $-O-C_2H_5$ | $C_2F_5$ |
| Cl | H | 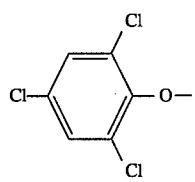 | H | H | $-O-C_2H_5$ | $C_2F_5$ |
| Cl | H | 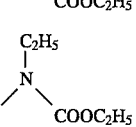 | H | H | $-O-C_2H_5$ | $C_2F_5$ |
| Br | H | Cl | H | H | $\underset{\underset{COOC_2H_5}{N}}{C_2H_5}$ | $n\text{-}C_3F_7$ |
| Br | H | Br | H | H | $\underset{\underset{COOC_2H_5}{N}}{C_2H_5}$ | $n\text{-}C_3F_7$ |

-continued

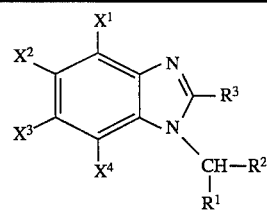
(Ib)

| X¹ | X² | X³ | X⁴ | R¹ | R² | R³ |
|---|---|---|---|---|---|---|
| H | Cl | Cl | H | H | $C_2H_5-N(CH_3)-COOC_2H_5$ | n-$C_3F_7$ |
| Br | H | $NO_2$ | H | H | $C_2H_5-N(CH_3)-COOC_2H_5$ | n-$C_3F_7$ |
| Cl | H | Cl | H | H | $C_2H_5-N(CH_3)-COOC_2H_5$ | n-$C_3F_7$ |
| Cl | H | Br | H | H | $C_2H_5-N(CH_3)-COOC_2H_5$ | n-$C_3F_7$ |
| H | H | $NO_2$ | H | H | $C_2H_5-N(CH_3)-COOC_2H_5$ | n-$C_3F_7$ |
| Br | H | $C_6H_5O$ | H | H | $C_2H_5-N(CH_3)-COOC_2H_5$ | n-$C_3F_7$ |
| Cl | H | 2,4,6-trichlorophenoxy | H | H | $C_2H_5-N(CH_3)-COOC_2H_5$ | n-$C_3F_7$ |
| Cl | H | 2,4-dichlorophenoxy | H | H | $C_2H_5-N(CH_3)-COOC_2H_5$ | n-$C_3F_7$ |
| Br | H | Cl | H | H | $-O-C_2H_5$ | n-$C_3F_7$ |
| Br | H | Br | H | H | $-O-C_2H_5$ | n-$C_3F_7$ |
| H | Cl | Cl | H | H | $-O-C_2H_5$ | n-$C_3F_7$ |
| Br | H | $NO_2$ | H | H | $-O-C_2H_5$ | n-$C_3F_7$ |
| Cl | H | Cl | H | H | $-O-C_2H_5$ | n-$C_3F_7$ |
| Cl | H | Br | H | H | $-O-C_2H_5$ | n-$C_3F_7$ |
| H | H | $NO_2$ | H | H | $-O-C_2H_5$ | n-$C_3F_7$ |
| Br | H | $C_6H_5O$ | H | H | $-O-C_2H_5$ | n-$C_3F_7$ |
| Cl | H | 2,4,6-trichlorophenoxy | H | H | $-O-C_2H_5$ | n-$C_3F_7$ |

-continued
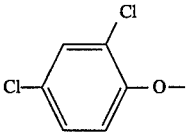 (Ib)
| X¹ | X² | X³ | X⁴ | R¹ | R² | R³ |
|---|---|---|---|---|---|---|
| Cl | H | 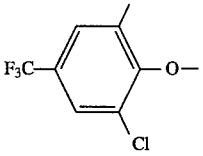 | H | H | —O—$C_2H_5$ | n-$C_3F_7$ |
| Cl | H | 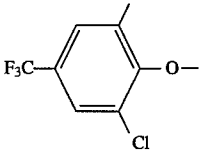 | H | H | —O—$C_2H_5$ | $CF_3$ |
| Cl | H | 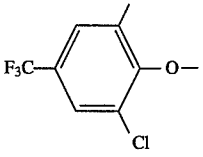 | H | H | —O—$C_2H_5$ | $C_2F_5$ |
| Cl | H | 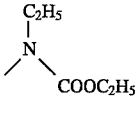 | H | H | —O—$C_2H_5$ | n-$C_3F_7$ |
| Cl | H | 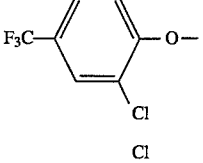 | H | H | 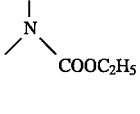 | $CF_3$ |
| Cl | H | 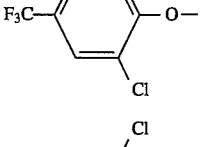 | H | H | 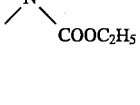 | $C_2F_5$ |
| Cl | H | 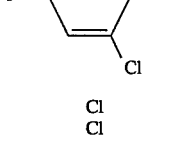 | H | H | $\begin{array}{c} C_2H_5 \\ | \\ N \\ \diagdown COOC_2H_5 \end{array}$ | n-$C_3F_7$ |
| Cl | H | Cl | H | H | —O—$C_2H_5$ | n-$C_7H_{15}$ |
| H | Cl | Cl | H | H | —O—$C_2H_5$ | n-$C_7H_{15}$ |

-continued (Ib)

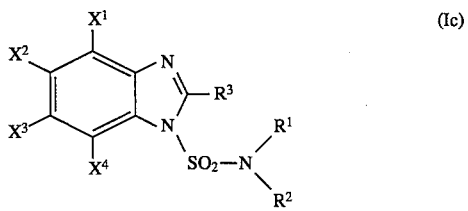

| $X^1$ | $X^2$ | $X^3$ | $X^4$ | $R^1$ | $R^2$ | $R^3$ |
|---|---|---|---|---|---|---|
| Cl | H | Cl | H | H | 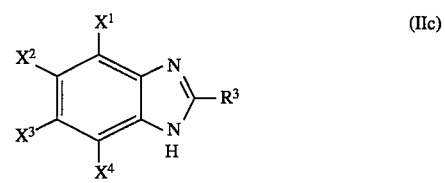 | $n\text{-}C_7H_{15}$ |
| H | Cl | Cl | H | H | 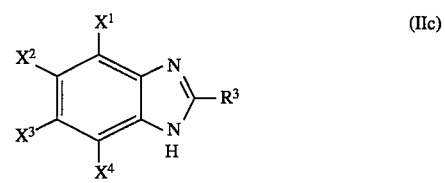 | $n\text{-}C_7H_{15}$ |
| Cl | H | 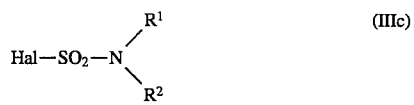 | H | H | 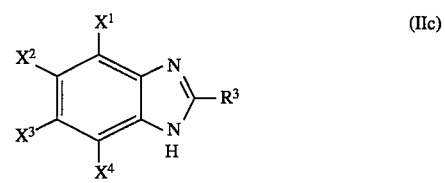 | $n\text{-}C_7H_{15}$ |

The preparation of the compounds (Ib) is carried out as described for the compounds (Ia).

Compounds which can be used according to the invention are also the new substituted benzimidazoles of the general formula (Ic)

(Ic)

in which $R^1$ represents hydrogen, alkyl, halogenoalkyl or cycloalkyl, or represents optionally substituted aryl, $R^2$ represents hydrogen, alkyl, halogenoalkyl or cycloalkyl, or represents optionally substituted aryl, $R^3$ represents fluoroalkyl and $X^1$, $X^2$, $X^3$ and $X^4$ independently of one another in each case represent hydrogen, halogen, cyano or nitro, or represent in each case optionally substituted alkyl, alkoxy, alkylthio, alkylsulphinyl, alkylsulphonyl or cycloalkyl, or represent optionally substituted, fused dioxyalkylene, or represent hydroxycarbonyl, alkylcarbonyl, alkoxycarbonyl or cycloalkyloxycarbonyl, or represent in each case optionally substituted amino or aminocarbonyl, or represent in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but wherein at least one of the substituents $X^1$, $X^2$, $X^3$ and $X^4$ is other than hydrogen, excluding the compounds 1-(N,N-dimethylaminosulphonyl)-2-trifluoromethyl-4-nitro-6-trifluoromethyl-benzimidazole, 1-(N,N-diethylaminosulphonyl)-2-trifluoromethyl-4-nitro-6-trifluoromethyl-benzimidazole and 1-[N,N-bis-(n-propyl)-aminosulphonyl]-2-trifluoromethyl-4-nitro-6-trifluoromethyl-benzimidazole.

Where appropriate, depending on the nature and number of substituents, the compounds of the formula (Ic) can exist as geometric and/or optical isomers or regioisomers or isomer mixtures thereof with varying compositions.

The new benzimidazoles of the general formula (Ic) are obtained by a process in which 1H-benzimidazoles of the formula (IIc)

(IIc)

in which $R^3$, $X^1$, $X^2$, $X^3$ and $X^4$ have the abovementioned meaning, are reacted with halogenosulphonamides of the formula (IIIc)

$$\text{Hal}-SO_2-N\begin{matrix}R^1\\R^2\end{matrix}$$ (IIIc)

in which

Hal represents halogen and $R^1$ has the abovementioned meaning and $R^2$ has the abovementioned meaning, if appropriate in the presence of a diluent and if appropriate in the presence of a reaction auxiliary.

Preferred compounds of the formula (Ic) are those in which $R^1$ represents hydrogen, or represents straight-chain or branched alkyl having 1 to 8 carbon atoms, or represents straight-chain or branched halogenoalkyl having 1 to 8 carbon atoms and 1 to 17 identical or different halogen atoms, or represents cycloalkyl having 3 to 8 carbon atoms, or represents aryl having 6 to 10 carbon atoms, which is optionally mono- or polysubstituted by identical or different substituents, possible substituents on the aryl being:

halogen, cyano, nitro, in each case straight-chain or branched alkyl, alkoxy, alklthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched alkoxyalkyl, alkoxyalkoxy, alkanoyl, alkoxycarbonyl or alkoximinoalkyl having in each case 1 to 6 carbon atoms in the individual alkyl parts, divalent dioxyalkylene having 1 to 5 carbon atoms, which is optionally mono- or polysubstituted by identical or different substituents from the group comprising halogen and/or straight-chain or branched alkyl having 1 to 6 carbon atoms and/or straight-chain or branched halogenoalkyl having 1 to 6 carbon atoms and 1 to 13 identical or different halogen atoms, or phenyl which is optionally mono- or polysubstituted by identical or different substituents from the group comprising halogen and/or straight-chain or branched alkyl having 1 to 6 carbon atoms and/or straight-chain or branched halogenoalkyl having 1 to 6 carbon atoms and 1 to 13 identical or different halogen atoms, $R^2$ represents hydrogen, or represents straight-chain or branched alkyl having 1 to 8 carbon atoms, or represents straight-chain or branched halogenoalkyl having 1 to 8 carbon atoms and 1 to 17 identical or different halogen atoms, or represents cycloalkyl having 3 to 8 carbon atoms, or represents aryl having 6 to 10 carbon atoms, which is optionally mono- or polysubstituted by identical or different substituents, possible substituents on the aryl being those mentioned for $R^1$, $R^3$ represents straight-chain or branched fluoroalkyl having 1 to 8 carbon atoms and 1 to 17 fluorine atoms and $X^1$, $X^2$, $X^3$ and $X^4$ independently of one another in each case represent hydrogen, fluorine, chlorine, bromine, iodine, cyano or nitro, or represent in each case straight-chain or branched alkyl, alkoxy, alkylthio, alkylsulphinyl or alkylsulphonyl having in each case 1 to 8 carbon atoms, or represent cycloalkyl having 3 to 8 carbon atoms, or represent in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, or represent divalent dioxyalkylene having 1 to 5 carbon atoms, which is optionally mono- or polysubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or furthermore represent hydroxycarbonyl, or represent in each case straight-chain or branched alkylcarbonyl or alkoxycarbonyl having in each case 1 to 6 carbon atoms in the alkyl part, or represent cycloalkyloxycarbonyl having 3 to 8 carbon atoms in the cycloalkyl part, or represent amino or aminocarbonyl, in each case optionally mono- or polysubstituted by identical or different substituents, possible substituents on the amino in each case being:

in each case straight-chain or branched alkyl having 1 to 6 carbon atoms, halogenoalkyl having 1 to 6 carbon atoms and 1 to 13 halogen atoms, alkoxyalkyl or alkylcarbonyl having in each case 1 to 6 carbon atoms in the individual alkyl parts, or arylcarbonyl, arylsulphonyl, arylaminocarbonyl or arylmethylsulphonyl having in each case 6 to 10 carbon atoms in the aryl part, in each case optionally mono- or polysubstituted in the aryl part by identical or different substituents, possible substituents on the aryl in each case being those mentioned for $R^1$; or furthermore represent aryl, aryloxy, arylthio, arylsulphinyl, arylsulphonyl, arylsulphonyloxy, arylcarbonyl, aryloxycarbonyl, arylthiomethylsulphonyl or arylazo having in each case 6 to 10 carbon atoms in the aryl part, in each case optionally mono- or polysubstituted in the aryl part by identical or different substituents, possible possible substituents on the aryl in each case being those mentioned for $R^1$, but wherein at least one of the substituents $X^1$, $X^2$, $X^3$ or $X^4$ is other than hydrogen, excluding the compounds 1-(N,N-dimethylaminosulphonyl)-2-trifluoromethyl-4-nitro-6-trifluoromethyl-benzimidazole, 1-(N,N-diethylaminosulphonyl)-2-trifluoromethyl-4-nitro-6-trifluoromethyl-benzimidazole and 1-[N,N-bis-(n-propyl)-aminosulphonyl]-2-trifluoromethyl-4-nitro-6-trifluoromethylbenzimidazole.

Particularly preferred compounds of the formula (Ic) are those in which $R^1$ represents hydrogen, or represents straight-chain or branched alkyl having 1 to 6 carbon atoms, or represents straight-chain or branched halogenoalkyl having 1 to 6 carbon atoms and 1 to 13 identical or different halogen atoms, or represents cycloalkyl having 3 to 7 carbon atoms, or represents aryl having 6 or 10 carbon atoms, which is optionally mono- to pentasubstituted by identical or different substituents, possible substituents on the aryl being:

halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxyalkyl, alkoxyalkoxy, alkanoyl, alkoxycarbonyl or alkoximinoalkyl having in each case 1 to 4 carbon atoms in the individual alkyl parts, divalent di-oxyalkylene having 1 to 4 carbon atoms, which is optionally mono- to hexasubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or phenyl which is optionally mono- to pentasubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, $R^2$ represents hydrogen, or represents straight-chain or branched alkyl having 1 to 6 carbon atoms, or represents straight-chain or branched halogenoalkyl having 1 to 6 carbon atoms and 1 to 13 identical or different halogen atoms, or represents cycloalkyl having 3 to 7 carbon atoms, or represents aryl having 6 or 10 carbon atoms, which is optionally mono- to pentasubstituted by identical or different substituents, possible substituents on the aryl being those mentioned for $R^1$, $R^3$ represents straight-chain or branched fluoroalkyl having 1 to 6 carbon atoms and 1 to 13 fluorine atoms and $X^1$, $X^2$, $X^3$ and $X^4$ independently of one another in each case represent hydrogen, fluorine, chlorine, bromine, cyano or nitro, or represent in each case straight-chain or branched alkyl, alkoxy, alkylthio, alkylsulphinyl or alkylsulphonyl having in each case 1to 6 carbon atoms, or represent cycloalkyl having 3 to 7 carbon atoms, or represent in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, or represent divalent dioxyalkylene having 1 to 4 carbon atoms, which is optionally mono- to hexasubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms, or furthermore represent hydroxycarbonyl, or represent in each case straight-chain or branched alkylcarbonyl or alkoxycarbonyl having in each case 1 to 4 carbon atoms in the alkyl part, or represent cycloalkyloxycarbonyl having 3 to 7 carbon atoms in the cycloalkyl part, or represent amino or aminocarbonyl, in each case optionally mono- or disubstituted by identical or different substituents, possible substituents on the amino in each case being:

in each case straight-chain or branched alkyl having 1 to 4 carbon atoms, halogenoalkyl having 1 to 4 carbon atoms and 1 to 9 halogen atoms, alkoxyalkyl or alkylcarbonyl having in each case 1 to 4 carbon atoms in the individual alkyl parts, or arylcarbonyl, arylsulphonyl, arylaminocarbonyl or arylmethylsulphonyl having in each case 6 or 10 carbon atoms in the aryl part, in each case optionally mono- to pentasubstituted in the aryl part by identical or different substituents, possible substituents on the aryl in each case being those mentioned for $R^1$;

or furthermore represent aryl, aryloxy, arylthio, arylsulphinyl, arylsulphonyl, arylsulphonyloxy, arylcarbonyl, aryloxycarbonyl, arylthiomethylsulphonyl or arylazo having in each case 6 or 10 carbon atoms in the aryl part, in each case optionally mono- to pentasubstituted in the aryl part by identical or different substituents, possible possible substituents on the aryl in each case being those mentioned for $R^1$, but wherein at least one of the substituents $X^1$, $X^2$, $X^3$ and $X^4$ is other than hydrogen, excluding the compounds 1-(N,N-dimethylaminosulphonyl)-2 -trifluoromethyl-4-nitro-6-trifluoromethyl-benzimidazole, 1-(N,N-diethylaminosulphonyl)-2-trifluoromethyl-4-nitro- 6-trifluoromethyl-benzimidazole and 1-[N,N-bis-(n-propyl)-aminosulphonyl]-2-trifluoromethyl-4-nitro-6 -trifluoromethylbenzimidazole. Aryl radicals which may be mentioned are phenyl and naphthyl.

Especially preferred compounds of the formula (Ic) are those in which $R^1$ represents hydrogen, or represents straight-chain or branched alkyl having 1 to 4 carbon atoms, or represents straight-chain or branched halogenoalkyl having 1 to 4 carbon atoms and 1 to 9 identical or different halogen atoms, or represents cycloalkyl having 3 to 6 carbon atoms, or represents phenyl which is optionally mono- to trisubstituted by identical or different substituents, possible substituents on the phenyl being:

halogen, cyano, nitro, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxyalkyl, alkoxyalkoxy, alkanoyl, alkoxycarbonyl or alkoximinoalkyl having in each case 1 to 3 carbon atoms in the individual alkyl parts, divalent dioxyalkylene having 1 to 3 carbon atoms, which is optionally mono- to tetrasubstituted by identical or different substituents from the group comprising halogen and/or straight-chain or branched alkyl having 1 to 3 carbon atoms and/or straight-chain or branched halogenoalkyl having 1 to 3 carbon atoms and 1 to 7 identical or different halogen atoms, or phenyl which is optionally mono- to trisubstituted by identical or different substituents from the group comprising halogen and/or straight-chain or branched alkyl having 1 to 3 carbon atoms and/or straight-chain or branched halogenoalkyl having 1 to 3 carbon atoms and 1 to 7 identical or different halogen atoms, $R^2$ represents hydrogen, or represents straight-chain or branched alkyl having 1 to 4 carbon atoms, or represents straight-chain or branched halogenoalkyl having 1 to 4 carbon atoms and 1 to 9 identical or different halogen atoms, or represents cycloalkyl having 3 to 6 carbon atoms, or represents phenyl which is optionally mono- to trisubstituted by identical or different substituents, possible substituents on the phenyl being those mentioned for $R^1$, $R^3$ represents straight-chain or branched fluoroalkyl having 1 to 4 carbon atoms and 1 to 9 fluorine atoms and $X^1$, $X^2$, $X^3$ and $X^4$ independently of one another in each case represent hydrogen, chlorine, bromine, cyano or nitro, or represent in each case straight-chain or branched alkyl, alkoxy, alkylthio, alkylsulphinyl or alkylsulphonyl having in each case 1 to 4 carbon atoms, or represent cycloalkyl having 3, 5 or 6 carbon atoms, or represent in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, or represent divalent dioxyalkylene having 1 to 3 carbon atoms, which is optionally mono- to tetrasubstituted by identical or different substituents from the group comprising halogen and/or straight-chain or branched alkyl having 1 to 3 carbon atoms and/or straight-chain or branched halogenoalkyl having 1 to 3 carbon atoms and 1 to 7 identical or different halogen atoms, or furthermore represent hydroxycarbonyl, or represent in each case straight-chain or branched alkylcarbonyl or alkoxycarbonyl having in each case 1 to 3 carbon atoms in the alkyl part, or represent cycloalkyloxycarbonyl having 3, 5 or 6 carbon atoms in the cycloalkyl part, or represent amino or aminocarbonyl, in each case optionally mono- or disubstituted by identical or different substituents, possible substituents on the amino in each case being:

in each case straight-chain or branched alkyl having 1 to 3 carbon atoms, halogenoalkyl having 1 to 3 carbon atoms and 1 to 7 halogen atoms, alkoxyalkyl or alkylcarbonyl having in each case 1 to 3 carbon atoms in the individual alkyl parts, or phenylcarbonyl, phenylsulphonyl, phenylaminocarbonyl or phenylmethylsulphonyl, in each case optionally mono- to trisubstituted in the phenyl part by identical or different substituents, possible substituents on the phenyl in each case being those mentioned for R; or furthermore represent phenyl, phenyloxy, phenylthio, phenylsulphinyl, phenylsulphonyl, phenylsulphonyloxy, phenylcarbonyl, phenyloxycarbonyl, phenylthiomethylsulphonyl or phenylazo, in each case optionally mono- to trisubstituted in the phenyl part by identical or different substituents, possible possible substituents on the phenyl in each case being those mentioned for $R^1$, but wherein at least one of the substituents $X^1$, $X^2$, $X^3$ and $X^4$ is other than hydrogen, excluding the compounds 1-(N,N-dimethylaminosulphonyl)-2-trifluoromethyl-4-nitro-6-trifluoromethyl-benzimidazole, 1-(N,N-diethylaminosulphonyl)-2-trifluoromethyl-4-nitro-6-trifluoromethyl-benzimidazole and 1-[N,N-bis-(n-propyl)-aminosulphonyl]-2-trifluoromethyl-4-nitro-6-trifluoromethyl-benzimidazole.

The following substituted benzimidazoles of the general formula (Ic) may be mentioned specifically, in addition to the compounds mentioned in the preparation examples:

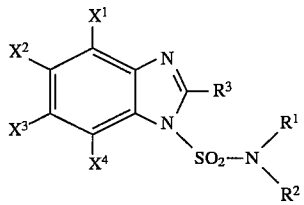

(I)

| $X^1$ | $X^2$ | $X^3$ | $X^4$ | $R^1$ | $R^2$ | $R^3$ |
|---|---|---|---|---|---|---|
| Br | H | $CF_3$ | H | $CH_3$ | $CH_3$ | $C_2F_5$ |
| Br | H | $CF_3$ | H | $CH_3$ | $CH_3$ | $C_3F_7$ |
| Br | H | $CF_3$ | H | $CH_3$ | $CH_3$ | $C_7F_{15}$ |
| $CF_3$ | H | $CF_3$ | H | $CH_3$ | $CH_3$ | $CF_3$ |
| $CF_3$ | H | $CF_3$ | H | $CH_3$ | $CH_3$ | $C_2F_5$ |
| $CF_3$ | H | $CF_3$ | H | $CH_3$ | $CH_3$ | $C_3F_7$ |
| $CF_3$ | H | $CF_3$ | H | $CH_3$ | $CH_3$ | $C_7F_{15}$ |
| Cl | H | $SCF_3$ | H | $CH_3$ | $CH_3$ | $CF_3$ |
| Cl | H | $SCF_3$ | H | $CH_3$ | $CH_3$ | $C_2F_5$ |
| Cl | H | $SCF_3$ | H | $CH_3$ | $CH_3$ | $C_3F_7$ |
| Cl | H | $SCF_3$ | H | $CH_3$ | $CH_3$ | $C_7F_{15}$ |
| Br | H | $SCF_3$ | H | $CH_3$ | $CH_3$ | $CF_3$ |
| Br | H | $SCF_3$ | H | $CH_3$ | $CH_3$ | $C_2F_5$ |
| Br | H | $SCF_3$ | H | $CH_3$ | $CH_3$ | $C_3F_7$ |
| Br | H | $SCF_3$ | H | $CH_3$ | $CH_3$ | $C_7F_{15}$ |
| COO-n-$C_4H_9$ | H | $CF_3$ | H | $CH_3$ | $CH_3$ | $CF_3$ |
| COO-n-$C_4H_9$ | H | $CF_3$ | H | $CH_3$ | $CH_3$ | $C_2F_5$ |
| COO-n-$C_4H_9$ | H | $CF_3$ | H | $CH_3$ | $CH_3$ | $C_3F_7$ |
| COO-n-$C_4H_9$ | H | $CF_3$ | H | $CH_3$ | $CH_3$ | $C_7F_{15}$ |
| H | $CF_3$ | $CF_3$ | H | $CH_3$ | $CH_3$ | $CF_3$ |
| H | $CF_3$ | $CF_3$ | H | $CH_3$ | $CH_3$ | $C_2F_5$ |
| H | $CF_3$ | $CF_3$ | H | $CH_3$ | $CH_3$ | $C_3F_7$ |
| H | $CF_3$ | $CF_3$ | H | $CH_3$ | $CH_3$ | $C_7F_{15}$ |
| H | $OCF_3$ | $OCF_3$ | H | $CH_3$ | $CH_3$ | $C_2F_5$ |
| H | $OCF_3$ | $OCF_3$ | H | $CH_3$ | $CH_3$ | $C_3F_7$ |

-continued

| $X^1$ | $X^2$ | $X^3$ | $X^4$ | $R^1$ | $R^2$ | $R^3$ |
|---|---|---|---|---|---|---|
| H | $OCF_3$ | $OCF_3$ | H | $CH_3$ | $CH_3$ | $C_7F_{15}$ |
| H | —O—$CF_2$—$CF_2$—O— | | H | $CH_3$ | $CH_3$ | $C_2F_5$ |
| H | —O—$CF_2$—$CF_2$—O— | | H | $CH_3$ | $CH_3$ | $C_3F_7$ |
| H | —O—$CF_2$—$CF_2$—O— | | H | $CH_3$ | $CH_3$ | $C_7F_{15}$ |
| H | Cl | $SCF_3$ | H | $CH_3$ | $CH_3$ | $CF_3$ |
| H | Cl | $SCF_3$ | H | $CH_3$ | $CH_3$ | $C_2F_5$ |
| H | Cl | $SCF_3$ | H | $CH_3$ | $CH_3$ | $C_3F_7$ |
| H | Cl | $SCF_3$ | H | $CH_3$ | $CH_3$ | $C_7F_{15}$ |
| H | $SCF_3$ | Cl | H | $CH_3$ | $CH_3$ | $CF_3$ |
| H | $SCF_3$ | Cl | H | $CH_3$ | $CH_3$ | $C_2F_5$ |
| H | $SCF_3$ | Cl | H | $CH_3$ | $CH_3$ | $C_3F_7$ |
| H | $SCF_3$ | Cl | H | $CH_3$ | $CH_3$ | $C_7F_{15}$ |
| H | Br | $SCF_3$ | H | $CH_3$ | $CH_3$ | $CF_3$ |
| H | Br | $SCF_3$ | H | $CH_3$ | $CH_3$ | $C_2F_5$ |
| H | Br | $SCF_3$ | H | $CH_3$ | $CH_3$ | $C_3F_7$ |
| H | Br | $SCF_3$ | H | $CH_3$ | $CH_3$ | $C_7F_{15}$ |
| H | $SCF_3$ | Br | H | $CH_3$ | $CH_3$ | $CF_3$ |
| H | $SCF_3$ | Br | H | $CH_3$ | $CH_3$ | $C_2F_5$ |
| H | $SCF_3$ | Br | H | $CH_3$ | $CH_3$ | $C_3F_7$ |
| H | $SCF_3$ | Br | H | $CH_3$ | $CH_3$ | $C_7F_{15}$ |

If, for example, 5,6-dichloro-2-trifluoromethyl-benzimidazole and N,N-diethyl-chlorosulphonamide are used as starting compounds, the course of the reaction for the preparation of the compound Ic can be represented by the following equation:

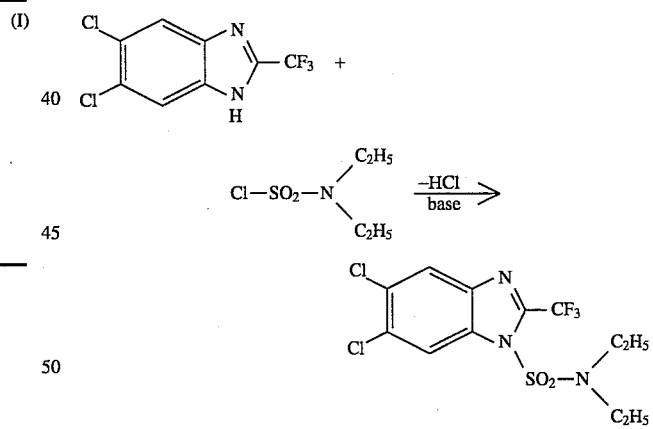

Formula (II c) provides a general definition of the 1H-benzimidazoles required as starting substances for carrying out the process according to the invention. In this formula (II), $R^3$, $X^1$, $X^2$, $X^3$ and $X^4$ preferably represent those radicals which have already been mentioned as preferred for these substituents in connection with the description of the compounds of the formula (I) according to the invention.

The 1H-benzimidazoles of the formula (II) are known or are obtainable by processes analogous to known processes (compare, for example, J. Amer. Chem. Soc. 75, 1292 [1953]; and U.S. Pat. No. 3,576,818). The process is carried out as described for the compounds Ia.

The active compounds are suitable for combating parasitic protozoa which occur on stock, breeding, zoo, laboratory and test animals and pets in animal husbandry and animal breeding and have a favourable toxicity to warm-blooded animals. They are active against all or some stages of development of the pests and against resistant and normally sensitive strains. Disease, fatalities and reductions in output (for example in the production of meat, milk, wool, hides, eggs, honey and the like) are to be reduced by combating the parasitic protozoa, so that a more economical and easier animal husbandry is possible by employing the active compounds.

The parasitic protozoa include: Mastigophora (Flagellata) such as, for example, Trypanosomatidae, for example Trypanosoma b. brucei, T.b. gambiense, T.b. rhodesiense, *T. congolense, T. cruzi, T. evansi, T. equinum, T. lewisi, T. percae, T. simiae, T. vivax, Leishmania brasiliensis, L. donovani, L. tropica*, such as, for example, Trichomonadidae, for example *Giardia lamblia, G. canis*.

Sarcomastigophora (Rhizopoda) such as Entamoebidae, for example *Entamoeba histolytica*, Hartmanellidae, for example Acanthamoeba sp., Hartmanella sp.

Apicomplexa (Sporozoa) such as Eimeridae, for example *Eimeria acervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. dabliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium* spec., *Isospora belli, I. canis, I. felis, I. ohioensis, I. rivolta*, I. spec., *I. suis*, Cystisospora spec., Cryptosporidium spec. such as Toxoplasmadidae, for example *Toxoplasma gondii*, such as Sarcocystidae, for example *Sarcocystis bovicanis, S. bovihominis, S. ovicanis, S. ovifelis*, S. spec., *S. suihominis*, such as Leucozoidae, for example Leucozytozoon simondi, such as Plasmodiidae, for example Plasmodium berghei, *P. falciparum, P. malariae, P. ovale, P. vivax*, P. spec., such as Piroplasmea, for example *Babesia argentina, B. bovis, B. canis*, B. spec., *Theileria parva*, Theileria spec., such as Adeleina, for example *Hepatozoon canis*, H. spec.

Furthermore Myxospora and Microspora, for example Glugea spec. Nosema spec.

Furthermore Pneumocystis carinii, as well as Ciliophora (Ciliata) such as, for example, *Balantidium coli*, Ichthiophthirius spec., Trichodina spec., Epistylis spec.

The compounds according to the invention are also active against protozoa which occur as parasites on insects. Such protozoa which may be mentioned are parasites of the phylum Microsporida, in particular of the genus Nosema. Nosema apis on honey bees may be mentioned in particular.

The stock and breeding animals include mammals, such as, for example, cattle, horses, sheep, pigs, goats, camels, water buffalo, donkeys, rabbits, fallow deer and reindeer, fur-bearing animals, such as, for example, mink, chinchillas and raccoons, and birds, such as, for example, chickens, geese, turkeys, ducks, pigeons and species of birds for keeping at home and in zoos. They furthermore include stock and ornamental fish.

Laboratory and test animals include mice, rats, guinea-pigs, golden hamsters, dogs and cats.

Pets include dogs and cats.

Fish include stock, breeding, aquarium and ornamental fish of all ages which live in fresh water and salt water. The stock and breeding fish include, for example, carp, eel, trout, white fish, salmon, bream, roach, rudd, chub, sole, plaice, halibut, Japanese yellowtail (*Seriola quinqueradiata*), Japanese eel (*Anguilla japonica*), red sea bream (Pagurus major), sea bass (*Dicentrarchus labrax*), grey mullet (*Mugilus cephalus*), Pompano, Gilthread seabream (*Sparus auratus*), Tilapia spp., Chichlidae species, such as, for example, Plagioscion, Channel catfish. The agents according to the invention are particularly suitable for treatment of fish fry, for example carp of 2–4 cm body length. The agents are also particularly suitable in the fattening of eels.

They can be used either prophylactically or therapeutically.

The active compounds are used enterally, parenterally, dermally or nasally, directly or in the form of suitable formulations.

Enteral use of the active compounds is effected, for example, orally in the form of powders, suppositories, tablets, capsules, pastes, drinks, granules, drenches, boli, medicated feed or drinking water. Dermal use is effected, for example, in the form of dipping (dips), spraying (sprays), bathing, washing, pouring on (pour-on and spot-on formulations) and dusting. Parenteral use is effected, for example, in the form of an injection (intramuscular, subcutaneous, intravenous or intraperitoneal) or by implants.

Suitable formulations are:

Solutions, such as injection solutions, oral solutions, concentrates for oral administration after dilution, solutions for use on the skin or in body cavities, pour-on formulations and gels;

Emulsions and suspensions for oral or dermal use and for injection; semi-solid formulations;

Formulations in which the active compound is processed in an ointment base or in an oil-in-water or water-in-oil emulsion base;

Solid formulations, such as powders, premixes or concentrates, granules, pellets, tablets, boll or capsules; aerosols and inhalates and shaped articles containing the active compound.

Injection solutions are administered intravenously, intramuscularly and subcutaneously.

Injection solutions are prepared by dissolving the active compound in a suitable solvent and adding any additives, such as solubilising agents, acids, bases, buffer salts, antioxidants or preservatives. The solutions are subjected to sterile filtration and bottling.

Solvents which may be mentioned are: physiologically tolerated solvents, such as water, alcohols, such as ethanol, butanol, benzyl acohol or glycerol, hydrocarbons, propylene glycol, polyethylene glycols, N-methylpyrrolidone and mixtures thereof.

If appropriate, the active compounds can also be dissolved in physiologically tolerated vegetable or synthetic oils which are suitable for injection.

Solubilising agents which may be mentioned are: solvents which promote solution of the active compound in the main solvent or prevent its precipitation. Examples are polyvinylpyrrolidone, polyoxyethylated castor oil and polyoxyethylated sorbitan esters.

Preservatives are: benzyl alcohol, trichlorobutanol, p-hydroxybenzoic acid esters and n-butanol.

Oral solutions are used directly. Concentrates are used orally after prior dilution to the use concentration. Oral solutions and concentrates are prepared as described above for the injection solutions, but sterile operations can be dispensed with.

Solutions for use on the skin are dripped on, brushed on, massaged in, sprayed on, atomised on or applied by dipping (dips), bathing or washing. These solutions are prepared as described above for the injection solutions.

It may be advantageous to add thickeners during the preparation. Thickeners are: inorganic thickeners, such as bentonites, colloidal silicic acid or aluminium monostearate, or organic thickeners, such as cellulose derivatives, polyvinyl alcohols and copolymers thereof, acrylates and metacrylates.

Gels are applied to or brushed on the skin or introduced into body cavities. Gels are prepared by adding an amount of thickener to solutions which have been prepared as described for the injection solutions such that a clear mass having an ointment-like consistency is formed. The thickeners mentioned earlier above are employed as thickener.

Pour-on formulations are poured or sprayed onto limited regions of the skin, the active compound either penetrating the skin and having a systemic action or spreading over the body surface.

Pour-on formulations are prepared by dissolving, suspending or emulsifying the active compound in suitable solvents or solvent mixtures which are tolerated by the skin. Further additives, such as dyestuffs, absorption-promoting substances, antioxidants, light stabilisers and adhesives, are added if appropriate.

Solvents which may be mentioned are: water, alkanols, glycols, polyethylene glycols, polypropylene glycols, glycerol, aromatic alcohols, such as benzyl alcohol, phenylethanol and phenoxyethanol, esters, such as ethyl acetate, butyl acetate and benzyl benzoate, ethers, such as alkylene glycol alkyl ethers, such as dipropylene glycol monomethyl ether and diethylene glycol mono-butyl ether, ketones, such as acetone and methyl ethyl ketone, aromatic and/or aliphatic hydrocarbons, vegetable or synthetic oils, DMF, dimethylacetamide, N-methylpyrrolidone and 2-dimethyl-4-oxymethylene-1,3-dioxolane.

Dyestuffs are all the dyestuffs permitted for use on animals, and can be dissolved or suspended.

Absorption-promoting substances are, for example, DMSO, spreading oils, such as isopropyl myristate, dipropylene glycol pelargonate, silicone oils, fatty acid esters, triglycerides and fatty alcohols.

Antioxidants are sulphites or metabisulphites, such as potassium metabisulphite, ascorbic acid, butylhydroxytoluene, butylhydroxyanisole and tocopherol.

Light stabilisers are, for example, substances from the class of benzophenones or novantisolic acid.

Adhesives are, for example, cellulose derivatives, starch derivatives, polyacrylates and naturally occurring polymers, such as alginates and gelatine.

Emulsions can be used orally, dermally or as injections.

Emulsions are either of the water-in-oil type or of the oil-in-water type.

They are prepared by dissolving the active compound either in the hydrophobic or in the hydrophilic phase and homogenising this solution with the solvent of the other phase with the aid of suitable emulsifiers and if appropriate other auxiliaries, such as dyestuffs, absorption-promoting substances, preservatives, antioxidants, light stabilisers and substances which increase the viscosity.

Hydrophobic phases (oils) which may be mentioned are: paraffin oils, silicone oils, naturally occurring vegetable oils, such as sesame oil, almond oil and castor oil, synthetic triglycerides, such as caprylic/capric acid bigylceride, a triglyceride mixture with plant fatty acids of chain length $C_{8-12}$ or other specifically selected naturally occurring fatty acids, partial glyceride mixtures of saturated or unsaturated fatty acids which may also contain hydroxyl groups, and mono- and diglycerides of $C_8/C_{10}$-fatty acids.

Fatty acid esters, such as ethyl stearate, di-n-butyryl adipate, hexyl laurate and dipropylene glycol pelargonate, esters of a branched fatty acid of medium chain length with saturated fatty alcohols of chain length $C_{16}$– $C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate and ethyl lactate, wax-like fatty acid esters, such as dibutyl phthalate, diisopropyl adipate, ester mixtures related to the latter and the like, and fatty alcohols, such as isotridecyl alcohol, 2-octyldodecanol, cetylstearyl alcohol and oleyl alcohol.

Fatty acids, such as, for example, oleic acid and its mixtures.

Hydrophilic phases which may be mentioned are: water, alcohols, such as, for example, propylene glycol, glycerol, sorbitol and their mixtures.

Emulsifiers which may be mentioned are: non-ionic surfactants, for example polyoxyethylated castor oil, polyoxyethylated sorbitan monooleate, sorbitan monostearate, glycerol monostearate, polyoxyethyl stearate and alkylphenol polyglycol ethers;

ampholytic surfactants, such as di-Na N-lauryl-β-iminodipropionate or lecithin;

anionic surfactants, such as Na lauryl sulphate, fatty alcohol ether sulphates and mono/dialkyl polyglycol ether orthophosphoric acid ester monoethanolamine salt; cationic surfactants, such as cetyltrimethylammonium chloride.

Other auxiliaries which may be mentioned are: substances which increase the viscosity and substances which stabilise the emulsion, such as carboxymethylcellulose, methylcellulose and other derivatives of cellulose and starch, polyacrylates, alginates, gelatine, gum arabic, polyvinylpyrrolidone, polyvinyl alcohol, copolymers of methyl vinyl ether and maleic anhydride, polyethylene glycols, waxes, colloidal silicic acid or mixtures of the substances listed.

Suspensions can be used orally, dermally or as an injection. They are prepared by suspending the active compound in a carrier liquid, if appropriate with addition of other auxiliaries, such as wetting agents, dyestuffs, absorption-promoting substances, preservatives, antioxidants and light stabilisers.

Carrier liquids which may be mentioned are all the homogeneous solvents and solvent mixtures.

Wetting agents (dispersing agents) which may be mentioned are the surfactants mentioned earlier above.

Other auxiliaries which may be mentioned are those mentioned earlier above.

Semi-solid formulations can be administered orally or dermally. They differ from the suspensions and emulsions described above only by their higher viscosity.

To prepare solid formulations, the active compound is mixed with suitable carrier substances, if appropriate with addition of auxiliaries, and the mixture is brought into the desired shape.

Carrier substances which may be mentioned are all the physiologically tolerated solid inert substances. Inorganic and organic substances are used all such substances. Inorganic substances are, for example, sodium chloride, carbonates, such as calcium carbonate, bicarbonates, aluminium oxides, silicic acids, aluminas, precipitated or colloidal silicon dioxide and phosphates.

Organic substances are, for example, sugars, cellulose, foodstuffs and feedstuffs, such as powdered milk, animal flours, cereal flours and shredded cereals, and starches.

Auxiliaries are preservatives, antioxidants and dyestuffs, which have already been listed earlier above.

Other suitable auxiliaries are lubricants and slip agents, such as, for example, magnesium stearate, stearic acid, talc and bentonites, disintegration-promoting substances, such as starch or crosslinked polyvinylpyrrolidone, binders, such as, for example, starch, gelatine or linear polyvinylpyrrolidone, and dry binders, such as microcrystalline cellulose.

The active compounds can also be present in the formulations as a mixture with synergists or with other active compounds.

Ready-to-use formulations contain the active compound in concentrations of 10 ppm–20 per cent by weight, preferably 0.1–10 percent by weight.

Formulations which are diluted before use contain the active compound in concentrations of 0.5–90 percent by weight, preferably 1 to 50 percent by weight.

In general, it has proved advantageous to administer amounts of about 0.5 to about 50 mg, preferably 1 to 20 mg, of active compound per kg of body weight per day to achieve effective results.

The active compounds can also be administered to the animals together with the feed or drinking water.

Feedstuffs and foodstuffs contain 0.01 to 100 ppm, preferably 0.5 to 50 ppm, of the active compound in combination with a suitable edible material.

Such a feedstuff and foodstuff can be used either for curing purposes or for prophylactic purposes.

Such a feedstuff or foodstuff is prepared by mixing a concentrate or a premix, which contains 0.5 to 30%, preferably 1 to 20% by weight of an active compound as a mixture with an edible organic or inorganic carrier, with customary feedstuffs. Edible carriers are, for example, maize flour or maize and soya bean flour or mineral salts, which preferably contain a small amount of an edible-dust-preventing oil, for example maize oil or soya oil. The premix obtained by this procedure can then be added to the complete feedstuff before it is fed to the animals.

As an example of use against coccidiosis there may be mentioned:

For curing and prophylaxis, for example, of coccidiosis in poultry, in particular in chickens, ducks, geese and turkeys, 0.1 to 100 ppm, preferably 0.5 to 100 ppm, of an active compound are mixed with a suitable edible material, for example a nutritious feedstuff. If desired, these amounts can be increased, especially if the active compound is tolerated well by the recipient. Administration can take place via the drinking water in a corresponding manner.

For treatment of individual animals, for example in the case of treatment of coccidiosis in mammals or of toxoplasmosis, amounts of active compound of 0.5 to 100 mg/kg of bodyweight daily are preferably administered in order to achieve the desired results. Nevertheless, it may at times be necessary to deviate from the amounts mentioned, in particular as a function of the body weight of the test animal or of the nature of the administration method, but also because of the type of animal and its individual reaction to the active compound or the nature of the formulation and the time or interval at which it is administered. Thus, in certain cases it may be sufficient to manage with less than the abovementioned minimum amount, while in other cases the upper limit mentioned must be exceeded. If relatively large amounts are administered, it may be expedient to divide these into several individual doses in the course of the day.

The compounds according to the invention moreover are active against various fish parasites included among the helminths (worms).

Parasites on fish include, from the subkingdom of the protozoa, species of the phylum of the Ciliata, for example *Ichthyophthirius multifiliis, Chilodonella cyprini*, Trichodina spp., Glossatella spp., Epistylis spp., of the phylum of the Myxosporidia, for example *Myxosoma cerebralis*, Myxidium spp., Myxobolus spp., Heneguya spp., Hoferellus spp., of the class of the Microsporidia, for example Glugea spp., Thelohania spp., Pleistophora spp., from the phylumof the Plathelminthes: trematodes; Monogenea, for example Dactylogyrus spp., Gyrodactylus spp., Pseudodactylogyrus spp., Diplozoon spp., Cestodes, for example from the groups of the Caryphyllidea (for example *Caryophyllaeus laticeps*), Pseudophyllidea (#or example Diphyllobothrium spp.), Tetraphyllidea (for example Phyllobothrium spp.) and Protocephalida (for example species of the genus Proteocephalus) and, from the phylum of the Arthropoda, various parasitic Crustacea, in particular from the subclasses of the Branchiura (fish lice) and Copepoda (copepods) and the orders of the Isopoda (isopods) and Amphipoda (amphipods).

Treatment of the fish is carried out either orally, for example via the feed, or by short-term treatment, "medicinal bath", into which the fish are put and in which they are kept for a period of time (minutes to several hours), for example when they are transferred from one breeding tank to another.

However, temporary or long-term treatment of the environment of the fish (for example entire pond systems, aquaria, tanks or pools) where the fish are held can also be carried out.

The active compound is administered in formulations appropriate for the applications.

The concentration of the active compound in the formulations is 1 ppm to 10% by weight.

Preferred formulations for short-term treatment used as a "medicinal bath", for example for treatment when transferring the fish or for treatment of the environment (pond treatment) of the fish, are solutions of the active compound in one or more polar solvents which have an alkaline reaction when diluted with water.

To prepare these solutions, the active compound is dissolved in a polar, water-soluble solvent, which either has an alkaline reaction or is added to an alkaline water-soluble substance. The latter is advantageously likewise dissolved in the solvent, but can also be suspended in the solvent and dissolve only in the water. In this case, after addition of the active compound solution, the water should have a pH of 7–10, but preferably a pH of 8–10.

The concentration of the active compound can be in the range from 0.5–50%, but preferably in a range from 1–25%.

Possible solvents are all the water-soluble solvents in which the active compound is soluble in a sufficient concentration and which are physiologically acceptable.

These solvents are ethyl alcohol, isopropyl alcohol, benzyl alcohol, glycerol, propylene glycol, polyethylene glycols, poly(oxoethylene)/poly(oxypropylene) polymers, basic alcohols, such as mono-, di- and triethanolamine, ketones, such as acetone or methyl ethyl ketone, esters, such as ethyl lactate, and furthermore N-methylpyrrolidone, dimethylacetamide and dimethylformamide, and furthermore dispersing and emulsifying agents, such as polyoxyethylated castor oil, polyethylene glycol sorbitan monooleate, polyethylene glycol stearate or polyethylene glycol ether or polyethylene glycol alkylamines.

Bases for adjustment of the alkaline pH which may be mentioned are organic bases, such as basic amino acids, such as L- or D,L-arginine, L- or D,L-lysine, methylglucosamine, glucosamine or 2-amino-2-hydroxymethylpropane-1,3-diol, or furthermore such as N,N,N',N'-tetrakis-(2-hydroxypropyl)-ethylenediamine or polyether tetrol based on ethylenediamine (molecular weight 480– 420), and inorganic bases, such as ammonia or sodium carbonate, if appropriate with addition of water.

The formulations can also contain 0.1 to 20% by weight, preferably 0.1–10% by weight, of other formulation auxiliaries, such as antioxidants, surfactants, suspension stabilisers and thickeners, such as, for example, methylcellulose, alginates, polysaccharides, galactomannans and colloidal silicic acid. It is likewise possible to add colour, aroma and builder substances for animal nutrition. Acids which form a buffer system together with the base introduced or reduce the pH of the solution may also be mentioned here.

The concentration of the active compounds during use depends on the nature and duration of the treatment and on the age and condition of the fish treated. For shortterm treatment, it is, for example, 2–50 mg of active compound per liter of water, preferably 5–10 mg per liter, over a treatment period of 3–4 hours. Treatment of young carp is carried out, for example, with a concentration of 5–10 mg/l over a treatment period of about 1– 4 hours.

Eels are treated with concentrations of about 5 mg/l for about 4 hours.

A correspondingly lower concentration can be chosen for a longer treatment period or for long-term treatment.

0.1–5 mg of active compound per liter of water can be used for pond treatments.

Formulations for use as a feed additive have, for example, the following composition:

| | | |
|---|---|---|
| a) | Active compound of the formula I | 1–10 parts by weight |
| | Soya bean protein | 49–90 parts by weight |
| b) | Active compound of the formula I | 0.5–10 parts by weight |

-continued

| | |
|---|---|
| Benzyl alcohol | 0.08–1.4 parts by weight |
| Hydroxypropyl-methylcellulose | 0–3.5 parts by weight |
| Water | remainder to 100 |

Formulations for use in "medicinal baths" and for pond treatment have, for example, the following composition and preparation.

| | | |
|---|---|---|
| c) | 2.5 g of active compound of the formula (I) are dissolved in 100 ml of triethanolamine, while heating. | |
| d) | 2.5 g of active compound of the formula (I) and | |
| | 12.5 g of lactic acid are dissolved in 100 ml of triethanolamine, while heating and stirring. | |
| e) | 10.0 g of active compound of the formula (I) is dissolved in 100 ml of monoethanolamine. | |
| f) | Active compound of the formula I | 5.0 g |
| | Propylene glycol | 50.0 g |
| | Sodium carbonate | 5.0 g |
| | Water | to 100 ml |
| g) | Active compound of the formula I | 5.0 g |
| | Monoethanolamine | 10 g |
| | N-Methylpyrrolidone | to 100 ml |
| h) | Active compound of the formula I | 2.5 g |
| | Sodium carbonate | 5.0 g |
| | Polyethylene glycol 200 | to 100 ml |

The active compound is dissolved in the polyethylene glycol, while heating, and sodium carbonate is suspended in the solution.

Example A

Coccidiosis in chickens

Chicks 9 to 11 days old were infected with 40000 sporulated oocysts of highly virulent strains of Eimeria acervulina, E. maxima and E. tenella, the pathogens of intestinal coccidiosis.

3 days before infection and 8 days after infection (end of the experiment), the active compound was mixed into the animal feed in the concentration stated.

The number of oocysts in the faeces was determined with the aid of the McMaster chamber (see Engelbrecht and colleagues "Parasitologische Arbeitsmehoden in Medizin und Veterinärmedizin (Parasitological Working Methods in Medicine and Veterinary Medicine)", page 172, Akademie-Verlag, Berlin (1965)).

The active compound doses and excretion of oocysts in % are stated for the individual pathogens in the following table. In this table, 100% means no action and 0% means a full action, that is to say no excretion of oocysts.

TABLE 1

| | | Coccidiosis in chickens | | |
|---|---|---|---|---|
| Example No. | Dose PPM | E. acervulina excretion of oocysts in % in comparison with the untreated infected control | E. maxima excretion of oocysts in % in comparison with the non-infected untreated control | E. tenella |
| untreated infected control | 0 | 100 | 100 | 100 |
| | 50 | 0 | 0 | 0 |

Examples for the preparation of the compounds Ia:

EXAMPLE 1

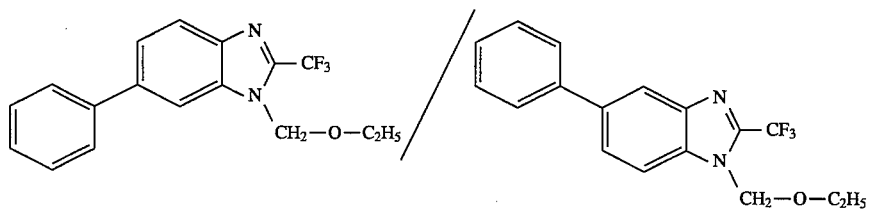

7.9 g (0.03 mol) of 5(6)-phenyl-2-trifluoromethyl-1-H-benzimidazole and 8.2 g (0.06 mol) of powdered potassium carbonate are heated at the reflux temperature in 70 ml of ethyl acetate for 15 minutes, 3.9 g (0.04 mol) of (chloromethyl ethyl ether in 20 ml of ethyl acetate are then added and the mixture is heated at the reflux temperature for a further 4 hours, while stirring. For working up, the cooled reaction mixture is washed twice with 40 ml of water each time, dried over sodium sulphate and concentrated in vacuo, and the residue is purified by chromatography on silica gel (mobile phase: methylene chloride).

6.9 g (71% of theory) of 1-ethoxymethyl-5(6)-phenyl-2-trifluoromethyl-benzimidazole are obtained as a regioisomer mixture in a ratio of 1:1.

$^1$H-NMR (DMSO-$d_6$/tetramethylsilane): d=5.84 (s,2H); 5.89 (s, 2H) ppm [in each case N-$\underline{CH_2}$—O—].

The following substituted benzimidazoles of the general formula (Ia) are obtained in a corresponding manner and in accordance with the general preparation statements:

(Ia)

$$\begin{array}{c}\text{structure: benzimidazole with } X^1, X^2, X^3, X^4 \text{ on benzene ring, } CF_3 \text{ at 2-position, and } N-CH(R^1)-R^2 \end{array}$$

| Ex. No. | $X^1$ | $X^2$ | $X^3$ | $X^4$ | $R^1$ | $R^2$ | physical properties |
|---|---|---|---|---|---|---|---|
| 2 | Br | H | $CF_3$ | H | H | $-N(CH_3)-C(=O)-OCH_3$ | m.p. 90–90° C. |
| 3 | Br | H | $CF_3$ | H | H | $-N(C_2H_5)-C(=O)-OCH_3$ | m.p. 70–74° C. |
| 4 | Br | H | $CF_3$ | H | H | $-N(n\text{-}C_3H_7)-C(=O)-OCH_3$ | m.p. 75–79° C. |
| 5 | Br | H | $CF_3$ | H | H | $-CH=CH_2$ | m.p. 53–56° C. (82:18) |
| 6 | (H) | (CF_3) | (H) | (Br) | H | $-CO-C(CH_3)_3$ | m.p. 120–123° C. |
| 7 | Br | H | $CF_3$ | H | H | $-CH_2-C_6H_5$ | m.p. 80–84° C. |
| 8 | Br | H | $CF_3$ | H | H | $-CO-C_6H_5$ | m.p. 163–166° C. |
| 9 | (H) | (CF_3) | (H) | (Br) | H | $-CH=CH-CH_3$ | m.p. 80–83° C. (93:7) |
| 10 | Br | H | $CF_3$ | H | H | $\sim CH=C(Cl)(CH_3)$ | m.p. 60–63° C. (E/Z = 64:36) |
| 11 | H | $(CH_3)_2N-CO-$ | H $((CH_3)_2N-CO-)$ | H | H | $-O-C_2H_5$ | $^1$H-NMR*): 5.59; 5.60; 7.54–8.62 |

-continued (Ia)

Structure: benzimidazole with X¹, X², X³, X⁴ on benzene ring; 2-position CF₃; N-CH(R¹)(R²)

| Ex. No. | X¹ | X² | X³ | X⁴ | R¹ | R² | physical properties |
|---|---|---|---|---|---|---|---|
| 12 | H | F₂CH—CF₂—O— | H | H | H | —O—C₂H₅ | ¹H-NMR*): 5.94; 6.00 (63:37) |
| 13 | Br | H (CF₃) | (F₂CH—CF₂—O—) CF₃ (H) | H (Br) | H | —O—i-C₃H₇ | m.p. 70–73° C. (76:24) |
| 14 | Br | H (CF₃) | CF₃ (H) | H (Br) | H | —O—n-C₃H₇ | ¹H-NMR*): 5.94; 6.00 (64:36) |
| 15 | Br | H (CF₃) | CF₃ (H) | H (Br) | H | —O—(CH₂)₃—C₆H₅ | m.p. 71–73° C. |
| 16 | Br | H | CF₃ | H | H | —O—CH₂—C≡CH | m.p. 195–200° C. |
| 17 | Br | H | CF₃ | H | H | —O—C(=O)—NH—C(=O)—NH—(4-Cl-C₆H₄) | |
| 18 | Br | H | CF₃ | H | H | —O—CO—C(CH₃)₃ | m.p. 98–101° C. |
| 19 | Br | H (CF₃) | CF₃ (H) | H (Br) | H | —O—CH₂—(3-Cl-C₆H₄) | ¹H-NMR*): 6.08; .14 (70:30) |
| 20 | Br | H (CF₃) | CF₃ (H) | H | H | —O—C₂H₅ | m.p. 82–85° C. (87:13) |
| 21 | Br | H | CF₃ | H | H | —N(CH₃)—C(=O)—OC₂H₅ | m.p. 128–130° C. |
| 22 | Br | H | CF₃ | H | H | CN | |
| 23 | H | C₆H₅—CO— (H) | H (C₆H₅—CO—) | H | H | —O—C₂H₅ | m.p. 147–151° C. ¹H-NMR*): 5.89 |

-continued $$\text{(Ia)}$$

| Ex. No. | X$^1$ | X$^2$ | X$^3$ | X$^4$ | R$^1$ | R$^2$ | physical properties |
|---|---|---|---|---|---|---|---|
| 24 | H | C$_6$H$_5$—CO— (H) | H (C$_6$H$_5$—CO—) | H | H | —N(CH$_3$)—C(=O)—OCH$_3$ | m.p. 105–109° C. (1:1) |
| 25 | H | C$_6$H$_5$—CO— (H) | H (C$_6$H$_5$—CO—) | H | H | CN | m.p. 102–105° C. (1:1) |
| 26 | H | C$_6$H$_5$ (H) | H (C$_6$H$_5$) | H | H | —N(CH$_3$)—C(=O)—OCH$_3$ | $^1$H-NMR*): 6.02; 5.98 (40:60) |
| 27 | Br (H) | H (CF$_3$) | CF$_3$ (H) | H (Br) | H | —O—CH$_2$—CH$_2$—O—CH$_3$ | $^1$H-NMR*): 5.94; 6.03 |
| 28 | Br | H | CF$_3$ | H | H | —N(C$_2$H$_5$)—C(=O)—OC$_2$H$_5$ | m.p. 103–106° C. |
| 29 | Br | H | CF$_3$ | H | H | —N(n-C$_3$H$_7$)—C(=O)—OC$_2$H$_5$ | m.p. 92–94° C. |

-continued (Ia)

[Structure: benzimidazole with X¹, X², X³, X⁴ on benzene ring; 2-position CF₃; N-CH(R¹)-R²]

| Ex. No. | X¹ | X² | X³ | X⁴ | R¹ | R² | physical properties |
|---|---|---|---|---|---|---|---|
| 30 | Br | H | CF₃ | H | H | -N(i-C₃H₇)-C(O)-OC₂H₅ | m.p. 70–73° C. |
| 31 | Br | H | CF₃ | H | H | -N(CH₂-C₆H₅)-C(O)-OC₂H₅ | m.p. 70–74° C. |
| 32 | Br | H | CF₃ | H | H | -N(C₂H₅)-C(O)-O-i-C₄H₉ | m.p. 70–73° C. |
| 33 | H | -O-(CH₂)₃-O- | | H | H | -O-C₂H₅ | m.p. 70–74° C. |
| 34 | Br | H | CF₃ | H | H | -N(CH₃)₂ | (x HCl) m.p. 105–108° C. |
| 35 | H | -O-(CH₂)₃-O- | | H | H | -N(CH₃)-C(O)-OCH₃ | |
| 36 | Br | H | CF₃ | H | H | -N(c-C₆H₁₁)-C(O)-OC₂H₅ | m.p. 80–83° C. |

-continued (Ia)

[Structure: benzimidazole with X¹, X², X³, X⁴ on benzene ring, 2-CF₃, N-CH(R¹)(R²)]

| Ex. No. | X¹ | X² | X³ | X⁴ | R¹ | R² | physical properties |
|---|---|---|---|---|---|---|---|
| 37 | Br | H | CF₃ | H | H | $-\underset{\underset{S}{\parallel}}{N}(C_6H_5)-C-OC_2H_5$ | m.p. 135–136° C. |
| 38 | Br | H | CF₃ | H | H | $-\underset{\underset{O}{\parallel}}{N}(CH_2-CH=CH_2)-C-OC_2H_5$ | m.p. 76–78° C. |
| 39 | Br | H | CF₃ | H | H | $-\underset{\underset{S}{\parallel}}{N}(C_6H_5)-C-OC_2H_5$ | m.p. 174–176° C. |
| 40 | Br | H | CF₃ | H | H | $-\underset{\underset{O}{\parallel}}{N}(CH_2-CH(CH_3)_2)-C-OC_2H_5$ | m.p. 109–112° C. |
| 41 | Br (H) | H (CF₃) | CF₃ (H) | H (Br) | H | $-S-CH_3$ | m.p. 56–60° C. (1:1) |
| 42 | H | CF₃ (Cl) | Cl (CF₃) | H | H | $-COOC_2H_5$ | |
| 43 | H | CF₃ | Cl | H | H | [2-chlorophenyl group] | |

-continued (Ia)

[Structure: benzimidazole with X¹, X², X³, X⁴ substituents on benzene ring; 2-position has CF₃; N1 has CH(R¹)-R²]

| Ex. No. | X¹ | X² | X³ | X⁴ | R¹ | R² | physical properties |
|---|---|---|---|---|---|---|---|
| 44 | H | Cl | CF₃ | H | H | 2-Cl-6-methylphenyl | |
| 45 | H | CF₃ | Cl | H | H | 2,4-diCl-6-methylphenyl | |
| 46 | H | Cl | CF₃ | H | H | 2,4-diCl-6-methylphenyl | |
| 47 | H | CF₃ (Cl) | Cl (CF₃) | H | H | 4-NO₂-2-methylphenyl | |
| 48 | H | CF₃ (Cl) | Cl (CF₃) | H | H | -P(=O)(OC₂H₅)(OC₂H₅) | |
| 49 | H | CF₃ (Cl) | Cl (CF₃) | H | H | 3-CF₃-5-methylphenyl | |

-continued
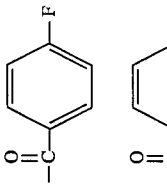
(Ia)
| Ex. No. | X¹ | X² | X³ | X⁴ | R¹ | R² | physical properties |
|---|---|---|---|---|---|---|---|
| 50 | H | CF₃ (Cl) | Cl (CF₃) | H | —O—C₂H₅ | —O—C₂H₅ | m.p. 90–92° C. |
| 51 | H | CF₃ (Cl) | Cl (CF₃) | H | H | —CO—C(CH₃)₃ | |
| 52 | H | CF₃ (Cl) | Cl (CF₃) | H | H | CN | |
| 53 | H | CF₃ (Cl) | CF₃ (Cl) | H | H | CN | |
| 54 | H | CF₃ (Cl) | Cl (CF₃) | H | H | —CO—NH₂ | |
| 55 | H | CF₃ (Cl) | Cl (CF₃) | H | H | —CO—C₆H₅ | |
| 56 | H | CF₃ (Cl) | Cl (CF₃) | H | H | —OCH(CH₃)₂ | ¹H-NMR*): A: 5.66; 7.83; 8.23 B: 5.71; 8.00; 8.06 |
| 57 | H | CF₃ (Cl) | Cl (CF₃) | H | H | 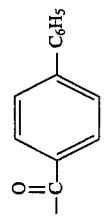 | ¹H-NMR*): A: 5.67; 7.43; 8.33 B: 5.73; 7.63; 8.10 |
| 58 | H | CF₃ (Cl) | Cl (CF₃) | H | H | 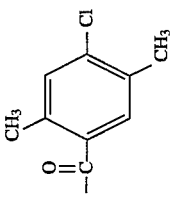 | ¹H-NMR*): A: 5.75; 7.45; 8.30 B: 5.78; 7.75; 7.97 |
| 59 | H | CF₃ (Cl) | Cl (CF₃) | H | H | (2,5-dimethyl-4-chlorobenzoyl) | ¹H-NMR*): A: 5.60; 7.41; 8.28 B: 5.63; 7.63; 8.06 |

-continued (Ia)

[Structure: benzimidazole with X¹, X², X³, X⁴ substituents on the benzene ring; N-CH(R¹)-R² and 2-CF₃ on the imidazole]

| Ex. No. | X¹ | X² | X³ | X⁴ | R¹ | R² | physical properties |
|---|---|---|---|---|---|---|---|
| 60 | H | CF₃ (Cl) | Cl (CF₃) | H | H | (2,4-dichlorobenzoyl) -C(=O)-C₆H₃Cl₂-2,4 | ¹H-NMR*): A: 5.71; 7.42; 8.28 B: 5.75; 7.66; 8.06 |
| 61 | H | CF₃ (Cl) | Cl (CF₃) | H | H | (3,5-dichlorobenzoyl) -C(=O)-C₆H₃Cl₂-3,5 | ¹H-NMR*): A: 5.67; 7.39; 8.29 B: 5.73, 7.60 and 8.05 |
| 62 | H | CF₃ (Cl) | Cl (CF₃) | H | H | (4-bromobenzoyl) -C(=O)-C₆H₄Br-4 | ¹H-NMR*): A: 5.83; 7.68; 8.25 B: 5.90; 7.75; 8.03 |
| 63 | H | CF₃ (Cl) | Cl (CF₃) | H | H | (4-chloro-2-methylbenzoyl) -C(=O)-C₆H₃(CH₃)(Cl) | ¹H-NMR*): A: 5.60; 7.38; 8.26 B: 5.64, 7.62 and 8.04 |
| 64 | H | CF₃ (Cl) | Cl (CF₃) | H | H | (2,3-dichlorophenylacetyl) -C(=O)-CH₂-C₆H₃Cl₂-2,3 | ¹H-NMR*): A: 5.30; 7.54; 8.22 B: 5.35; 7.75; 8.02 |

-continued $$\text{(Ia)}$$

Structure: benzimidazole with X¹, X², X³, X⁴ on the benzene ring; 2-position has CF₃; N-substituent is –CH(R¹)–R²

| Ex. No. | X¹ | X² | X³ | X⁴ | R¹ | R² | physical properties |
|---|---|---|---|---|---|---|---|
| 65 | H | CF₃ (Cl) | Cl (CF₃) | H | H | –CH₂–C₆H₃(3,4-Cl₂) (3,4-dichlorobenzyl: –CH₂– attached to phenyl with Cl at 3 and 4) | ¹H-NMR*): A: 5.11; 7.15; 8.23 B: 5.15; 7.40; 8.02 |
| 66 | H | CF₃ (Cl) | Cl (CF₃) | H | CH₃ | CN | ¹H-NMR*): A: 5.60; 7.80; 8.34 B: 5.65; 7.96; 8.13 |
| 67 | H | CF₃ (Cl) | Cl (CF₃) | H | H | –N(C₂H₅)–C(=O)–OCH₃ | ¹H-NMR*): A: 5.86; 7.98; 8.33 B: 5.90; 8.03; 8.21 |
| 68 | H | CF₃ (Cl) | Cl (CF₃) | H | H | –N(n-C₄H₉)–C(=O)–OC₂H₅ | ¹H-NMR*): A: 5.85; 7.99; 8.32 B: 5.90; 8.02; 8.22 |
| 69 | H | CF₃ (Cl) | Cl (CF₃) | H | H | –N(CH₃)–C(=O)–OCH₃ | ¹H-NMR*): A: 5.87; 7.98; 8.34 B: 5.91; 8.05; 8.22 |
| 70 | H | –O–CF₂–CF₂–O– | | H | H | –O–CH(CH₃)₂ | ¹H-NMR*): 5.61; 7.45; 7.65 |
| 71 | H | –O–CF₂–CF₂–O– | | H | H | –CO–C₆H₅ | m.p. 141–143° C. |
| 72 | H | –O–CF₂–CF₂–O– | | H | H | CN | m.p. 132–134° C. |
| 73 | H | –O–CF₂–CF₂–O– | | H | H | –O–CH(CH₃)₂ | m.p. 76–78° C. |

-continued (Ia)

Structure: benzimidazole with X¹, X², X³, X⁴ on benzene ring; 2-position has CF₃; N1 has CH(R¹)-CH-R² substituent.

| Ex. No. | X¹ | X² | X³ | X⁴ | R¹ | R² | physical properties |
|---|---|---|---|---|---|---|---|
| 74 | H | CF₃ | —O—CF₂—O— | H | H | —CO—C₆H₅ | m.p. 188–189° C. |
| 75 | H | (Br) | —O—CF₂—O— | H | H | CN | m.p. 145–147° C. |
| 76 | H |  | Br (CF₃) | H | H | —O—CH(CH₃)₂ | ¹H-NMR*): A: 5.65; 8.03; B: 5.69; 8.05; 8.23 8.20 |
| 77 | H | CF₃ (Br) | Br (CF₃) | H | H | 2,4-dichlorophenyl | ¹H-NMR*): A: 5.56; 7.59; 8.29 B: 5.59; 7.61; 8.26 |
| 78 | H | CF₃ (H) | H (CF₃) | H | H | —O—C₂H₅ | ¹H-NMR*): A: 5.38; 7.18–7.94; B: 5.40 |
| 79 | H | CF₃ (H) | H (CF₃) | H | H | OH | ¹H-NMR*): 2.2; 7.76; 8.1 |
| 80 | H | CF₃ (Br) | Br (CF₃) | H | H | —O—C₂H₅ | ¹H-NMR*): A: 5.64; 8.03; B: 5.72; 8.06; 8.21 8.18 |
| 81 | H | CF₃ | Br | H | H | —O—C₂H₅ | m.p. 66° C. |
| 82 | H | Br | CF₃ | H | H | —O—C₂H₅ | ¹H-NMR*): B: 5.72; 8.05; 8.17 |
| 83 | H | CF₃ (Br) | Br (CF₃) | H | H | —O-n-C₃H₇ | ¹H-NMR*): A: 6.67; 8.08; B: 5.69; 8.11; 8.27 8.25 |
| 84 | H | (Br) | Br (CF₃) | H | H | —O—CH₂—C≡CH | ¹H-NMR*): A: 5.51; 7.89; |

-continued (Ia)

structure: benzimidazole with X¹, X², X³, X⁴ substituents and N-CH(R¹)-R² group, 2-CF₃

| Ex. No. | X¹ | X² | X³ | X⁴ | R¹ | R² | physical properties |
|---|---|---|---|---|---|---|---|
| 85 | H | CF₃ (Cl) | Cl (CF₃) | H | H | —O—C₂H₅ | 8.17 B: 5.71; 7.93; 8.21 ¹H-NMR*): A: 5.69; 7.82; 8.23 B: 5.71; 8.00; 8.03 |
| 86 | H | CF₃ | Cl | H | H | —O—C₂H₅ | m.p. 73° C. |
| 87 | H | Cl | CF₃ | H | H | —O—C₂H₅ | ¹H-NMR*): B: 5.71; 8.00; 8.03 |
| 88 | H | CF₃ (Cl) | Cl (CF₃) | H | H | —O—CH(CH₂F)₂ | ¹H-NMR*): A: 5.83; 7.78; 8.03 B: 5.89; 8.01; 8.26 |
| 89 | H | CF₃ (Cl) | Cl (CF₃) | H | H | —O-n-C₃H₇ | ¹H-NMR*): A: 5.70; 7.80; 8.06 B: 5.73; 7.99; 8.21 |
| 90 | H | CF₃ (Cl) | Cl (CF₃) | H | H | —O—CH₂—C≡CH | ¹H-NMR*): A: 5.73; 7.81; 8.04 B: 5.77; 8.00; 8.02 |
| 91 | H | CF₃ (Cl) | Cl (CF₃) | H | H | —N(CH₃)—C(=O)—OC₂H₅ | ¹H-NMR*): A: 5.90; 8.00; 8.21 B: 5.93; 8.03; 8.31 |

-continued (Ia)

[Structure: benzimidazole with X¹, X², X³, X⁴ substituents, 2-CF₃, N-CH(R¹)-R²]

| Ex. No. | X¹ | X² | X³ | X⁴ | R¹ | R² | physical properties |
|---|---|---|---|---|---|---|---|
| 92 | H | CF₃ (Cl) | Cl (CF₃) | H | H | −N(C₂H₅)−C(=O)−OC₂H₅ | ¹H-NMR*): A: 5.89; 8.00; 8.21 B: 5.95; 8.03; 8.33 |
| 93 | H | CF₃ (Cl) | Cl (CF₃) | H | H | −N(n-C₃H₇)−C(=O)−OC₂H₅ | ¹H-NMR*): A: 5.89; 8.00; 8.22 B: 5.91; 8.04; 8.32 |
| 94 | H | CF₃ (Cl) | Cl (CF₃) | H | H | −CO−OC₂H₅ | m.p. 73° C. |
| 95 | H | CF₃ (Cl) | Cl (CF₃) | H | CH₃ | −CO−OC₂H₅ | ¹H-NMR*): A: 1.91; 5.34; 7.57; 8.12 |
| 96 | H | −O−CF₂−O− | | H | H | −O−C₂H₅ | m.p. 92° C. |
| 97 | H | −O−CF₂−O− | | H | H | −O−CH(CH₂F)₂ | m.p. 64° C. |
| 98 | H | −O−CF₂−O− | | H | H | −O−n-C₃H₇ | m.p. 41° C. |
| 99 | H | −O−CF₂−O− | | H | H | −O−CH₂C≡CH | m.p. 87° C. |
| 100 | H | −O−CF₂−O− | | H | H | −N(CH₃)−C(=O)−OC₂H₅ | m.p. 93° C. |
| 101 | H | −O−CF₂−O− | | H | H | −N(C₂H₅)−C(=O)−OC₂H₅ | m.p. 67° C. |

-continued (Ia)

Structure: benzimidazole with substituents $X^1, X^2, X^3, X^4$ on benzene ring; at the 2-position $CF_3$; at N: $CH(R^1)(R^2)$.

| Ex. No. | $X^1$ | $X^2$ | $X^3$ | $X^4$ | $R^1$ | $R^2$ | physical properties |
|---|---|---|---|---|---|---|---|
| 102 | H | | $-O-CF_2-O-$ | H | H | $-N(n-C_3H_7)-C(=O)-OC_2H_5$ | $^1$H-NMR*): 5.89; 7.51 |
| 103 | H | | $-O-CF_2-CF_2-O-$ | H | H | $-O-C_2H_5$ | $^1$H-NMR*): 5.63; 7.52; 7.63 |
| 104 | H | | $-O-CF_2-CF_2-O-$ | H | H | $-O-CH(CH_2F)_2$ | $^1$H-NMR*): 5.82; 7.42; 7.68 |
| 105 | H | | $-O-CF_2-CF_2-O-$ | H | H | $-N(CH_3)-C(=O)-OC_2H_5$ | m.p. 118° C. |
| 106 | H | | $-O-CF_2-CF_2-O-$ | H | H | $-N(C_2H_5)-C(=O)-OC_2H_5$ | m.p. 85° C. |
| 107 | H | | $-O-CF_2-CF_2-O-$ | H | H | $-N(n-C_3H_7)-C(=O)-OC_2H_5$ | m.p. 103° C. |
| 108 | H | | $-O-CF_2-CF_2-O-$ | H | H | $-O-n-C_3H_7$ | $^1$H-NMR*): 5.75; 7.48; 7.54 |
| 109 | H | | $-O-CF_2-CF_2-O-$ | H | H | $-O-CH_2-C\equiv CH$ | $^1$H-NMR*): 5.81; 7.49; 7.68 |
| 110 | H | | $-O-CF_2-CF_2-O-$ | H | H | $-CO-OC_2H_5$ | m.p. 90° C. |

(1a)

$$\text{structure: benzimidazole with } X^1, X^2, X^3, X^4 \text{ substituents, } CF_3 \text{ at 2-position, and } N-CH(R^1)-R^2$$

| Ex. No. | $X^1$ | $X^2$ | $X^3$ | $X^4$ | $R^1$ | $R^2$ | physical properties |
|---|---|---|---|---|---|---|---|
| 111 | H | | —O—CF$_2$—CF$_2$—O— | H | CH$_3$ | —CO—OC$_2$H$_5$ | ¹H-NMR*): 5.84; 5.34; 7.65 |
| 112 | H | | —O—CF$_2$—CHF—O— (—O—CHF—CF$_2$—O—) | H | H | —O—C$_2$H$_5$ | ¹H-NMR*): 5.84; 7.64; 7.71 |
| 113 | H | | —O—CF$_2$—CHF—O— (—O—CHF—CF$_2$—O—) | H | H | —O—CH(CH$_2$F)$_2$ | ¹H-NMR*): 5.81; 6.01; 7.35; 7.61 |
| 114 | H | | —O—CF$_2$—CHF—O— (—O—CHF—CF$_2$—O—) | H | H | —O-n-C$_3$H$_7$ | ¹H-NMR*): 5.70; 6.03; 7.50; 7.60 |
| 115 | H | | —O—CF$_2$—CHF—O— (—O—CHF—CF$_2$—O—) | H | H | —O—CH$_2$—C≡CH | ¹H-NMR*): 5.56; 6.00; 7.46; 7.54 |
| 116 | H | | —O—CF$_2$—CHF—O— (—O—CHF—CF$_2$—O—) | H | H | CH$_3$-N(-)-C(=O)-OC$_2$H$_5$ | ¹H-NMR*): 5.78; 6.01; 7.43; 7.57 |
| 117 | H | | —O—CF$_2$—CHF—O— (—O—CHF—CF$_2$—O—) | H | H | C$_2$H$_5$-N(-)-C(=O)-OC$_2$H$_5$ | ¹H-NMR*): 5.80; 6.00; 7.45; 7.48 |
| 118 | H | | —O—CF$_2$—CHF—O— (—O—CHF—CF$_2$—O—) | H | H | n-C$_3$H$_7$-N(-)-C(=O)-OC$_2$H$_5$ | ¹H-NMR*): 5.85; 6.05; 7.53–7.68 |
| 119 | H | | —O—CF$_2$—CHF—O— (—O—CHF—CF$_2$—O—) | H | H | —CO—OC$_2$H$_5$ | ¹H-NMR*): 4.98; 6.03; 7.09; 7.63 |

-continued (Ia)

structure: benzimidazole with X¹, X², X³, X⁴ on benzene ring; 2-CF₃; N-CH(R¹)(R²)

| Ex. No. | X¹ | X² | X³ | X⁴ | R¹ | R² | physical properties |
|---|---|---|---|---|---|---|---|
| 120 | H | —O—CF₂—CHF—O— (—O—CCHF—CF₂—O—) | | H | CH₃ | —CO—OC₂H₅ | ¹H-NMR*): 1.86; 6.01; 7.19; 7.62 |
| 121 | H | —O—CF₂—CCIF—O— (—O—CCIF—CF₂—O—) | | H | H | —O—C₂H₅ | ¹H-NMR*): 2.35; 7.15–7.98 |
| 122 | H | —O—CF₂—CCIF—O— (—O—CCIF—CF₂—O—) | | H | H | —O-n-C₃H₇ | |
| 123 | H | —O—CF₂—CCIF—O— (—O—CCIF—CF₂—O—) | | H | H | —O—CH₂—C≡CH | |
| 124 | H | —O—C(CF₃)(CH₂—CF₃)—O— | | H | H | —O—C₂H₅ | ¹H-NMR*): 5.62; 7.28; 7.32 |
| 125 | H | —O—C(CF₃)(CH₂—CF₃)—O— | | H | H | —N(CH₃)—C(O)—OC₂H₅ | ¹H-NMR*): A: 5.78; 7.32; 7.44  B: 5.80; 7.32; 7.44 |
| 126 | H | —O—C(CF₃)(CH₂—CF₃)—O— | | H | H | —N(C₂H₅)—C(O)—OC₂H₅ | ¹H-NMR*): A: 5.76; 7.30; 7.42  B: 5.78; 7.30; 7.42 |
| 127 | H | —O—C(CF₃)(CH₂—CF₃)—O— | | H | H | —N(n-C₃H₇)—C(O)—OC₂H₅ | ¹H-NMR*): A: 5.76; 7.32; 7.42  B: 5.78; 7.32; 7.42 |
| 128 | H | CF₃O (H) | H (CF₃O) | H | H | —O—C₂H₅ | |

-continued (Ia)

[Structure: benzimidazole with X¹, X², X³, X⁴ substituents on benzene ring; 2-position has CF₃; N-substituent is CH(R¹)-R²]

| Ex. No. | X¹ | X² | X³ | X⁴ | R¹ | R² | physical properties |
|---|---|---|---|---|---|---|---|
| 129 | H | CF₃O | CF₃O | H | H | —O—C₂H₅ | ¹H-NMR*): 5.50; 7.78; 7.82 |
| 130 | H | CF₃O | CF₃O | H | H | —O-n-C₃H₇ | ¹H-NMR*): 5.51; 7.75; 7.79 |
| 131 | H | CF₃O | CF₃O | H | H | —O—CH₂—C≡CH | ¹H-NMR*): 5.48; 7.76; 7.80 |
| 132 | H | CF₃O | CF₃O | H | H | —O—CH(CH₂F)₂ | ¹H-NMR*): 5.80; 7.78; 7.84 |
| 133 | H | CH₃—SO₂— (H) | H (CH₃—SO₂—) | CF₃ (H) | H | —O—C₂H₅ | ¹H-NMR*): 5.80; 8.25; 8.56 |
| 134 | H (CF₃) | CF₃ (CH₃O) | (CH₃O) CF₃ | H | H | —O—C₂H₅ | ¹H-NMR*): A: 5.49; 7.05; 7.70 B: 5.50; 7.10; 7.73 |
| 135 | H | (C₂H₅)₂N—CO— (H) | H ((C₂H₅)₂N—CO—) | H | H | —O—C₂H₅ | ¹H-NMR*): 5.73; 5.74; 7.29–8.63 |
| 136 | H | C₂H₅O—CO— (H) | H (C₂H₅O—CO—) | H | H | —O—C₂H₅ | ¹H-NMR*): 5.72; 5.74; 7.65–8.59 |
| 137 | H | C₆H₅—CO—NH— (H) | H (C₆H₅—CO—NH—) | H | H | —O—C₂H₅ | ¹H-NMR*): 5.70; 7.21–8.48; 7.98 |
| 138 | H | CH₃O—CO— (H) | H (CH₃O—CO—) | H | H | —O—C₂H₅ | ¹H-NMR*): 5.72; 5.74; 7.68–8.59 |

The following substituted benzimidazoles of the general formula (Ia-1) are furthermore obtained in a corresponding manner $$\text{(Ia-1)}$$

Structure: benzimidazole with $X^2$ and $X^3$ substituents, $CF_3$ at position 2, and $N-CH_2-O-C_2H_5$ group.

| Ex. No. | $X^2$ | $X^3$ | physical properties |
|---|---|---|---|
| 139 | 4-Cl-C$_6$H$_4$-CH$_2$-SO$_2$-N(CH$_2$-OC$_2$H$_5$)- (H) | H (4-Cl-C$_6$H$_4$-CH$_2$-SO$_3$-N(CH$_2$-OC$_2$H$_5$)-) | $^1$H-NMR*): 5.69; 5.70; 7.03–8.05 |
| 140 | C$_6$H$_5$-CH$_2$-SO$_2$-NH- (H) | H (C$_6$H$_5$-CH$_2$-SO$_2$-NH-) | $^1$H-NMR*): 5.65; 5.67; 6.71–8.03 |
| 141 | C$_6$H$_5$-SO$_2$-NH- (H) | H (C$_6$H$_5$-SO$_2$-NH-) | |
| 142 | 2-Cl-C$_6$H$_4$-SO$_2$-NH- (H) | H (2-Cl-C$_6$H$_4$-SO$_2$-NH-) | $^1$H-NMR*): 5.32; 5.63; 7.15–8.46 |
| 143 | 2-CF$_3$-C$_6$H$_4$-SO$_2$-NH- (H) | H (2-CF$_3$-C$_6$H$_4$-SO$_2$-NH-) | $^1$H-NMR*): 5.18; 5.63; 6.95–8.40 |
| 144 | (CH$_3$)$_3$C-CH$_2$-O-C(O)- (H) | H ((CH$_3$)$_3$C-CH$_2$-O-C(O)-) | $^1$H-NMR*): 5.81; 5.82; 7.65–8.62 |
| 145 | 2,4-Cl$_2$-C$_6$H$_3$-NH-C(O)-NH- (H) | H (2,4-Cl$_2$-C$_6$H$_3$-NH-C(O)-NH-) | $^1$H-NMR*): 5.58; 5.62; 6.78–8.15 |
| 146 | [F$_3$C-CH$_2$/F$_3$C-C(O)(O)]-C$_6$H$_3$-NH-C(O)-NH- (H) | H ([F$_3$C-CH$_2$/F$_3$C-C(O)(O)]-C$_6$H$_3$-NH-C(O)-NH-) | $^1$H-NMR*): 5.53; 6.45–8.07 |
| 147 | 3-Cl-4-(C$_2$H$_5$O-(CH$_2$)$_2$-O)-C$_6$H$_3$-NH-C(O)-NH- (H) | H (3-Cl-4-(C$_2$H$_5$O-(CH$_2$)$_2$-O)-C$_6$H$_3$-NH-C(O)-NH-) | $^1$H-NMR*): 5.51; 5.54; 6.71–8.01 |

-continued (Ia-1)

$$\text{benzimidazole with } X^2, X^3 \text{ substituents, 2-CF}_3, \text{N-CH}_2\text{-O-C}_2\text{H}_5$$

| Ex. No. | $X^2$ | $X^3$ | physical properties |
|---|---|---|---|
| 148 | Cl-substituted phenyl with n-C$_3$H$_7$O—(CH$_2$)$_2$— and —NH—C(O)—NH— (H) | (H isomer: n-C$_3$H$_7$O—(CH$_2$)$_2$— Cl-phenyl —NH—C(O)—NH—) | |
| 149 | C$_2$H$_5$O—(CH$_2$)$_2$—O—C$_6$H$_4$—NH—C(O)—NH— (H) | (H; C$_2$H$_5$O—(CH$_2$)$_2$—O—C$_6$H$_4$—NH—C(O)—NH—) | $^1$H-NMR*): 5.54; 5.58; 6.72–8.08 |
| 150 | i-C$_3$H$_7$O—(CH$_2$)$_2$—O—C$_6$H$_4$—NH—C(O)—NH— (H) | (H; i-C$_3$H$_7$O—(CH$_2$)$_2$—O—C$_6$H$_4$—NH—C(O)—NH—) | $^1$H-NMR*): 5.49; 5.53; 6.61–8.11 |

*)The $^1$H-NMR spectra were recorded in deuterochloroform (CDCl$_3$) or hexadeutero-dimethyl sulphoxide (DMSO-d$_6$) with tetramethylsilane (TMS) as the internal standard. The chemical shift is stated as the δ value in ppm.

Preparation of the starting compound for the compounds Ia:

Example II-1:

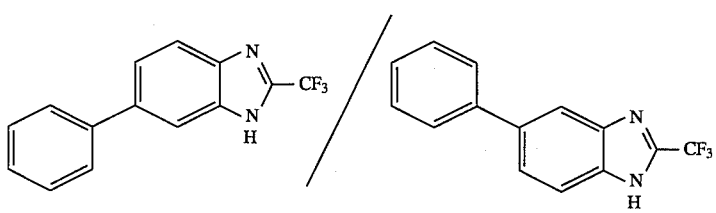

18.4 g (0.092 mol) of 3,4-diaminobiphenyl are heated at the reflux temperature with 150 ml of trifluoroacetic acid for 5 hours. Excess trifluoroacetic acid is then distilled off, the residue is partitioned between 200 ml of ethyl acetate and 70 ml of water, the organic phase is separated off, washed with in each case 70 ml of saturated aqueous sodium bicarbonate solution and water, dried over sodium sulphate and concentrated in vacuo, and the residue is purified by chromatography over silica gel (mobile phase: cyclohexane/ethyl acetate 2:1).

18.3 g (76% of theory) of 5(6)-phenyl-2-trifluoromethyl-1H-benzimidazole are obtained as a 1:1 regioisomer mixture of melting point 177°–182° C.

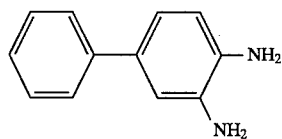

88 g (0.4 mol) of 4-amino-3-nitro-biphenyl (92 percent pure) are hydrogenated with molecular hydrogen in 3,000 ml of methanol in the presence of 10 g of Raney nickel at 60° C. under a pressure of 5 bar. For working up, the Raney nickel is filtered off and the filtrate is concentrated in vacuo.

69.2 g (86% of theory) of 3,4-diaminobiphenyl of melting point 96°–99° C. (purity according to high pressure liquid chromatography 92%) are obtained.

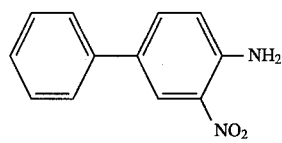

43 g (0.15 mol) of 4-acetamido-3-nitro-biphenyl (90 percent pure) are heated at the reflux temperature together with 1.6 g (0.03 mol) of sodium methylate in 500 ml of methanol for 2 hours. For working up, the cooled reaction mixture is poured into 1,300 ml of ice-water, the mixture is stirred for 10 minutes, and the precipitate which has separated out is then filtered off with suction and dried.

33 g (94% of theory) of 4-amino-3-nitro-biphenyl of melting point 163°–165° C. (purity according to high pressure liquid chromatography 92%) are obtained.

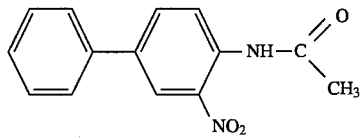

A mixture of 50.4 ml (1.2 mol) of 98 percent strength nitric acid and 60 ml of glacial acetic acid is added dropwise to a suspension of 84.4 g ( 0.4 tool ) of 4-acetamido-biphenyl (compare, for example, Beilstein Volume 12, 4th supplement, page 3248) in 340 ml of glacial acetic acid at 70° C., while stirring, and, when the addition has ended, the mixture is stirred at 70° C. for a further hour. For working up, the cooled reaction mixture is poured into 1.00 ml of ice-water, the mixture is stirred for 10 minutes, and the precipitate which has separated out is filtered off with suction, washed with 200 ml of water and dried.

100 g (88% of theory) of 4-acetamido-3-nitro-biphenyl of melting point 128°–31° C. (purity according to high pressure liquid chromatography 90%) are obtained.

The following 1H-benzimidazoles of the formula

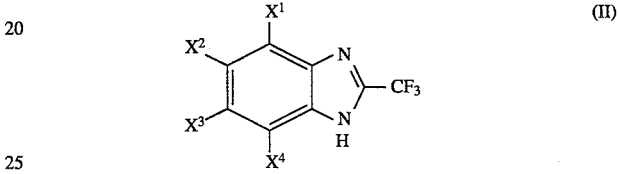

are obtained in a corresponding manner.

-continued

| Ex. No. | X¹ | X² | X³ | X⁴ | Physical Properties |
|---|---|---|---|---|---|
| II-27 | H | (H) | (C₆H₅—SO₂—NH—) | H | m.p. 67° C. |
| II-28 | H | (2-Cl-C₆H₄-SO₂-NH-) | (2-Cl-C₆H₄-SO₂-NH-) | H | m.p. 79° C. |
| II-29 | H | (2-CF₃-C₆H₄-SO₂-NH-) (H) | (2-CF₃-C₆H₄-SO₂-NH-) H | H | m.p. 214–215° C. |
| II-30 | H | 2,4-Cl₂-C₆H₃-NH-C(O)-NH- | ((CH₃)₃C—CH₂—O—C(=O)—) H | H | m.p. 254–255° C. |

-continued

| Ex. No. | X¹ | X² | X³ | X⁴ | Physical Properties |
|---|---|---|---|---|---|
| II-31 | H | (H) 3,4-(OCH(CF₃)₂O)-C₆H₃-NHC(O)NH- | H | H | m.p. 103° C. |
| II-32 | H | (H) 3-Cl-4-(C₂H₅O(CH₂)₂O)-C₆H₃-NHC(O)NH- | H | H | m.p. 186° C. |
| II-33 | H | (H) 3-Cl-4-(n-C₃H₇O(CH₂)₂O)-C₆H₃-NHC(O)NH- | H | H | m.p. 144° C. |

-continued

| Ex. No. | $X^1$ | $X^2$ | $X^3$ | $X^4$ | Physical Properties |
|---|---|---|---|---|---|
| II-34 | H | (H) / C₂H₅O—(CH₂)₂—O—C₆H₄—NH—C(=O)—NH— | (n-C₃H₇O—(CH₂)₂—O—C₆H₃(Cl)—NH—C(=O)—NH—) | H | m.p. 207° C. |
| II-35 | H | (H) / i-C₃H₇O—(CH₂)₂—O—C₆H₄—NH—C(=O)—NH— | (C₂H₅O—(CH₂)₂—O—C₆H₄—NH—C(=O)—NH—) | H | m.p. 201° C. |
| II-36 | H | (H) / 4-Cl-C₆H₄-CH₂-SO₂-N(CH₂-OC₂H₅)— | (i-C₃H₇O—(CH₂)₂—O—C₆H₄—NH—C(=O)—NH—) | H | m.p. 80° C. |
| II-37 | H | (CF₃)₂N— / (H) | (4-Cl-C₆H₄-CH₂-SO₂-N(CH₂-OC₂H₅)—) ((CF₃)₂N—) / H | H | |
| II-38 | H | C₆H₅-CH₂-SO₂-NH— | H | H | m.p. 68° C. |

-continued
| Ex. No. | $X^1$ | $X^2$ | $X^3$ | $X^4$ | Physical Properties |
|---|---|---|---|---|---|
| II-39 | H | (H) |  —CH$_2$—SO$_2$—NH— | H | m.p. 174° C. |
| II-40 | H | CF$_3$S (H) | H (CF$_3$S) | H | m.p. 57° C. |
| II-41 | H | FClCH—CF$_2$—O— (H) | H (FClCH—CF$_2$—O—) | H | m.p. 176° C. |
| II-42 | H | 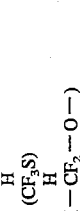 (H) | 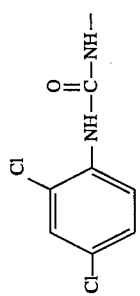 | H | |
| II-43 | H | 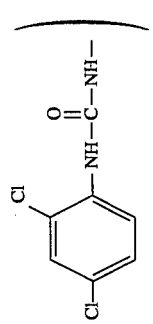 (H) | 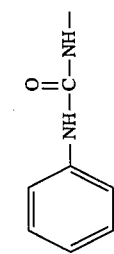 | H | m.p. 190° C. |
| II-44 | H | 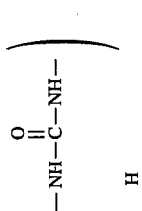 | H | H | m.p. 208° C. |

-continued

| Ex. No. | X¹ | X² | X³ | X⁴ | Physical Properties |
|---|---|---|---|---|---|
| II-45 | H | (H) | (CH₃O—(CH₂)₂—O—⟨C₆H₄⟩—NH—C(=O)—NH—) | H | m.p. 162° C. |
| II-46 | H | (CH₃)₃C—O—CO— (H) | H ((CH₃)₃C—O—CO—) | H | m.p. 70° C. |
| II-47 | H | (2-COOCH₃-C₆H₄-SO₂—NH—) (H) | (2-COOCH₃-C₆H₄-SO₂—NH—) H | H | |
| II-47 | H | (2-Cl-C₆H₄-NH—C(=O)—NH—) (H) | (2-Cl-C₆H₄-NH—C(=O)—NH—) H | H | |
| II-48 | H | (4-O₂N-C₆H₄-C(=O)—NH—) (H) | (4-O₂N-C₆H₄-C(=O)—NH—) H | H | m.p. 61° C. |

-continued

| Ex. No. | X$^1$ | X$^2$ | X$^3$ | X$^4$ | Physical Properties |
|---|---|---|---|---|---|
| II-49 | H | 2-Cl-C$_6$H$_4$-C(O)-NH- (H) | H | H | m.p. 76° C. |
| II-50 | H | CH$_3$O-CO-N(CH$_3$)-SO$_2$-NH- (H) | (CH$_3$O-CO-N(CH$_3$)-SO$_2$-NH-  2-Cl-C$_6$H$_4$-C(O)-NH-) | H | |
| II-51 | H | COOH (H) | H (COOH) | H | m.p. 250° C. |
| II-52 | H | (CH$_3$)$_3$C-NH-CO- (H) | H | H | m.p. 79° C. |
| II-53 | H | F$_3$C-C(CH$_3$)$_2$-NH-C(O)- (H) | H | H | m.p. 39° C. |
| II-54 | H | NC-CH$_2$- (H) | (F$_3$C-C(CH$_3$)$_2$-NH-C(O)- H NC-CH$_2$-) | H | |
| II-55 | H | NH$_2$ (H) | H (NH$_2$) | H | |
| II-56 | H | HOOC-CH$_2$- (H) | H (COOC-CH$_2$-) | H | |
| II-57 | H | F$_3$C-SO$_2$- (H) | H (F$_3$C-SO$_2$-) | H | |

*The $^1$H-NMR spectra were recorded in deuterochloroform (CDCl$_3$) or hexadeutero-dimethyl sulphoxide (DMSO-d$_6$) with tetramethylsilane (TMS) as the internal standard. The chemical shift is stated as the δ value in ppm.

Examples for the preparation of the compounds Ib:

Example Ib-1

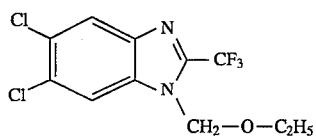

A solution of 14.1 g (0.15 mol) of chloromethyl ethyl ether in 40 ml of ethyl acetate is added dropwise to a mixture of 36 g (0.12 mol) of 5,6-dichloro-2-trifluoromethyl-1H-benzimidazole, 33 g (0.24 mol) of powdered potassium carbonate and 300 ml of ethyl acetate at the reflux temperature and, when the addition has ended, the mixture is heated at the boiling point for a further 4 hours. For working up, the cooled reaction mixture is washed twice with 150 ml of water each time, dried over sodium sulphate and concentrated in vacuo. The residue is purified by chromatography over silica gel (mobile phase: methylene chloride).

32.4 g (83% of theory) of 5,6-dichloro-1-ethoxymethyl-2-trifluoromethyl-benzimidazole of melting point 89°–92° C. are obtained.

The following substituted benzimidazoles of the general formula (Ib) are obtained in a corresponding manner and in accordance with the general preparation statements:

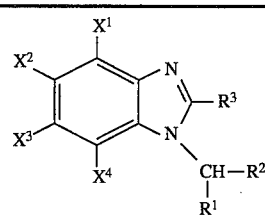

| Ib-Ex. No. | $X^1$ | $X^2$ | $X^3$ | $X^4$ | $R^1$ | $R_2$ | $R^3$ | Physical properties |
|---|---|---|---|---|---|---|---|---|
| 2 | H | Cl | Cl | H | H | CH$_3$–N(COOCH$_3$) | CF$_3$ | m.p. 120–121° C. |
| 3 | H | Cl | Cl | H | H | CH$_3$–N(COOC$_2$H$_5$) | CF$_3$ | m.p. 95–97° C. |
| 4 | H | Cl | Cl | H | H | C$_2$H$_5$–N(COOC$_2$H$_5$) | CF$_3$ | m.p. 104–106° C. |
| 5 | H | Cl | Cl | H | H | C$_2$H$_5$–N(COOCH$_3$) | CF$_3$ | m.p. 88–89° C. |
| 6 | H | Cl | Cl | H | H | n-C$_3$H$_7$–N(COOCH$_3$) | CF$_3$ | m.p. 102–103° C. |
| 7 | Cl (H) | H (Cl) | Cl (H) | H (Cl) | H | —O—C$_2$H$_5$ | CF$_3$ | m.p. 57–61° C. (87:13) |
| 8 | Cl (H) | H (Cl) | Cl (H) | H (Cl) | H | CH$_3$–N(COOCH$_3$) | CF$_3$ | m.p. 95–100° C. (92:8) |
| 9 | H | Cl (H) | H (Cl) | H | H | —O—CH(CH$_3$)$_2$ | CF$_3$ | $^1$H-NMR*): 5.63; 5.65; 7.35; 7.40; 7.57; 7.78; 7.63; 7.85 |
| 10 | H | Cl (H) | H (Cl) | H | H | CN | CF$_3$ | $^1$H-NMR*): 5.15; 5.18; 7.45; 7.55; 7.83; 7.90 |
| 11 | H | Cl (H) | H (Cl) | H | H | —O—C$_2$H$_5$ | CF$_3$ | $^1$H-NMR*): 5.43; 5.48; 7.28–8.01 |
| 12 | H | Cl | H | H | H | —O—C$_2$H$_5$ | CF$_3$ | m.p. 75° C. |

-continued

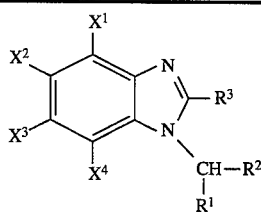

| Ib-Ex. No. | $X^1$ | $X^2$ | $X^3$ | $X^4$ | $R^1$ | $R_2$ | $R^3$ | Physical properties |
|---|---|---|---|---|---|---|---|---|
| 13 | H | H | Cl | H | H | $-O-C_2H_5$ | $CF_3$ | m.p. 73° C. |
| 14 | H | Cl (H) | H (Cl) | H | H | $\begin{array}{c}CH_3\\|\\N\\ \diagdown COOC_2H_5\end{array}$ | $CF_3$ | $^1$H-NMR*): 5,88; 5.92; 7.35; 7.67; 7.92 |
| 15 | H | Cl (H) | H (Cl) | H | H | $\begin{array}{c}C_2H_5\\|\\N\\ \diagdown COOC_2H_5\end{array}$ | $CF_3$ | $^1$H-NMR*): 5.88; 5.90; 7.41; 7.79; 7.81 |
| 16 | H | Cl (H) | H (Cl) | H | H | $\begin{array}{c}n\text{-}C_3H_7\\|\\N\\ \diagdown COOC_2H_5\end{array}$ | $CF_3$ | $^1$H-NMR*): 5.89; 5.96; 7.37; 7.78; 7.78; 7.81 |
| 17 | H | Cl (H) | H (Cl) | H | H | OH | $CF_3$ | |
| 18 | H | $NO_2$ (H) | H ($NO_2$) | H | H | $-O-C_2H_5$ | $CF_3$ | $^1$H-NMR*): 7.79–8.78: A: 5.73 B: 5.74 |
| 19 | H | $NO_2$ | H | H | H | $-O-C_2H_5$ | $CF_3$ | m.p. 48° C. |
| 20 | H | H | $NO_2$ | H | H | $-O-C_2H_5$ | $CF_3$ | m.p. 90° C. |
| 21 | H | $NO_2$ (H) | H ($NO_2$) | H | H | $-O\text{-}n\text{-}C_3H_7$ | $CF_3$ | $^1$H-NMR*): 7.80–8.70; A: 5.80 B: 5.85 |
| 22 | H | $NO_2$ (H) | H ($NO_2$) | H | H | $\begin{array}{c}CH_3\\|\\N\\ \diagdown COOCH_3\end{array}$ | $CF_3$ | $^1$H-NMR*): 7.95–8.80; A: 5.96 B: 5.99 |
| 23 | H | $NO_2$ (H) | H ($NO_2$) | H | H | $\begin{array}{c}C_2H_5\\|\\N\\ \diagdown COOC_2H_5\end{array}$ | $CF_3$ | $^1$H-NMR*): 7.90–8.75; A: 5.97 B: 5.38 |
| 24 | (H) | ($NO_2$) (H) | H ($NO_2$) | H | H | $\begin{array}{c}n\text{-}C_3H_7\\|\\N\\ \diagdown COOC_2H_5\end{array}$ | $CF_3$ | $^1$H-NMR*): 7.91–8.80; A: 5.97 B: 5.99 |
| 25 | H | $NO_2$ (H) | H ($NO_2$) | H | H | OH | $CF_3$ | $^1$H-NMR*): 7.85–8.9; A: 5.85 B: 5.89 |
| 26 | H | F (H) | H (F) | H | H | $-O-C_2H_5$ | $CF_3$ | $^1$H-NMR*): A: 5.63; 7.10–7.90 B: 5.69 |
| 27 | H | ![2,6-dichloro-4-trifluoromethylphenoxy] (H) | H (2,6-dichloro-4-trifluoromethylphenoxy) | H | H | $-O-C_2H_5$ | $CF_3$ | $^1$H-NMR*): 5.61; 5.68; 6.91–7.85 |

-continued

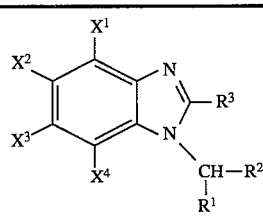

| Ib-Ex. No. | X¹ | X² | X³ | X⁴ | R¹ | R₂ | R³ | Physical properties |
|---|---|---|---|---|---|---|---|---|
| 28 | H | Cl / CF₃-phenyl(Cl,Cl)-O— (H) | H / CF₃-phenyl(Cl,Cl)-O— | H | H | —O-n-C₃H₇ | CF₃ | ¹H-NMR*): 5.63; 5.79; 6.82–7.86 |
| 29 | H | Cl / CF₃-phenyl(Cl,Cl)-O— (H) | H / CF₃-phenyl(Cl,Cl)-O— | H | H | CH₃–N(–)–COOC₂H₅ | CF₃ | ¹H-NMR*): 5.94; 5.86; 6.86–7.90 |
| 30 | H | Cl / CF₃-phenyl(Cl,Cl)-O— (H) | H / CF₃-phenyl(Cl,Cl)-O— | H | H | C₂H₅–N(–)–COOC₂H₅ | CF₃ | ¹H-NMR*): 5.80; 5.84; 6.88–7.89 |
| 31 | (H) | Cl / CF₃-phenyl(Cl,Cl)-O— (H) | H / CF₃-phenyl(Cl,Cl)-O— | H | H | n-C₃H₇–N(–)–COOC₂H₅ | CF₃ | ¹H-NMR*): 5.78 (s), 5.88(s), 6.88–7.95 |
| 32 | H | Cl / CF₃-phenyl(Cl,Cl)-O— (H) | H / CF₃-phenyl(Cl,Cl)-O— | H | H | CN | CF₃ | (m) ¹H-NMR*): 5.11; 6.95; 7.04; 7.74; 7.93 |
| 33 | Br | Cl | Cl | H | H | C₂H₅–N–COOC₂H₅ | CF₃ | m.p. 100–103° C. |

*)The ¹H-NMR spectra were recorded in deuterochloroform (CDCl₃) or hexadeutero-dimethyl sulphoxide (DMSO-d₆) with tetramethylsilane (TMS) as the internal standard. The chemical shift is stated as the δ value in ppm.

Preparation of the starting compounds for the compounds Ib:

Example IIb-1

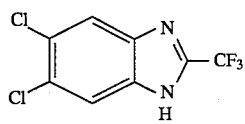

35.4 g (0.2 mol) of 4,5-dichlorophenylene-diamine are heated at the reflux temperature with 150 ml of trifluoroacetic acid for 3 hours. For working up, excess trifluoroacetic acid is distilled off and the residue is partitioned between 100 ml of water and 300 ml of ethyl acetate. The organic phase is separated off, washed in succession with in each case 100 ml of aqueous sodium bicarbonate solution and water, dried over sodium sulphate and concentrated in vacuo. The residue is purified by chromatography over silica gel (mobile phase: cyclohexane/ethyl acetate 1:1).

42.1 g (81% of theory) of 5,6-dichloro-2-trifluoromethyl-1H-benzimidazole of melting point 225°–230° C. are obtained.

The following 1H-benzimidazoles of the formula (IIb) are obtained in a corresponding manner:

Example Ic-1

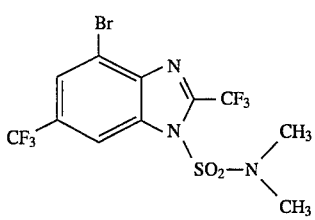

6.6 g (0.045 mol) of dimethylsulphamoyl chloride are added dropwise to a mixture of 10.2 g (0.03 mol) of 2,6-bis-(trifluoromethyl)-4-bromo-1H-benzimidazole, 8.4 g (0.06 mol) of powdered potassium carbonate and 100 ml of acetonitrile at room temperature, while stirring, and, when the addition has ended, the mixture is heated at the reflux temperature for 6 hours. For working up, the cooled reaction mixture is filtered, the filtrate is concentrated in vacuo and the residue is purified by chromatography over silica gel (mobile phase: methylene chloride).

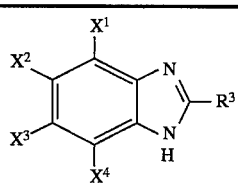
(IIb)

| Ex. No. | $X^1$ | $X^2$ | $X^3$ | $X^4$ | $R^3$ | Physical properties |
|---|---|---|---|---|---|---|
| IIb-2 | H | (see structure at right) | (see structure at right) | H | $CF_3$ | m.p. 227° C. |
| IIb-3 | H | F (H) | H (F) | H | $CF_3$ | m.p. 213° C. |
| IIb-4 | H | $NO_2$ (H) | H ($NO_2$) | H | $CF_3$ | m.p. 151° C. |
| IIb-5 | H | Cl (H) | H (Cl) | H | $CF_3$ | m.p. 193° C. |
| IIb-6 | Cl (H) | H (Cl) | Cl (H) | H (Cl) | $CF_3$ | m.p. 165–170° C. |
| IIb-7 | Br | Cl | Cl | H | $CF_3$ | m.p. 195–199° C. |

*)The $^1$H-NMR spectra were recorded in deuterochloroform ($CDCl_3$) or hexadeutero-dimethyl sulphoxide (DMSO-$d_6$) with tetramethylsilane (TMS) as the internal standard. The chemical shift is stated as the δ value in ppm.

7.7 g (58% of theory) of 2,6-bis-(trifluoromethyl)-4-bromo-1-dimethylsulphamoyl-benzimidazole of melting point 147°–147° C. are obtained.

The following substituted benzimidazoles of the general formula (Ic) are obtained in a corresponding manner and in accordance with the general preparation statements:

Examples for the preparation of the compounds Ic:

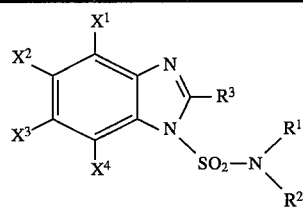

(Ic)

| Ic-Ex. No. | $X^1$ | $X^2$ | $X^3$ | $X^4$ | $R^1$ | $R^2$ | $R^3$ | Physical properties |
|---|---|---|---|---|---|---|---|---|
| 2 | H | Cl | H | H | $CH_3$ | $CH_3$ | $CF_3$ | $^1$H-NMR*): 2.91; 6.85–7.88 |
|  |  | (2,6-dichloro-4-trifluoromethylphenoxy) | (2,6-dichloro-4-trifluoromethylphenoxy) |  |  |  |  |  |
| 3 | H | F (H) | H (F) | H | $CH_3$ | $CH_3$ | $CF_3$ | $^1$H-NMR*): 2.78; 7.32–8.1 |
| 4 | H | F (H) | H (F) | H | H | $-CH(CF_3)CH_3$ | $CF_3$ | MS: m/e = 379 (M$^+$, 100%) |
| 5 | H | $NO_2$ (H) | H ($NO_2$) | H | H | $-CH(CF_3)CH_3$ | $CF_3$ | MS: m/e = 310 (M$^+$, 100%) |
| 6 | H | $NO_2$ (H) | H ($NO_2$) | H | $CH_3$ | $CH_3$ | $CF_3$ | $^1$H-NMR*): 2.95; 7.81–8.58 |
| 7 | H | Cl (H) | H (Cl) | H | $CH_3$ | $CH_3$ | $CF_3$ | $^1$H-NMR*): 2.89; 7.31–7.91 |
| 8 | H | $-O-CF_2-O-$ |  | H | $CH_3$ | $CH_3$ | $CF_3$ | m.p. 179° C. |
| 9 | H | $-O-C(CF_3)(CH_2-CF_3)-O-$ |  | H | $CH_3$ | $CH_3$ | $CF_3$ | $^1$H-NMR*): 3.04–7.35; 7.58; 3.055 |
| 10 | H | $CF_3$ (H) | H ($CF_3$) | H | $CH_3$ | $CH_3$ | $CF_3$ | $^1$NMR*): 2.91; 7.21–8.01 |
| 11 | H | $CF_3$ (H) | H ($CF_3$) | H | H | $-CH(CF_3)CH_3$ | $CF_3$ | MS: m/e = 249 (M$^+$, 100%) |
| 12 | H | $CF_3$ (Br) | Br ($CF_3$) | H | $CH_3$ | $CH_3$ | $CF_3$ | $^1$H-NMR*): A: 2.80; 7.91; 8.11 B: 2.81, 7.94; 8.08 |
| 13 | H | $CF_3$ (Cl) | Cl ($CF_3$) | H | H | $-CH(CF_3)CH_3$ | $CF_3$ | $^1$H-NMR*): A: 7.85; 8.10 B: 7.99; 8.00 |
| 14 | H | $CF_3$ (Cl) | Cl ($CF_3$) | H | $CH_3$ | $CH_3$ | $CF_3$ | $^1$H-NMR*): A: 2.81; 7.82; 8.06 B: 2.83; 7.99; 8.01 |
| 15 | H | $-O-CH_2-CH_2-O-$ |  | H | $CH_3$ | $CH_3$ | $CF_3$ | m.p. 147° C. |
| 16 | H | $-O-CF_2-CHF-O-$ ($-O-CHF-CF_2-O-$) |  | H | $CH_3$ | $CH_3$ | $CF_3$ | 3.07; 6.05; 7.62; 7.78 |
| 17 | H | $-O-CF_2-CClF-O-$ ($-O-CClF-CF_2-O-$) |  | H | $CH_3$ | $CH_3$ | $CF_3$ | m.p. 105° C. |
| 18 | H | $CF_3O$ (H) | H ($CF_3O$) | H | $CH_3$ | $CH_3$ | $CF_3$ | $^1$H-NMR*): 2.98; 7.30–7.62 |
| 19 | H | $CF_3O$ | $CF_3O$ | H | $CH_3$ | $CH_3$ | $CF_3$ | $^1$H-NMR*): 2.98; 7.75; 7.93 |

-continued

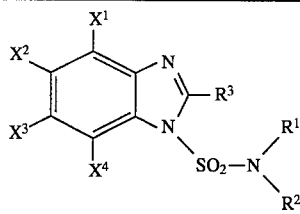
(Ic)

| Ic-Ex. No. | X$^1$ | X$^2$ | X$^3$ | X$^4$ | R$^1$ | R$^2$ | R$^3$ | Physical properties |
|---|---|---|---|---|---|---|---|---|
| 20 | H | CF$_3$ (CH$_3$O) | CH$_3$O (CF$_3$) | H | CH$_3$ | CH$_3$ | CF$_3$ | $^1$H-NMR*): 5.49; 5.53; 6.61–8.11 |
| 21 | H | C$_2$H$_5$O—CO— (H) | H (C$_2$H$_5$O—CO—) | H | CH$_3$ | CH$_3$ | CF$_3$ | |
| 22 | H | C$_6$H$_5$—CO—NH— (H) | H (C$_6$H$_5$—CO—NH—) | H | CH$_3$ | CH$_3$ | CF$_3$ | $^1$H-NMR*): 22.79; 7.60–8.31; 10.45 |
| 23 | H | (CH$_3$)$_2$N—CO— (H) | H ((CH$_3$)$_2$N—CO—) | H | CH$_3$ | CH$_3$ | CF$_3$ | |
| 24 | H | F$_2$CH—CF$_2$—O— (H) | H (F$_2$CH—CF$_2$—O—) | H | CH$_3$ | CH$_3$ | CF$_3$ | $^1$H-NMR*): 3.12; 5.96; 7.28–8.03 |
| 25 | H | C$_6$H$_5$—SO$_2$—NH—) (H) | H (C$_6$H$_5$—SO$_2$—NH—) | H | CH$_3$ | CH$_3$ | CF$_3$ | |
| 26 | H | CF$_3$S (H) | H (CF$_3$S) | H | CH$_3$ | CH$_3$ | CF$_3$ | $^1$H-NMR,*): 3.01; 7.58–7.92 |
| 28 | H | COOH (H) | H (COOH) | H | CH$_3$ | CH$_3$ | CF$_3$ | |

*)The $^1$H-NMR spectra were recorded in deuterochloroform (CDCl$_3$) or hexadeutero-dimethyl sulphoxide (DMSO-d$_6$) with tetramethylsilane (TMS) as the internal standard. The chemical shift is stated as the δ value in ppm.

The following substituted benzimidazoles of the formula (Ic) are also obtained in a corresponding manner:

(Ic)

| Ic-Ex. No. | X¹ | X² | X³ | X⁴ | Physical properties |
|---|---|---|---|---|---|
| 28 | H | 2-CF₃-C₆H₄-SO₂-NH— (H) | H | H | ¹H-NMR*): 2.81; 7.01–7.98 |
| 29 | H | (CH₃)₃C-CH₂-O-C(=O)— (H) | H | H | ¹H-NMR*): 3.02; 7.57–8.79 |
| 30 | H | 2,4-Cl₂-C₆H₃-NH-C(=O)-NH— (H) | H | H | ¹H-NMR*): 2.85; 7.18–8.03 |

-continued (Ic)

[Structure: benzimidazole with CF₃ at 2-position, SO₂-N(CH₃)₂ on N1, and X¹, X², X³, X⁴ substituents on benzene ring]

| Ic- Ex. No. | $X^1$ | $X^2$ | $X^3$ | $X^4$ | Physical properties |
|---|---|---|---|---|---|
| 31 | H | 3-(F₃C–CH₂–O)-4-(F₃C-CH₂-O)-C₆H₃-NH-C(O)-NH– (H) | H | H | MS: m/e = 642 (M⁺); 200(100%) |
| 32 | H | 3-Cl-4-(C₂H₅O–(CH₂)₂–O)-C₆H₃-NH-C(O)-NH– (H) | H | H | ¹H-NMR*: 2.98; 6.81–8.11 |
| 33 | H | 3-Cl-4-(n-C₃H₇O–(CH₂)₂–O)-C₆H₃-NH-C(O)-NH– | H | H | |

-continued (Ic)

| Ic- Ex. No. | $X^1$ | $X^2$ | $X^3$ | $X^4$ | Physical properties |
|---|---|---|---|---|---|
| 34 | H | (H) C₂H₅O—(CH₂)₂—O—C₆H₃(Cl)—NH—C(=O)—NH— | n-C₃H₇O—(CH₂)₂—O—C₆H₃(Cl)—NH—C(=O)—NH— | H | ¹H-NMR*): 3.08; 6.86–8.18 |
| 35 | H | (H) i-C₃H₇O—(CH₂)₂—O—C₆H₄—NH—C(=O)—NH— | C₂H₅O—(CH₂)₂—O—C₆H₄—NH—C(=O)—NH— | H |  |
| 36 | H | (H) 4-Cl-C₆H₄-CH₂-SO₂-N(CH₂OC₂H₅)— | i-C₃H₇O—(CH₂)₂—O—C₆H₄—NH—C(=O)—NH— | H | ¹H-NMR*): 2.88; 7.21–7.78; 9.50 |

(additional substituent shown: 4-Cl-C₆H₄-CH₂-SO₂-N(CH₂OC₂H₅)—)

-continued (Ic)

Structure: benzimidazole with CF₃ at 2-position, N-SO₂-N(CH₃)₂ substituent, and X¹, X², X³, X⁴ on benzene ring.

| Ic-Ex. No. | X¹ | X² | X³ | X⁴ | Physical properties |
|---|---|---|---|---|---|
| 37 | H | C₆H₅-CH₂-SO₂-NH- (H) | H (CH₂-SO₂-NH-) | H | ¹H-NMR*): 2.83; 6.39–7.82 |
| 38 | H | 4-O₂N-C₆H₄-C(O)-NH- (H) | H (4-O₂N-C₆H₄-C(O)-NH-) | H | ¹H-NMR*): 2.81; 7.58–8.38 |
| 39 | H | 2-Cl-C₆H₄-C(O)-NH- (H) | H (2-Cl-C₆H₄-C(O)-NH-) | H | ¹H-NMR*): 2.82; 7.29–8.75 |

*)The ¹H-NMR spectra were recorded in deuterochloroform (CDCl₃) or hexadeutero-dimethyl sulphoxide (DMSO-d₆) with tetramethylsilane (TMS) as the internal standard. The chemical shift is stated as the δ value in ppm.

Preparation of the starting compounds for the compounds Ic:

Example IIc-1

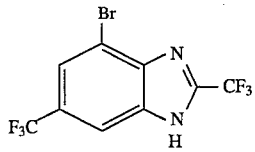

382 g (2.5 mol) of phosphorus oxychloride are added dropwise to a mixture of 290 g (1 mol) of 3-bromo-5-trifluoromethyl-o-phenylenediamine hydrochloride, 150 g (1.42 mol) of trifluoroacetic acid and 1.4 l of 1,2-dimethoxyethane at room temperature, while stirring, and the mixture is then stirred at 60° C. for 6 hours and at room temperature for a further 15 hours. For working up, the solvent and excess phosphorus oxychloride are distilled off, the residue is stirred into 600 ml of ice-water and the mixture is extracted three times with 500 ml of ethyl acetate each time: the combined organic phases are dried and concentrated in vacuo, and the residue is purified by chromatography over silica gel (mobile phase: cyclohexane/ethyl acetate 2:1).

237 g (72% of theory) of 2,6-bis-(trifluoromethyl)-4-bromo-1H-benzimidazole of melting point 127°–130° C. are obtained.

The following substituted 1H-benzimidazoles of the general formula (IIc) are obtained in a corresponding manner:

(IIc)

Structure: Benzimidazole with X¹, X², X³, X⁴ on benzene ring and R³ at 2-position of imidazole:

2,6-dichloro-4-(trifluoromethyl)phenoxy group (Ar = 2,6-Cl$_2$-4-CF$_3$-C$_6$H$_2$-O-)

| Ex. No. | X¹ | X² | X³ | X⁴ | R³ | Physical properties |
|---|---|---|---|---|---|---|
| IIc-2 | H | (2,6-Cl$_2$-4-CF$_3$-C$_6$H$_2$-O-) (H) | H | H | CF$_3$ | m.p. 227° C. |
| IIc-3 | H | F | H | H | CF$_3$ | m.p. 213° C. |
| IIc-4 | H | (H) NO$_2$ (H) | (F) H (NO$_2$) | H | CF$_3$ | m.p. 151° C. |
| IIc-5 | H | Cl | H | H | CF$_3$ | m.p. 193° C. |
| IIc-6 | Cl | (H) | (Cl) | H | CF$_3$ | m.p. 165–170° C. |
| IIc-7 | (H) Br | (Cl) Cl | Cl (H) | (Cl) H | CF$_3$ | m.p. 195–199° C. |
| IIc-8 | (H) H | (H) | (H) | (Br) H | CF$_3$ | m.p. 120–122° C. |
| IIc-9 | H | H (C$_6$H$_5$—O—) CH$_3$—CO— | C$_6$H$_5$—CO— H (CH$_3$—CO—) | H | CF$_3$ | m.p. 145–149° C. |
| IIc-10 | H | Cl—CH$_2$—SO$_2$— (H) | H (Cl—CH$_2$—SO$_2$—) | H | CF$_3$ | m.p. 197–200° C. |
| IIc-11 | H | —O—CH$_2$—CH$_2$—O— | | H | CF$_3$ | m.p. >230° C. |
| IIc-12 | Br | H | Cl—CH$_2$—SO$_2$— | H | CF$_3$ | m.p. 180–187° C. |
| IIc-13 | (H) H | CF$_3$ | (H) Br | (Br) H | CF$_3$ | m.p. 209° C. |

-continued

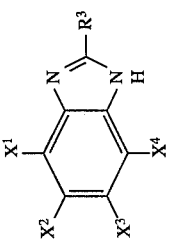
(IIc)

| Ex. No. | X¹ | X² | X³ | X⁴ | R³ | Physical properties |
|---|---|---|---|---|---|---|
| IIc-14 | H | (Br) | (CF₃) | H | CF₃ | m.p. 242° C. |
| IIc-15 | H | —O—CF₂—O— | | H | CF₃ | m.p. 235–237° C. |
| IIc-16 | H | —O—CF₂—CF₂—O— | | H | CF₃ | m.p. 217° C. |
| IIc-17 | H | —O—CF₂—CHF—O— | | H | CF₃ | m.p. 185° C. |
| IIc-18 | H | (—O—CHF—CF₂—O—) | | H | CF₃ | m.p. 144° C. |
| | | —O—CFCl—CFCl—O— | | | | |
| IIc-19 | H | Cl | Cl | H | CF₃ | m.p. 209° C. |
| | | (CF₃O) | (CF₃O) | | | |
| IIc-20 | H | CF₃O | H | H | CF₃ | m.p. 168° C. |
| | | (H) | (CF₃O) | | | |
| IIc-21 | H | CF₃O | CF₃O | H | CF₃ | m.p. 158° C. |
| IIc-22 | H | CH₃—SO₂— | (CH₃—SO₂—) | CF₃ | CF₃ | m.p. 105° C. |
| | | (H) | CH₃O | (H) | | |
| IIc-23 | (CF₃) | CF₃ | (CF₃) | H | CF₃ | m.p. 60° C. |
| | H | (CH₃O) | H | | | |
| IIc-24 | H | (C₂H₅)N—CO— | ((C₂H₅)N—CO—) | H | CF₃ | m.p. 125° C. |
| | | (H) | | | | |
| IIc-25 | H | C₂H₅O—CO— | (C₂H₅O—CO—) | H | CF₃ | m.p. 140° C. |
| | | (H) | | | | |
| IIc-26 | H | C₆H₅—CO—NH— | (C₆H₅—CO—NH—) | H | CF₃ | m.p. 202° C. |
| | | (H) | | | | |
| IIc-27 | H | CH₃O—CO— | (CH₃O—CO—) | H | CF₃ | m.p. 157° C. |
| | | (H) | | | | |
| IIc-28 | H | (CH₃)₂N—CO— | ((CH₃)₂N—CO—) | H | CF₃ | m.p. 226–227° C. |
| | | (H) | | | | |
| IIc-29 | H | F₂CH—CF₂—O— | (F₂CH—CF₂—O—) | H | CF₃ | m.p. 181° C. |
| | | (H) | H | | | |
| IIc-30 | H | C₆H₅—SO₂—NH— | (C₆H₅—SO₂—NH—) | H | CF₃ | m.p. 99° C. |
| | | (H) | | | | |

-continued (IIc)

| Ex. No. | $X^1$ | $X^2$ | $X^3$ | $X^4$ | $R^3$ | Physical properties |
|---|---|---|---|---|---|---|
| IIc-31 | H | 2-Cl-C$_6$H$_4$-SO$_2$-NH- (H) | H | H | CF$_3$ | m.p. 67° C. |
| IIc-32 | H | 2-CF$_3$-C$_6$H$_4$-SO$_2$-NH- (H) | H | H | CF$_3$ | m.p. 79° C. |
| IIc-33 | H | (CH$_3$)$_3$C-CH$_2$-O-C(=O)- (H) | H | H | CF$_3$ | m.p. 214-215° C. |

-continued

| Ex. No. | $X^1$ | $X^2$ | $X^3$ | $X^4$ | $R^3$ | Physical properties |
|---|---|---|---|---|---|---|
| IIc-34 | H | (2,4-dichlorophenyl-NHC(O)NH–) | H | H | $CF_3$ | m.p. 254–255° C. |
| IIc-35 | H | (3-(2,2,2-trifluoroethoxy-with CF_3)phenyl-NHC(O)NH–) | H | H | $CF_3$ | m.p. 103° C. |
| IIc-36 | H | 3-chloro-4-(2-ethoxyethoxy)phenyl-NHC(O)NH– | H | H | $CF_3$ | m.p. 186° C. |

-continued (IIc)

| Ex. No. | X¹ | X² | X³ | X⁴ | R³ | Physical properties |
|---|---|---|---|---|---|---|
| IIc-37 | H | n-C₃H₇O—(CH₂)₂—O—(3-Cl,4-)C₆H₃—NH—C(=O)—NH— (H) | C₂H₅O—(CH₂)₂—O—(3-Cl,4-)C₆H₃—NH—C(=O)—NH— | H | CF₃ | m.p. 144° C. |
| IIc-38 | H | C₂H₅O—(CH₂)₂—O—(4-)C₆H₄—NH—C(=O)—NH— (H) | n-C₃H₇O—(CH₂)₂—O—(3-Cl,4-)C₆H₃—NH—C(=O)—NH— | H | CF₃ | m.p. 207° C. |
| IIc-39 | H | i-C₃H₇O—(CH₂)₂—O—(4-)C₆H₄—NH—C(=O)—NH— | C₂H₅O—(CH₂)₂—O—(4-)C₆H₄—NH—C(=O)—NH— | H | CF₃ | m.p. 201° C. |

-continued $$\text{(IIc)}$$

Structure: benzimidazole with X¹, X², X³, X⁴ on benzene ring and R³ at 2-position

| Ex. No. | X¹ | X² | X³ | X⁴ | R³ | Physical properties |
|---|---|---|---|---|---|---|
| IIc-41 | H | (H) | –(CH₂)₂–O–C₃H₇-i attached to p-position of phenyl with NH–C(=O)–NH– linkage | | | |
| IIc-42 | | (CF₃)₂N– (H) | H ((CF₃)₂N–) | H | CF₃ | m.p. 68° C. |
| IIc-43 | H | C₆H₅–CH₂–SO₂–NH– (H) | C₆H₅–CH₂–SO₂–NH– | H | CF₃ | m.p. 174° C. |
| IIc-44 | H | CF₃S (H) | H (CF₃S) | H | CF₃ | m.p. 157° C. |
| | H | FClCH–CF₂–O– (H) | H (FClCH–CF₂–O–) | | | |
| IIc-45 | H | 2,4-dichlorophenyl-NH–C(=O)–NH– (H) | 2,4-dichlorophenyl-NH–C(=O)–NH– | H | CF₃ | m.p. 176° C. |

-continued
(IIc)
| Ex. No. | $X^1$ | $X^2$ | $X^3$ | $X^4$ | $R^3$ | Physical properties |
|---|---|---|---|---|---|---|
| IIc-46 | H |  (H) | H | H | $CF_3$ | m.p. 190° C. |
| IIc-47 | H | 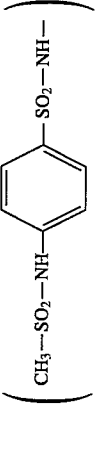 (H) |  | H | $CF_3$ | m.p. 208° C. |
| IIc-48 | H | 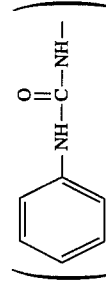 (H) | H | H | $CF_3$ | |
| IIc-49 | H | $(CH_3)_3C-O-CO-$ (H) | 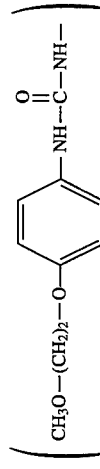 $((CH_3)_3C-O-CO-)$ | H | $CF_3$ | m.p. 162° C. |
| IIc-50 | H | 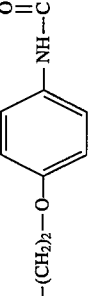 | H | H | $CF_3$ | m.p. 70° C. |

-continued
(IIc)
| Ex. No. | $X^1$ | $X^2$ | $X^3$ | $X^4$ | $R^3$ | Physical properties |
|---|---|---|---|---|---|---|
| IIc-52 | H | (H) | 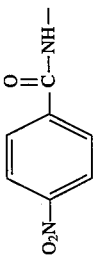COOCH₃, SO₂—NH— | H | CF₃ | m.p. 194° C. |
| IIc-53 | H | 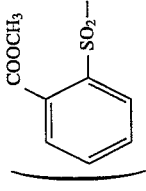O₂N—C(=O)—NH— (H) | 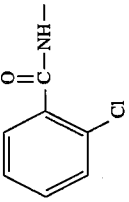O₂N—C(=O)—NH— | H | CF₃ | m.p. 220° C. |
| IIc-54 | H | 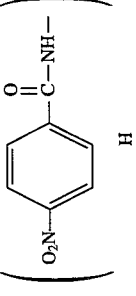Cl—C(=O)—NH— (H) | 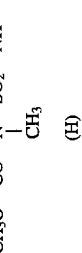Cl—C(=O)—NH— | H | CF₃ | |
| | | CH₃O—CO—N(CH₃)—SO₂—NH— (H) | (CH₃O—CO—N(CH₃)—SO₂—NH—) | | | |

-continued (IIc)

| Ex. No. | X$^1$ | X$^2$ | X$^3$ | X$^4$ | R$^3$ | Physical properties |
|---|---|---|---|---|---|---|
| IIc-55 | H | COOH (H) | H (COOH) | H | CF$_3$ | m.p. 250° C. |
| IIc-56 | H | (CH$_3$)$_3$C—NH—CO— (H) | H ((CH$_3$)$_3$C—NH—CO—) | H | CF$_3$ | m.p. 187° C. |
| IIc-57 | H | $\begin{matrix} CH_3 & O \\ F_3C-C-NH-C- \\ CH_3 \end{matrix}$ (H) | (H) $\begin{matrix} CH_3 & O \\ F_3C-C-NH-C- \\ CH_3 \end{matrix}$ | | | m.p. 167° C. |
| IIc-58 | H | NC—CH$_2$— (H) | H (NC—CH$_2$—) | H | CF$_3$ | |
| IIc-59 | H | NH$_2$ (H) | H (NH$_2$) | H | CF$_3$ | |
| IIc-60 | H | HOOC—CH$_2$— (H) | H (HOOC—CH$_2$—) | H | CF$_3$ | |
| IIc-61 | H | F$_3$C—SO$_2$— (H) | H (F$_3$C—SO$_2$—) | | CF$_3$ | |
| IIc-62 | H | H$_3$C—SO$_2$— (H) | H (H$_3$C—SO$_2$—) | H | CF$_3$ | m.p. 143° C. |
| IIc-63 | H | H (C$_6$H$_5$) | C$_6$H$_5$ (H) | H | CF$_3$ | m.p. 177–182° C. |
| IIc-64 | H | C$_2$H$_5$O (H) | H (C$_2$H$_5$O) | H | CF$_3$ | m.p. 86–90° C. |
| IIc-65 | H | CH$_3$O H | CH$_3$O CH$_3$O | H | CF$_3$ | m.p. 184–188° C. |
| IIc-66 | H | H (CH$_3$O) | (H) | H | CF$_3$ | m.p. 144–146° C. |
| IIc-67 | H | H (c-C$_6$H$_{11}$) | c-C$_6$H$_{11}$ (H) | H | CF$_3$ | m.p. 198–200° C. |
| IIc-68 | H | H (t-C$_4$H$_9$) | t-C$_4$H$_9$ (H) | H | CF$_3$ | m.p. <50° C. |
| IIc-69 | CH$_3$ (H) | H | (H) | H (CH$_3$) | CF$_3$ | m.p. 139–142° C. |
| IIc-70 | Br | CH$_3$O | CH$_3$O | H | CF$_3$ | m.p. 183–185° C. |

-continued

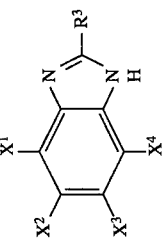
(IIc)

| Ex. No. | $X^1$ | $X^2$ | $X^3$ | $X^4$ | $R^3$ | Physical properties |
|---|---|---|---|---|---|---|
| IIc-71 | (H) Br | $CH_3O$ | $CH_3O$ | (Br) Br | $CF_3$ | m.p. 83–87° C. |
| IIc-72 | H | H ($CH_3$) | $CH_3$ (H) | H | $CF_3$ | m.p. 182° C. |
| IIc-73 | H | H ($CH_3O$) | $CH_3O$ (H) | H | $CF_3$ | m.p. 160° C. |

*) The $^1H$—NMR spectra were recorded in deuterochloroform ($CDCL_3$) or hexadeutero-dimethyl sulphoxide ($DMSO-d_6$) with tetramethylsilane (TMS) as the internal standard. The chemical shift is stated as the δ value in ppm.

Chloro-(2-halogeno-1-fluoromethyl-ethoxy)-methanes of the formula (I)

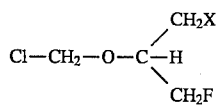

in which
X represents fluorine or chlorine
(specifically, these are chloro-(2-fluoro-1-fluoromethylethoxy)-methane (formula (I), X=fluorine) and chloro-2-chloro-1-fluoromethyl-ethoxy)-methane (formula (I), X= chlorine)) are obtainable by reaction of halogenated isopropanols of the formula (II)

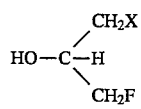

in which
X represent fluorine or chlorine,
with formaldehyde and hydrogen chloride at −20° to +20° C.

They are used for the preparation of substituted benzimidazoles of the formula

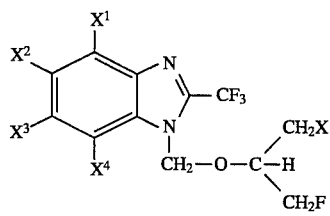

in which
X represent fluorine or chlorine and
$X^1$, $X^2$, $X^3$ and $X^4$ independently of one another in each case represent hydrogen, halogen, cyano or nitro, or represent in each case optionally substituted alkyl, alkoxy, alkylthio, alkylsulphinyl, alkylsulphonyl or cycloalkyl, or represent optionally substituted, fused dioxyalkylene, or represent hydroxycarbonyl, alkylcarbonyl, alkoxycarbonyl or cycloalkyloxycarbonyl, or represent in each case optionally substituted amino or aminocarbonyl, or represent in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but wherein at least one of the substituents $X^1$, $X^2$, $X^3$ or $X^4$ represent halogenoalkyl, with the exception of the chloromethyl radical, halogenoalkoxy, halogenoalkylthio, halogenoalkylsulphinyl, halogenoalkylsulphonyl or alkylsulphonyl, or represent optionally substituted, fused dioxyalkylene, or represent hydroxycarbonyl, alkylcarbonyl, alkoxycarbonyl or cycloalkyloxycarbonyl, or represent in each case optionally substituted amino or aminocarbonyl or represent in each case optionally substituted aryl, arylthio, arylsulphinyl, arylsulphonyl, arylsulphonyloxy, arylcarbonyl, aryloxycarbonyl, arylazo or arylthiomethylsulphonyl,
from benzimidazoles of the formula

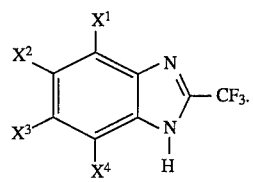

Example 66 g of paraformaldehyde (finely powdered) were added to 192 g of 1,3-difluoro-2-propanol. A vigorous stream of hydrogen chloride gas was then passed in at −10° C., while stirring, until a clear 2-phase mixture had formed. The organic phase was then separated off, dried with calcium chloride and subjected to fractional distillation in vacuo. 183 g (60% of theory) of chloro-(2-fluoro-1 -fluoromethylethoxy)-methane were obtained with a boiling point of 50° to 54° C. under 20 mbar. The characteristic absorptions in the NMR spectra were as follows: $^1$H-NMR: 5.6 ppm and 4.55 ppm. $^{19}$F-NMR: −233 ppm.

Fluorinated 1,3-benzo- and 1,3-pyrido-dioxoles of the formula

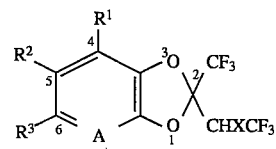

in which
A represents C—$R^4$ or N and
X represents hydrogen, fluorine, chlorine or bromine, and
$R^1$ to $R^4$ can be identical to or different from one another and in each case denote hydrogen, halogen, $C_1$–$C_6$-alkyl, $C_1$–$C_6$-alkoxy, halogeno-$C_1$–$C_6$-alkyl, $C_6$$C_{10}$-aryl, CHO, COOH, COCl, CN, OH, NCO, COO—$C_1$–$C_6$-alkyl, $NO_2$, $NH_2$, NH—$C_1$–$C_6$-alkyl, N($C_1$–$C_6$-alkyl)$_2$, $SO_2$Cl, $SO_3$H, $SO_3$Na or $SO_3$K, wherein two adjacent radicals from the series $R^1$ to $R^4$ also together can represent an optionally substituted —CH═CH—CH═CH— bridge,
are obtainable by reaction of 1,2-dihydroxybenzenes or 2,3-dihydroxypyridines
in which

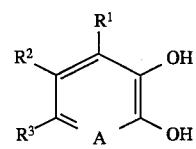

A and $R^1$ to $R^2$ have
the meaning given in the case of formula (I), but $R^1$ to $R^3$ do not represent OH, COCl or $SO_2$Cl,
with a hexafluorobutene of the formula (III)

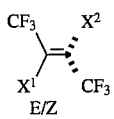

in which
X¹ represents hydrogen or halogen and
X² represents halogen, in the presence of a base and a diluent at −20° to +200° C., or by a procedure in which 1,2-dihydroxybenzenes or 2,3-dihydroxypyridines provided with a protective group, of the formula (IV)

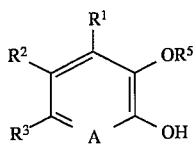

in which
A and R¹ to R² have the meaning given in the case of formula (I) and
R⁵ represent a protective group, or
R⁵ together with R¹ represent a —C(CH₃)₂—O— radical, are first reacted with a hexafluorobutene of the formula (III)

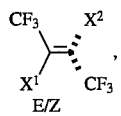

in which
X¹ represents hydrogen or halogen and
X² represents halogen, to thus give an intermediate product of the formula (V)

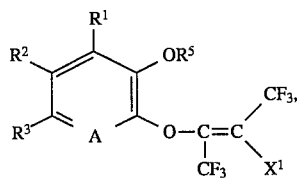

in which

A and R¹ to R² have the meaning given in the case of formula (I),
R⁵ has the meaning given in the case of formula (IV) and
X¹ has the meaning given in the case of formula (III), the protective group R⁵ is split off from the intermediate product of the formula (V), and the OH compound thus obtainable is reacted with a base to thus give i,3-benzo- or 1,3-pyrido-dioxoles of the above formula.

1,3-Benzo- and 1,3-pyrido-dioxoles of the above formula which contain an amino group can be phosgenated, for example with phosgene or diphosgene, and the amino group can thus be converted into an isocyanato group, the isocyanato-1,3-benzo- or -1,3-pyrido-dioxole thus obtained can be reacted with a benzimidazole, for example of the formula

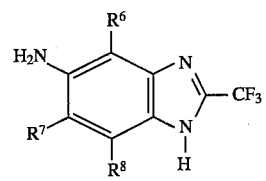

in which
R⁶, R⁷ and R⁸ independently of one another in each case represent hydrogen, halogen, cyano or nitro, or represent in each case optionally substituted alkyl, alkoxy, alkylthio, alkylsulphinyl, alkylsulphonyl or cycloalkyl, or represent optionally substituted fused dioxyalkylene, or represent hydroxycabonyl, alkylcarbonyl, alkoxycarbonyl or cycloalkyloxycarbonyl, or represent in each case optionally substituted amino or aminocarbonyl, or represent in each case optionally substituted aryl, aryloxy, aryl thio, arylsulphinyl, arylsulphonyl, arylsulphonyloxy, arylcarbonyl, aryloxycarbonyl, arylazo or arylthiomethylsulphonyl, but wherein at least one of the substituents R⁶, R⁷ or R⁸ represent halogenoalkyl, with the exception of the chloromethyl radical, halogenoalkoxy, halogenoalkylthio, halogenoalkylsulphinyl, halogenoalkylsulphonyl or alkylsulphonyl, or represent optionally substituted, fused dioxyalkylene, or represent hydroxycarbonyl, alkylcarbonyl, alkoxycarbonyl or cycloalkyloxycarbonyl, or represent in each case optionally substituted aryl, arylthio, arylsulphinyl, arylsulphonyl, aylsulphonyloxy, arylcarbonyl, aryloxycarbonyl, arylazo or arylthiomethylsulphonyl, (for the preparation, see, for example, J. Fluorine Chem. 56, 1 (1992) and references quoted there)

to thus obtain a urea derivative, for example of the formula

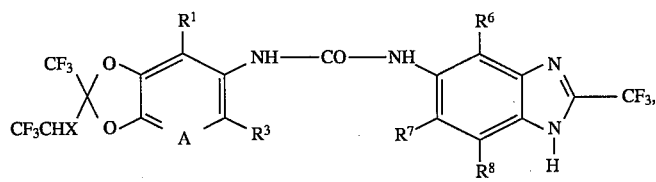

in which
R¹ R³, X, A, R⁶, R⁷ and R⁸ have the meaning given at above, and from this, by alkylation with an alkylating agent, for example of the formula

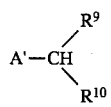

in which
- A' represents a suitable leaving group, for example halogen, in particular represents chlorine, bromine or iodine, or represents in each case optionally substituted alkylsulphonyloxy, alkoxysulphonyloxyor arylsulphonyloxy, in particular methanesulphonyloxy, trifluoromethanesulphonyloxy, methoxysulphonyloxy, ethoxysulphonyloxy or p-toluenesulphonyloxy, or an alcohol, alkanoyloxy, alkoxy or hydroxyl group, in particular an acetoxyor methoxy group,
- $R^9$ represents hydrogen, alkyl or alkoxy, or represents optionally substituted aryl and
- $R^{10}$ represents hydroxyl or cyano, or represents in each case optionally substituted alkyl, alkenyl, alkinyl, alkoxy, alkenyloxy, alkinyloxy, alkylthio, amino, aminocarbonyl, alkylcarbonyl, alkoxycarbonyl, alkylcarbonyloxy, dialkoxyphosphonyl, (hetero)ayl, (hetero)arylcarbonyl, (hetero)aryloxycarbonyl, (hetero)arylcarbonyloxy or (hetero)arylaminocarbonylaminocarbonyloxy, a corresponding urea derivative in which a nitrogen atom beside $R^8$ is substituted by a

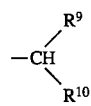

radical can be obtained.

The reactions necessary for the preparation of such urea derivatives (phosgenation, urea formation from isocyanate and amine, alkylation) can be carried out in a manner which is known per se.

Compounds of the formula

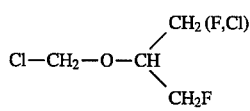

can be obtained by reacting the corresponding isopropanol with formaldehyde and hydrogen chloride at −20° to +20° C.

1,3-Benzo- and 1,3-pyridodioxoles which contain two adjacent amino groups can be converted into the corresponding benzimidazole, for example of the following formula

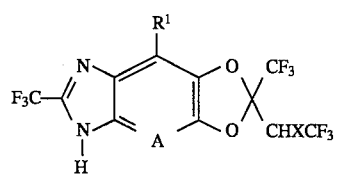

in which

A, $R^1$ and X have the abovementioned meaning, with trifluoroacetic acid.

Benzimidazole derivatives which are substituted in the nitrogen atom adjacent to A with a

radical can be obtained from this product by alkylation.

EXAMPLES

Example 1a 2-(2,2,2-Trifluoroethyl)-2-trifluoromethyl-1,3-benzodioxole 11 g of pyrocatechol were dissolved in 200 ml of dimethylformamide, and 18 g of 45% strength by weight aqueous sodium hydroxide solution were added. 20 g of 2-chloro-1,1,1,4,4,4-hexafluoro-2-butene were added dropwise to the mixture at 75° C. The mixture was subsequently stirred at 75° C. for 30 minutes. It was then poured onto 500 ml of ice-water and extracted with diethyl ether. The organic phase was washed with water, dried with magnesium sulphate and concentrated. Finally, the product was distilled under a high vacuum. The yield was 15 g (=56%), and the boiling point was 60° C. under 10 mbar. The NMR spectra showed the following characteristic absorptions: $^{19}$F-NMR: −59.0 and −84.6 ppm. $^1$H-NMR: 3.02 ppm.

Example 2a 2-(1-Chloro-2,2,2-trifluoroethyl)-2-trifluoromethyl-1,3-benzodioxole 110 g of pyrocatechol were dissolved in 1500 ml of acetonitrile, and 200 g of triethylamine were added. 235 g of 2,3-dichloro-1,1,1,4,4,4-hexafluoro-2-butene were added dropwise to the mixture at 75° C. The mixture was subsequently stirred at 75° C. for 2 hours. 1200 ml of the solvent were then distilled off in vacuo and the residue was taken up in 1500 ml of water. The product was extracted with diethyl ether and the organic phase was washed twice with 10% strength by weight aqueous sodium hydroxide solution and once with water. After drying with magnesium sulphate, the organic phase was concentrated and the residue was subjected to fractional distillation in vacuo. The yield was 258 g (=84% of theory). The boiling point was 63° C. under 12 mbar. The NMR spectra showed the following characteristic absorptions: $^{19}$F-NMR: −66.8 and −79.7 ppm. $^1$H-NMR: 4.71 ppm.

Examples 3 to 10a

The following examples were carried out analogously to Examples 1 and 2 (for details, see Table 1):

TABLE 1

| Example No. a | Analogously to Example No. | Dihydroxybenzene of the formula (II) employed $A = C-R^4$, $R^4 = H$ | | | Resulting product of the formula (I) $A = C-R^4$, $R^4 = H$, $R^1$ to $R^3$ as in the dihydroxybenzene employed | | | Characteristic absorptions in the NMR spectra (ppm) | |
|---|---|---|---|---|---|---|---|---|---|
| | | $R^1$ | $R^2$ | $R^3$ | X | Yield | Boiling point (°C./mbar) | $^{19}F$ | $^1H$ |
| 3 | 1a | Br | H | H | H | 19% | 37/10 | −61.1 −86.8 | 3.04 |
| 4 | 1a | H | CHO | H | H | 33% | 75/0.04 | −59.0 −84.6 | 3.08 |
| 5 | 2a | H | CHO | H | Cl | 51% | 81/0.06 | −68.6 −81.4 | 4.87 |
| 6 | 2a | H | CN | H | Cl | 48% | 76/0.03 | −68.6 −81.4 | 4.80 |
| 7 | 2a | $NO_2$ | H | H | Cl | 72% | n.d. | −68.6 −81.1 | 4.89 |
| 8 | 2a | H | phenyl | H | Cl | 85% | n.d. | −68.6 −81.5 | 4.70 |
| 9 | 2a | H | $CH_3$ | H | Cl | 70% | 95/16 | −68.6 −81.6 | 4.69 |
| 10 | 2a | H | —CH=CH—CH=CH— | | Cl | 92% | crystalline | −68.7 −81.3 | 4.75 | n.d. = not determined

Examples 11a 2-(1-Chloro-2,2,2-trifluoroethyl)-2-trifluoromethyl-[1,3]-dioxolo[4,5-b]pyridine 11 g of 2,3-dihydroxypyridine were reacted with 23.5 g of 2,3-dichloro-1,1,1,4,4,4-hexafluoro-2-butene as described in Example 2. After distillation under a high vacuum, the product was obtained in the form of colourless crystals in an amount of 15.5 g (=50% of theory). The NMR spectra showed the following characteristic absorptions: $^{19}$F-NMR: −68.5 and −81.6 ppm. $^1$H-NMR 4.81 ppm.

Examples 12a 2-(1,1,1,4,4,4-Hexafluoro-2-butenoxy)-methoxybenzene 260 g of 2-methoxyphenol were dissolved in 1 l of dimethylformamide (industrial quality), and 220 g of 45% strength sodium hydroxide solution were added. 400 g of 2-chloro-1,1,1,4,4,4-hexafluoro-2-butene were then added dropwise at 22° C., while stirring. The mixture was subsequently stirred at 22° C. for 2 hours. 1.5 l of ice-water were then added and the mixture was extracted with methylene chloride.

The combined organic phases were washed twice with 10% strength sodium hydroxide solution and once with saturated NaCl solution, dried with $MgSO_4$ and distilled. The yield was 329 g (58% of theory), and the boiling point was 68°–70° C. under 12 mbar. The NMR spectra showed the following characteristic absorptions: $^{19}$F-NMR: −57.6 and −67.9 ppm. $^1$H-NMR: 5.92 ppm.

Example 13a 2-(1,1,1,4,4,4-Hexafluoro-2-butenoxy)-phenol 286.1 g of 2-(1,1,1,4,4,4-hexafluoro-2-butenoxy)-methoxybenzene from Example 12 were dissolved in a mixture of 500 ml of glacial acetic acid and 500 ml of 48% strength hydrobromic acid, and 5 g of triethylbenzylammonium chloride were added. The mixture was stirred at a bath temperature of 150° C. until complete conversion was achieved, according to monitoring by gas chromatography. The mixture was then allowed to cool, and 2 kg of ice-water were added. The aqueous phase was extracted thoroughly with $CH_2Cl_2$. After drying with $MgSO_4$, the solvent was stripped off and the residue was distilled in vacuo. The yield was 200 g (50% of theory), and the boiling point was 80° C. under 16 mbar. The NMR spectra showed the following characteristic absorptions: $^{19}$F-NMR: −59.6 and −69.6 ppm. $^1$H-NMR: 6.1 ppm.

Example 14a 2-(2,2,2-Trifluoroethyl)-2-trifluoromethyl-1,3-benzodioxole 200 g of 2-(1,1,1,4,4,4-hexafluoro-2-butenoxy)-phenol from Example 13 were dissolved in 400 ml of acetonitrile, and 5 g of triethylamine were added. The mixture was stirred at 70° C. for 4 hours. It was then distilled in vacuo. The yield was 162 g (81% of theory), and the boiling point was 60° C. under 10 mbar. The NMR spectra showed the following characteristic absorptions: $^{19}$F-NMR: −59.0 and −84.6 ppm. $^1$H-NMR: 3.02 ppm.

EXAMPLE 15a 2-(2-Chloro-1,1,1-4,4,4-hexafluoro-2-butenoxy)-1-benzyloxybenzene 20 g of 2-benzyloxyphenol were dissolved in 100 ml of dimethylformamide, and 9 g of 45% strength sodium hydroxide solution were added. 23 g of 2,3-dichloro-1,1,1,4,4,4-hexafluoro-2-butene were then added dropwise at room temperature. When the exothermic reaction had subsided, the mixture was subsequently stirred at room temperature for 1 hour, poured onto water and extracted with tert-butyl methyl ether. After drying with $MgSO_4$, the solvent was stripped off. The yield was 29 g (74% of theory). The NMR spectra showed the following characteristic absorptions: $^{19}$F-NMR: −59.5; −60.5; −61.7 and −62.8 ppm.

Example 16a 2-(2-Chloro-1,1,1,4,4,4-hexafluoro-2-butenoxy)-phenol 24.4 g of 2-(2-chloro-1,1,1,4,4,4-hexafluoro-2-butenoxy)-1-benzyloxybenzene from Example 15 were dissolved in 150 ml of tetrahydrofuran and treated with 3 bar of hydrogen in the presence of 2 g of Pd/C (10% strength) at room temperature for 4 hours. The mixture was then filtered, the filtrate was concentrated and the residue was distilled in vacuo. The yield was 13.2 g (69% of theory), and the boiling point was 56° C. under 0.15 mbar.

Example 17a 2-(1-Chloro-2,2,2-trifluoroethyl)-2-trifluoromethyl-1,3-benzodioxole 11.7 g of 2-(2-chloro-1,1,1,4,4,4-hexafluoro-2-butenoxy)phenol from Example 16 were dissolved in 40 ml of tertbutyl methyl ether, and 40 ml of 1N sodium hydroxide solution were added. After the mixture had been stirred at room temperature for 30 minutes, the organic phase was separated off, dried with MgSO$_4$ and distilled. The yield was 10 g (88% of theory), and the boiling point was 63° C. under 12 mbar. The NMR spectra showed the following characteristic absorptions: $^{19}$F-NMR: −66.8 and −79.7 ppm. $^1$H-NMR: 4.71 ppm.

EXAMPLE 18a 2,2-Dimethyl-4-(1,1,1,4,4,4-hexafluoro-2-butenoxy)-1,3-benzodioxole (formula V, R$^5$ together with R$^1$=—C(CH$_3$)$_2$—O— radical)

46 g of 2,2-dimethyl-4-hydroxy-1,3-benzodioxole (formula IV, R$^5$ together with R$^3$=—C(CH$_3$)$_2$—O— radical) were dissolved in 200 ml of N-methylpyrrolidone, and 31 g of 40% strength by weight aqueous sodium hydroxide solution were added. 54.8 g of 2-chloro-1,1,1,4,4,4-hexafluoro-2-butene were then added dropwise at room temperature, while stirring. After the mixture had been subsequently stirred for 1 hour, it was poured onto water and extracted with tert-butyl methyl ether. The organic phase was washed with 10% strength by weight aqueous sodium hydroxide solution and dried with magnesium sulphate, and the readily volatile contents were removed on a rotary evaporator. 73.8 g (=80% of theory) of a product which was 95% pure according to gas chromatography remained. The characteristic absorptions in the NMR spectra were: $^{19}$F-NMR: −58.1 and −68.5 ppm. $^1$H-NMR: 6.73, 6.55, 6.03 and 1.70 ppm.

Example 19a 1,2-Dihydroxy-3-(1,1,1,4,4,4-hexafluoro-2-butenoxy)-benzene 65 g of the product from Example 18 were heated at the boiling point under reflux with 200 ml of concentrated aqueous hydrochloric acid for 4 hours, while stirring. The mixture was then diluted with 300 ml of water and extracted with methylene chloride. After drying with magnesium sulphate, the solvent was stripped off from the organic phase and 54 g of a 90% pure product were obtained. Recrystallisation from cyclohexane gave colourless crystals with a melting point of 105° C. The characteristic absorptions in the NMR spectra were as follows: $^{19}$F-NMR −57.7 and −67.7 ppm. $^1$H-NMR: 6.77, 6.50, 6.21 and 5.42 ppm.

Example 20a 2-(2,2,2-Trifluoroethyl)-2-(trifluoromethyl)-4-hydroxy-1,3-benzodioxole (formula (I), R$^1$=OH, X=H, A=CH, R$^2$ and R$^3$=H).

43.5 g of the product from Example 19 were dissolved in 300 ml of acetonitrile, and 1.5 g of triethylamine were added at room temperature. After the mixture had been stirred at room temperature for 2 hours, the solvent was stripped off and the residue was distilled in vacuo. The yield was 17 g (=39% of theory), the boiling point was 85° C. under 0.15 mbar, and the melting point was 65° C. The characteristic absorptions in the NMR spectra were as follows: $^{19}$F-NMR: −59.0 and −84.5 ppm. $^1$H-NMR: 6.80, 6.55, 6.2 and 3.01 ppm.

Example 21a 2,2-Dimethyl-4-(3-chloro-1,1,1,4,4,4-hexafluoro-2-butenoxy)-1,3-benzodioxole (formula (V), R$^1$ and R$^5$ together —C(CH$_3$)$_2$—O—, X$^1$=Cl, R$^2$+R$^3$=H, A=CH).

33.2 g of 2,2-dimethyl-4-hydroxy-1,3-benzodioxole were reacted with 47 g of 2,3-dichloro-1,1,1,4,4,4-hexafluoro-2-butene analogously to Example 18. The resulting product was distilled in vacuo, and a 1:1 molar mixture of cis/trans isomers was obtained. The yield was 51 g (=70% of theory), and the boiling point was 70° C. under 0.15 mbar. The characteristic absorptions in the NMR spectra were as follows: $^{19}$F-NMR: −60.0, −61.6, −62.2 and 63.4 ppm. $^1$H-NMR: 6.79, 6.65 to 6.48 and 1.7 ppm.

Example 22a 1,2-Dihydroxy-3-(3-chloro-1,1,1,4,4,4-hexafluoro-2-butenoxy)-benzene (formula (V), R$^1$=OH, R$^2$+R$^3$=H, A=CH, R$^5$=H, X$^1$=Cl)

18 g of the product from Example 21 were reacted with 50 ml of concentrated hydrochloric acid analogously to Example 19. 15.7 g of a 97% pure product were obtained. The product was a 1:1 molar mixture of the cis/trans isomers. The characteristic absorptions in the NMR spectra were as follows: $^{19}$F-NMR: −60.2, −61.3, −62.2 and −63.3 ppm. $^1$H-NMR: 6.80, 6.45 and 6.25 ppm.

Example 23a 2-(1-Chloro-2,2,2-trifluoroethyl)-2-trifluoromethyl-4-hydroxy-1,3-benzodioxole 15 g of the product from Example 22 were dissolved in 50 ml of acetonitrile, and 1 ml of triethylamine was added. After the mixture had been stirred for 15 minutes, the solvent was stripped off and the residue was distilled in vacuo. For purification, the product was taken up in diethyl ether and the mixture was filtered over silicon dioxide. After the diethyl ether had been stripped off, 10.5 g of the product (=70% of theory) remained. The melting point was 139+ to 141° C. The characteristic absorptions in the NMR spectra were as follows: $^{19}$F-NMR: −66.6 and −79.3 ppm. $^1$H-NMR: 8.4, 6.76, 6.60, 6.50 and 4.70 ppm.

Example 24a

5-Bromo-2-(2,2,2-trifluoroethyl)-2-trifluoromethyl-1,3-benzodioxole 54.4 g of 2-(2,2,2-trifluoroethyl)-2-trifluoromethyl-1,3-benzodioxole were dissolved in 300 ml of carbon tetrachloride, and 0.4 g of anhydrous iron(III) chloride was added. 32 g of bromine were then added dropwise at the reflux temperature and the mixture was subsequently stirred until the reaction was complete (monitoring by gas chromatography). The mixture was then allowed to cool, and was washed with 10% strength by weight aqueous sodium hydrogen sulphide solution and water, dried with magnesium sulphate and concentrated. The residue was distilled in vacuo. The yield was 58 g (83% of theory), and the boiling point was 80° C. under 14 mbar. The characteristic absorptions in the NMR spectra were as follows: $^{19}$F-NMR: −59.2 and −84.9 ppm. $^1$H-NMR: 3.02 ppm.

Example 25a

5-Bromo-2-(1-chloro-2,2,2-trifluoroethyl)-2-trifluoromethyl-1,3-benzodioxole 51 g of 2-(1-chloro-2,2,2-trifluoroethyl)-2-trifluoromethyl-1,3-benzodioxole from Example 2 or 17 were dissolved in 300 ml of carbon tetrachloride, and 0.5 g of anhydrous FeCl$_3$ was added. 32 g of bromine were then added and the mixture was stirred under reflux for 3 hours. After cooling, the mixture was washed with 10% strength NaHSO$_3$ solution, dried with MgSO$_4$ and distilled. The yield was 49 g (63% of theory), and the boiling point was 94°–98° C. under 8 mbar.

Example 26a

5-Chloro-6-formyl-2-(1-chloro-2,2,2-trifluoroethyl)-2-trifluoromethyl-1,3-benzodioxole 67 g of the aldehyde from Example 5 were dissolved in 150 ml of chloroform. Chlorine gas was passed in at 50°–60° C. until all the material had reacted. The crude yield after the solvent had been stripped off was 73 g (98% of theory). The NMR spectra showed the following characteristic absorptions: $^{19}$F-NMR: −68.6 and −81.4 ppm. $^1$H-NMR: 4.81 ppm.

Example 27a

5-Nitro-2-(2,2,2-trifluoroethyl)-2-trifluoromethyl-1,3-benzodioxole

A solution of 54.4 g of 2-(2,2,2-trifluoroethyl)-2-trifluoromethyl-1,3-benzodioxole in 75 ml of methylene chloride was added dropwise to a mixture of 40 ml of 65% strength by weight nitric acid and 40 ml of concentrated sulphuric acid at i0° C. The mixture was subsequently stirred at room temperature for 1 hour and then poured onto ice-water, the organic phase was separated off and the aqueous phase was extracted with methylene chloride. The combined organic phases were washed with water, dried and freed from readily volatile constituents. 95 g of the product (=86% of theory) with a melting point of 87° to 88° C. remained.

The NMR spectra showed the following characteristic absorptions:

$^{19}$F-NMR: −59.0 and −69.4 ppm. $^1$H-NMR: 3.10 ppm.

Example 28a

5-Nitro-2-(1-chloro-2,2,2-trifluoroethyl)-2-trifluoromethyl-1,3-benzodioxole 613 g of 2-(1-chloro-2,2,2-trifluoroethyl)-2-trifluoromethyl-1,3-benzodioxole from Example 2 were dissolved in 1.2 l of methylene chloride and the solution was added dropwise to a mixture of 400 ml of 65% strength nitric acid and 400 ml of concentrated sulphuric acid at 0°–10° C. The mixture was subsequently led at room temperature for 2 hours. It was then poured carefully onto 2 l of ice-water and extracted with methylene chloride. The combined organic phases were washed twice with water, dried and concentrated. The yield was 652 g (93% of theory). The NMR spectra showed the following characteristic absorptions: $^{19}$F-NMR: −66.4 and −79.2 ppm. $^1$H-NMR: 4.81 ppm.

Example 29a 5,6-Dinitro-2-(2,2,2-trifluoroethyl)-2-trifluoromethyl-1,3-benzodioxole 317 g of the product from Example 27 were initially introduced into the reaction vessel and a mixture of 250 ml of 100% strength by weight nitric acid and 350 ml of concentrated sulphuric acid was added dropwise while stirring. The mixture was stirred at 55° C. for 2 hours. It was then allowed to cool and was poured onto ice-water. The product was extracted with methylene chloride, washed neutral with sodium bicarbonate solution, dried and freed from readily volatile constituents on a rotary evaporator. The yield was 339 g (=94% of theory), and the melting point was 101° to 103° C.

The NMR spectra showed the following characteristic absorptions:

$^{19}$F-NMR: −60.9 and −86.5 ppm. $^1$H-NMR: 3.18 ppm.

Example 30a 5,6-Dinitro-2-(1-chloro-2,2,2-trifluoroethyl)-2-trifluoromethyl-1,3-benzodioxole 352 g of 5-nitro-2-(1-chloro-2,2,2-trifluoroethyl)-2-trifluoromethyl-1,3-benzodioxole from Example 28 were initially introduced into the reaction vessel and a mixture of 250 ml of 100% strength by weight nitric acid and 350 ml of concentrated sulphuric acid was added. The mixture was stirred at 60° C. for 2 hours. After cooling, it was poured onto ice-water and extracted with methylene chloride. After washing with sodium bicarbonate solution and drying, the extract was evaporated on a rotary evaporator. The yield was 392 g (91% of theory), and the melting point was 125° C. The NMR spectra showed the following characteristic absorptions: $^{19}$F-NMR: −68.5 and −81.0 ppm. $^1$H-NMR: 4.86 ppm.

Example 31a

5-Chlorosulphonyl-2-(2,2,2-trifluoroethyl)-2-trifluoromethyl-1,3-benzodioxole 136 g of 2-(2,2,2-trifluoroethyl)-2-trifluoromethyl-1,3-benzodioxole were dissolved in 125 ml of chloroform. 175 g of chlorosulphonic acid were added dropwise at 0° C., while stirring, and the mixture was subsequently stirred at room temperature until the evolution of gas had ended. It was then poured onto 750 g of ice-water, the phases were separated and the aqueous phase was extracted with chloroform. The combined organic phases were washed with ice-water and sodium bicarbonate solution, dried with magnesium sulphate and freed from readily volatile constituents on a rotary evaporator. 133 g of product were obtained (=72% of theory), and the melting point was 55° to 57° C. $^{19}$F-NMR: −60.8 and −86.5 ppm. $^1$H-NMR: 3.13 ppm.

Example 32a

5-Cyano-2-(2,2,2-trifluoroethyl)-2-trifluoromethyl-1,3-benzodioxole 35 g of the product from Example 24 were dissolved in 75 ml of dimethylformamide, and 10.5 g of copper(I) cyanide were added. The mixture was stirred at 160° C. for 8 hours. The hot mixture was then poured onto 100 ml of ice-water, and 30 g of 1,2-diaminoethane were added.

After stirring for 30 minutes, the organic phase was separated off and the aqueous phase was extracted with methylene chloride. The combined organic phases were washed with a solution of 30 g of 1,2-diaminoethane in 75 ml of water, dried with magnesium sulphate and distilled under a high vacuum. 20.5 g of the product were obtained (=69% of theory), boiling point 110° C. under 0.02 mbar. $^{19}$F-NMR: −58.1 and −84.6 ppm. $^{1}$H-NMR: 3.08 ppm.

Example 33a

5-Amino-2-(2,2,2-trifluoroethyl)-2-trifluoromethyl-1,3-benzodioxole 57.4 g of the product from Example 27 were dissolved in 400 ml of tetrahydrofuran and hydrogenated with hydrogen in the presence of 4 g of catalyst (palladium-on-charcoal, 10% strength by weight) at 30° C. under 50 bar for 5 hours. Thereafter, the catalyst was filtered off, the solvent was removed and the residue was distilled under a high vacuum. 37 g of product (=63% of theory) with a boiling point of 83° C. under 0.07 mbar were obtained. $^{19}$F-NMR: −59.0 and −84.6 ppm. $^{1}$H-NMR: 2.98 ppm.

Example 34a

4-Amino-2-(1-chloro-2,2,2-trifluoroethyl)-2-trifluoromethyl-1,3-benzodioxole 84 g of 4-nitro-2-(1-chloro-2,2,2-trifluoroethyl)-2 -trifluoromethyl-1,3-benzodioxole from Example 7 were dissolved in 500 ml of tetrahydrofuran and hydrogenated with 15–20 bar of hydrogen over 5 g of palladium-oncharcoal (5% strength) at room temperature for 5 hours. The mixture was then filtered, the filtrate was concentrated and the residue was distilled in vacuo. The yield was 31 g (40% of theory), and the boiling point was 70° C. under 0.1 mbar. The NMR spectra showed the following characteristic absorptions: $^{19}$F-NMR: −68.6 and −81.5 ppm. $^{1}$H-NMR: 4.69 ppm.

Example 35a

5-Amino-2-(1-chloro-2,2,2-trifluoroethyl)-2-trifluoromethyl-1,3-benzodioxole 72 g of 5-nitro-2-(1-chloro-2,2,2-trifluoroethyl)-2 -trifluoromethyl-1,3-benzodioxole from Example 28 were dissolved in 500 ml of tetrahydrofuran and hydrogenated with 15–20 bar of hydrogen over 5 g of palladium-oncharcoal (5% strength) at room temperature for 5 hours. The mixture was then filtered and the solvent was stripped off in vacuo. The yield was 60 g (93% of theory), and the boiling point was 80°–82° C. under 0.1 mbar. The NMR spectra showed the following characteristic absorptions: $^{19}$F-NMR: −66.5 and −79.4 ppm. $^{1}$H-NMR: 4.68 ppm.

Example 36a

5-Isocyanato-2-(2,2,2-trifluoroethyl)-2-trifluoromethyl-1,3-benzodioxole 37 g of the product from Example 33 were dissolved in 50 ml of absolute 1,4-dioxane, and a solution of 13.5 g of diphosgene in 80 ml of absolute 1,4-dioxane was added. The mixture was then stirred at 110° C. (bath temperature) for 6 hours, the solvent was then removed in vacuo and the residue which remained was subjected to fractional distillation in vacuo. 18 g of product (=44% of theory) with a boiling point of 63° C. under 0.1 mbar were obtained. $^{19}$-NMR: −59.3 and −85.0 ppm. $^{1}$H-NMR: 3.0 ppm.

Example 37a 5,6-Diamino-2-(2,2,2-trifluoroethyl)-2-trifluoromethyl-1,3-benzodioxole 339 g of the product from Example 29 were dissolved in 2000 ml of tetrahydrofuran, and 20 g of catalyst (palladium-on-charcoal, 5% strength by weight) were added. The starting substance was hydrogenated with hydrogen at room temperature under 25 to 30 bar for 13 hours. The mixture was then filtered and the solvent was stripped off in vacuo. A solid remained. The yield was 274 g (=96% of theory). $^{19}$F-NMR: −61.2 and −86.6 ppm. $^{1}$H-NMR: 3.02 ppm.

Example 38a 2-(1-Chloro-2,2,2-trifluoroethyl)-2-(trifluoromethyl)-5-hydroxy-1,3-benzodioxole 50 g of 2-(1-chloro-2,2,2-trifluoroethyl)-2-(trifluoromethyl)-5-formyl-1,3-benzodioxole were dissolved 500 ml of methylene chloride, and 53 g of 70% strength by weight m-chloroperbenzoic acid were added. The mixture was stirred under reflux for 6 hours. It was then cooled, and the precipitate which had separated out was filtered off. The filtrate was washed with 5% strength by weight aqueous sodium hydrogen sulphide solution and with saturated aqueous sodiumbicarbonate solution and concentrated on a rotary evaporator. The residue which remained was dissolved in 300 ml of diethyl ether, and 100 ml of 1N sodium hydroxide solution were added at room temperature. When the reaction had ended, the phases were separated and the organic phase was washed with saturated aqueous ammonium chloride solution, dried with magnesium sulphate and subjected to fractional distillation in vacuo. The yield was 26 g (=54% of theory), and the boiling point was 95° C. under 0.07 mbar. $^{19}$F-NMR: −68.6 and −81.6 ppm. $^{1}$H-NMR: 4.70 ppm.

Example 38a 2-(1-Chloro-2,2,2-trifluoroethyl)-2-(trifluoromethyl)-5-hydroxy-1,3-benzodioxole 50 g of 2-(1-chloro-2,2,2-trifluoroethyl)-2-(trifluoromethyl)-5-formyl-1,3-benzodioxole were dissolved 500 ml of methylene chloride, and 53 g of 70% strength by weight m-chloroperbenzoic acid were added. The mixture was stirred under reflux for 6 hours. It was then cooled, and the precipitate which had separated out was filtered off. The filtrate was washed with 5% strength by weight aqueous sodium hydrogen sulphide solution and with saturated aqueous sodiumbicarbonate solution and concentrated on a rotary evaporator. The residue which remained was dissolved in 300 ml of diethyl ether, and 100 ml of 1N sodium hydroxide solution were added at room temperature. When the reaction had ended, the phases were separated and the organic phase was washed with saturated aqueous ammonium chloride solution, dried with magnesium sulphate and subjected to fractional distillation in vacuo. The yield was 26 g (=54% of theory), and the boiling point was 95° C. under 0.07 mbar. $^{19}$F-NMR: −68.6 and −81.6 ppm. $^{1}$H-NMR: 4.70 ppm.

Example 39a

4-Bromomethyl-2-(1-chloro-2,2,2-trifluoroethyl)-2-trifluoromethyl-1,3-benzodioxole 64 g of 4-methyl-2-(1-chloro-2,2,2-trifluoroethyl)-2-trifluoromethyl-1,3-benzodioxole from Example 9 were dissolved in 500 ml of carbon tetrachloride, and 36 g of N-bromosuccinimide and 0.5 g of AIBN (azoisobutyronitrile) were added. The mixture was stirred under reflux for 3 hours and then cooled and filtered. The solvent was stripped off and the residue was distilled in vacuo. The yield was 57 g (71% of theory), and the boiling point was 80°–82° C. under 0.1 mbar. The NMR spectra showed the following characteristic absorptions: $^1$H-NMR: 4.72 ppm.

Example 40a 2-(2,2,2-Trifluoroethyl)-2-trifluoromethyl-1,3-benzodioxole 306.5 g of 2-(1-chloro-2,2,2-trifluoroethyl)-2-trifluoromethyl-1,3-benzodioxole from Example 2 were dissolved in 500 ml of THF, and 101 g of triethylamine and 30 g of palladium-on-charcoal (5% strength by weight) were added. The starting substance was then hydrogenated with 100 bar of hydrogen at 110° C. for 48 h. The mixture was then filtered, the solvent was stripped off and the residue was fractionated in vacuo. The yield was 126 g (46% of theory), and the boiling point was 60° C. under 10 mbar.

The NMR spectra showed the following characteristic absorption: $^{19}$F-NMR: −59.0 and −84.6 ppm. $^1$H-NMR: 3.02 ppm.

o-phenylenediamines containing fluoroalkyl(ene) groups, of the formula

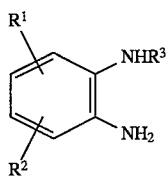

in which
- $R^1$ represents $CF_3$, $OCF_3$, $SCF_3$, $SO_2$-$C_1$-$C_6$-alkyl, which can be straight-chain or branched and completely or partly substituted by fluorine, $N(CF_3)_2$, a phenyl or phenoxyradical with $CF_3$ or CN in the 4-position and optionally further substituents, 1,1,2,3,3,3-hexafluoropropoxy, 1,1,2-trifluoro-2-chloroethoxy, 1,1,2,2-tetrafluoroethoxy, 1,1,2-trifluoro-2-chloroethylthio or 1,1,2,3,3,3-hexafluoropropylthio, independently thereof
- $R^2$ represents F, Cl, Br, CN, $CH_3$, $OCF_3$, $SO_2$—$C_1$-$C_6$-alkyl, which can be straight-chain or branched and completely or partly substituted by fluorine, COO—$C_1$-$C_6$-alkyl, $COOC_6H_5$, 1,1,2,2-tetrafluoroethoxy, 1,1,2,3,3,3-hexafluoropropoxy or 1,1,2-trifluoro-2-chloro-ethoxy and
- $R^3$ represents hydrogen, $COCH_3$ or $COCF_3$, wherein $R^1$ and $R^2$ together can represent an —O—CFCl—CFCl—O— radical, with the exception of the compounds described in EP-A 251 013 and EP-A 487 286, are obtainable by a process in which a benzene derivative of the formula

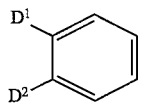

in which
- $D^1$ represents $CF_3O$, $CF_3S$, $CHF_2CF_2O$, CHFCl—$CF_2O$, $CF_3CHFCF_2O$, $CF_3CF_2O$, $CF_3CF_2CF_2O$, $CF_3CF_2S$ or $CF_3CHFCF_2O$ and
- $D^2$ represents $CF_3O$, $CF_3S$, $CHF_2CF_2O$, $CHFCl$-$CF_2O$, $CF_3CHF$-$CF_2O$, $CF_3CF_2O$, $CF_3CF_2CF_2O$, $CF_3CF_2S$, $CF_3CHFCF_2O$, fluorine, chlorine, bromine, $C_1$-$C_6$-alkyl or $C_1$-$C_6$ -alkoxy, is dinitrated and the nitro groups are then reduced to thus give compounds in which $R^1$ and $R^2$ are in the 4- and 5-position relative to the amino groups and have the meaning of $D^1$ and $D^2$.

If compounds in which $R^1$ has the abovementioned meaning and is in the 4-position relative to the amino groups and $R^2$ represents Cl or Br in the 5-position relative to the amino groups are to be prepared, for example, a nitrobenzene derivative of the formula

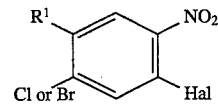

in which
- $R^1$ has the meaning given in the case of formula (I) and Hal represents fluorine, chlorine or bromine, can thus be reacted with ammonia, the Hal group can thus be replaced by an amino group, and the nitroaniline thus obtained can be reduced.

If compounds in which $R^1$ has the abovementioned meaning and is in the 4-position relative to the amino groups, $R^2$ represents chlorine or bromine in the 6-position relative to the amino groups and $R^3$ denotes hydrogen are to be prepared, for example, a nitroaniline of the formula

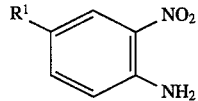

in which
- $R^1$ has the abovementioned meaning, can thus be reacted with a chlorinating or brominating agent, a chlorine or bromine atom can thus be introduced into the meta-position relative to the nitro group, and the nitro group can then be reduced.

If compounds in which $R^1$ represents a donor group in the 4-position relative to the two amino groups, $R^2$ represents an acceptor group, for example COO—$C_1$-$C_6$-alkyl, CN, $CF_3$ or $SO_2$—$C_1$-$C_6$-alkyl and $R^3$ is other than hydrogen are to be prepared, for example a benzene derivative of the formula

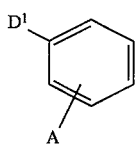

in which
D¹ has the abovementioned meaning and
A represents $CF_3$, $SO_2$—$C_1$-$C_6$-alkyl, which can be straight-chain or branched and completely or partly substituted by fluorine, COO—$C_1$-$C_6$-alkyl or CN, can thus be mononitrated (entry of the $NO_2$ group into the para-position relative to D¹), the $NO_2$ group can be reduced to the $NH_2$ group, the $NH_2$ group can be acylated, for example with acetic acid or trifluoroacetic acid, the product can be mononitrated again (entry of this $NO_2$ group into the ortho-position relative to the NHCOR groups, where R=for example, $CH_3$ or $CF_3$), this $NO_2$ group can be reduced to the $NH_2$ group and, if appropriate, if a compound of the above where $R^3$=hydrogen is to be prepared, the acyl group can be split off by hydrolysis.

The o-phenylenediamines containing fluoroalkyl(ene) groups in which $R^3$ denotes hydrogen can first be reacted with trifluoroacetic acid to give 2-trifluoromethylbenzimidazoles of the formula

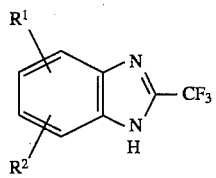

and can then be further reacted with compounds of the formula

wherein $R^1$ and $R^2$ assume the above scope of meaning, $R^4$ represents hydrogen, alkyl or alkoxy, or represents optionally substituted aryl, $R^5$ represents hydroxyl or cyano, or represents in each case optionally substituted alkyl, alkenyl, alkinyl, alkoxy, alkenyloxy, alkinyloxy, alkylthio, amino, aminocarbonyl, alkylcarbonyl, alkoxycarbonyl, alkylcarbonyloxy, dialkoxyphosphonyl, (hetero)aryl, (hetero)arylcarbonyl, (hetero)aryloxycarbonyl, (hetero)arylcarbonyloxy or (hetero)arylaminocarbonylaminocarbonyloxy and A denotes a suitable leaving group.

Leaving groups are known to the expert and are, for example, halogen, alky(alkoxy, aryl)sulphonyloxy, hydroxyl or alkoxy.

Examples

Examples 1 to 6b (dinitration and reduction)

Example 1b 320 g of 1,2-bis-(2-chloro-1,1,2-trifluoroethoxy)-benzene were added dropwise to 500 g of a mixed acid containing 33% by weight of $HNO_3$ and 67% by weight of $H_2SO4$. After one hour at 40° C., 250 ml of 20% strength by weight oleum were added dropwise. The mixture was then heated to 80° C. and subsequently stirred for 15 hours. A further 120 ml of 20% strength by weight oleum and 250 g of the above-mentioned mixed acid were then added dropwise. After 6 hours at 80° to 82° C., the mixture was cooled and poured onto ice. The organic phase was separated off and washed with water. After azeotropic drying with 1,2-dichloroethane, 350 g of 98% by weight pure 1,2-dinitro-4,5-bis-(2-chloro-1,1,2-trifluoroethoxy)-benzene were obtained (oil, $n_D^{20}$: 1.4832, gas chromatography 99.1%).

350 g of this dinitro compound were added dropwise to a mixture of 1.5 l of ethanol, 50 ml of water, 30 ml of concentrated aqueous hydrochloric acid and 470 g of iron filings, and the mixture was heated at the boiling point under reflux for a total of 15 hours. Thereafter, the cooled solution was filtered and concentrated and the residue was recrystalised from cyclohexane. 216 g of 1,2-diamino-4,5-bis-(2-chloro-1,1,2-trifluoroethoxy)-benzene with a melting point of 58° to 60° C. were obtained.

Example 2b

Analogously to Example 1, from 1,2-bis-(1,1,2,3,3,3-hexafluoropropoxy)-benzene, the corresponding 4,5-dinitro compound (oil, $n_D^{20}$: 1.4852) and the corresponding 4,5-diamino compound (oil, 87% by weight pure) was prepared.

Example 3b

Analogously to Example 1, from 1-(1,1,2-trifluoro-2-chloroethoxy)- 2-chlorobenzene, the corresponding 4,5-dinitro compound (melting point 56° to 57° C.) and the corresponding 4,5-diamino compound (melting point 67° to 68° C.) was prepared.

Example 4b

Analogously to Example 1, from 1-trifluoromethoxy-2-bromobenzene, the corresponding 4,5-dinitro compound (melting point 73° to 75° C.) and the corresponding 4,5-diamino compound (oil, 98% by weight pure, $n_D^{20}$: 1.5485) was prepared.

Example 5b

Analogously to Example 1, from 1-trifluoromethoxy-2-chlorobenzene, the corresponding 4,5-dinitro compound (melting point 55° to 56° C.) and the corresponding 4,5-diamino compound (melting point 56°–57° C.) was prepared.

Example 6b

From 1-(1,1,2,3,3,3-hexafluoropropoxy)-2-chloro-benzene, the corresponding 4,5-dinitro compound (oil) and the corresponding 4,5-diamino compound (oil) was prepared.

Examples 7 to 12b

Forcing in ammonia and reduction

Example 7b 260 g of 3-nitro-2,5-dichlorobenzotrifluoride, 130 ml of water and 10 g of tetraethylammonium chloride were initially introduced into an autoclave and 120 ml of liquid ammonia were forced in. The mixture was then heated to 130° C. and stirred at this temperature for 10 hours. After cooling, the mixture was filtered, and the precipitate which had been separated off was washed with water and dried. 194 g of 2-amino-3-nitro-5-chlorobenzotrifluoride with a melting point of 67° C. were obtained.

134 g of the nitroaniline obtained as described above were dissolved in 800 ml of ethanol, and 20 ml of water, 10 ml of concentrated aqueous hydrochloric acid and 160 g of iron filings were then added. The mixture was heated at the boiling point under reflux for 15 hours, subsequently cooled and filtered with suction, the residue on the filter was washed with methylene chloride and the organic phases were then freed from the solvent under reduced pressure. 171 g of 5-chloro-3-trifluoromethyl-1,2-diaminobenzene with a melting point of 53° C. were obtained.

Example 8b

Analogously to Example 7, from 3-nitro-4,6-dichlorodifluorochloromethoxybenzene, first 3-nitro-4-amino-6-chloro-difluorochloromethoxybenzene (melting point 73° C.) and from this 3,4-diamino-6-chloro-difluorochloromethoxybenzene (oil) was obtained.

Example 9b

Analogously to Example 7, from 3-bromo-5-nitro-6-chlorobenzotrifluoride, first 3-bromo-5-nitro-6-amino-benzotrifluoride (melting point 80° to 82° C.) and from this 3-bromo-5,6-diamino-benzotrifluoride (melting point 52° to 54° C.) was prepared.

Example 10b

Analogously to Example 7, from 3-cyano-4-chloro-5-nitrobenzotrifluoride, first 3-cyano-4-amino-5-nitro-benzotrifluoride (melting point 99° to 100° C.) and from this 3-cyano-4,5-diamino-benzotrifluoride was prepared.

Example 11b

Analogously to Example 7, from 3,6-dichloro-5-nitrobenzotrifluoride, first 3-chloro-5-nitro-6-amino-benzotrifluoride (melting point 53° to 54° C.) and from this 3-chloro-5,6-diamino-benzotrifluoride was prepared.

Example 12b

From 2-bromo-4-fluoro-5-nitro-(1,1,2-trifluoro-2-chloro)-ethoxybenzene, first 2-bromo-4-amino-5-nitro-(1,1,2-trifluoro-2-chloro-ethoxy)-benzene (melting point 90° C.) and from this 2-bromo-4,5-diamino-(1,1,2-trifluoro-2-chloro)-ethoxybenzene was prepared.

Example 13b (Halogenation of a nitroaniline and reduction)

24 g of finely powdered 2-nitro-4-trifluoromethylmercapto-aniline were dissolved in 50 ml of trifluoroacetic acid, and 18 g of bromine were metered in at 20° C. The mixture was then subsequently stirred at 20° C. for 3 hours and at 40° C. for a further 30 minutes and poured onto water, and the product was taken up in methylene chloride. After removal of the solvent, 31 g of 6-bromo-2-nitro-4-trifluoromethylmercapto-aniline were obtained.

155 g of the nitroaniline thus prepared were heated at the boiling point under reflux in 700 ml of ethanol with 15 ml of water, 10 ml of concentrated aqueous hydrochloric acid and 70 g of iron filings for 15 hours, the mixture was then filtered, the filtrate was freed from the solvent under reduced pressure and the solid crude product was recrystallised from cyclohexane. 112 g of 6-bromo-4-trifluoromethylmercapto-1,2-diaminobenzene with a melting point of 60° to 61° C. were obtained.

Example 14b 27 g of 2-nitro-4-trifluoromethylsulphonylaniline were brominated with 18 g of bromine in 100 ml of acetic acid analogously to Example 13.

After working up, 32 g of 2-nitro-6-bromo-4-trifluoromethylsulphonyl-aniline were obtained, melting point 147° C.

32 g of the nitroamine thus prepared was reduced with iron filings in alcohol and aqueous hydrochloric acid. 24 g of 3-bromo-5-trifluoromethylsulphonyl-phenylene-1.2-diamine were obtained, melting point 155° to 157° C.

Example 15b 27 g of 2-nitro-4-trifluoromethylsulphonyl-aniline were chlorinated with 10 g of chlorine in 100 ml of acetic acid analogously to Example 14. 29 g of 2-nitro-4-trifluoromethylsulphonyl-6-chloro-aniline were obtained, melting point: 138°–39° C.

13 g of 3-chloro-5-trifluoromethylsulphonyl-1.2-phenylenediamine (melting point: 143°–145° C.) were obtained by reduction.

Example 16 to 20b (Nitration and reduction in 2 stages)

Example 16b 263 g of 4-(2,6-dichloro-4-trifluoromethyl)-phenoxy-acetanilide were dissolved in 1100 ml of methylene chloride and the solution was initially introduced into the reaction vessel at 10° C. 88 g of 98% strength by weight nitric acid were then added dropwise at this temperature. The mixture was subsequently stirred at 10° C. for 1 hour and at 30° C. for a further 2 hours. After addition of 300 ml of water, the phases were separated and the organic phase was freed from the methylene chloride under reduced pressure. 253 g of 2-nitro-4-(2,6-dichloro-4-trifluoromethyl-phenoxy)-acetanilide with a melting point of 138° to 140° C. remained.

91 g of the acetanilide thus prepared were dissolved in 800 ml of dioxane, 10 g of Raney nickel were added and the mixture was hydrogenated under a maximum hydrogen pressure of 50 bar in a hydrogenation apparatus at 25° to 45° C. After the mixture had been let down and filtered, the dioxane was distilled off under a slight vacuum. 65 g of 2-amino-4-(2,6-dichloro-4-trifluoromethyl-phenoxy)-acetanilide with a melting point of 222° to 223° C. remained.

169

Example 17b

Analogously to Example 16, from 3-trifluoromethyl-4-methoxy-acetanilide, first 3-trifluoromethyl-4-methoxy-6-nitro-acetanilide (melting point 143° to 144° C.) and from this 3-trifluoromethyl-4-methoxy-6-amino-acetanilide (melting point 164° to 165° C.) was prepared.

Example 18b

Analogously to Example 16, from 3-trifluoromethyl-4-fluoro-trifluoromethylacetanilide, first 3-trifluoromethyl-4-fluoro-6-nitro-trifluoromethylacetanilide (melting point 78° C.) and from this 3-trifluoromethyl-4-fluoro-6-amino-trifluoromethylacetanilide (melting point 92° to 93° C.) was prepared.

Example 19b

Analogously to Example 16, from 3-trifluoromethyl-4-bromo-trifluoromethylacetanilide, first 3-trifluoromethyl-4-bromo-6-nitro-trifluoromethylacetanilide (melting point 110° to 112° C.) and from this 3-trifluoromethyl-4-bromo-6-amino-trifluoromethylacetanilide (melting point 63° to 65° C.) was prepared.

Example 20b

Analogously to Example 16, from 3-trifluoromethylthio-4-chloro-trifluoromethylacetanilide, first 3-trifluoromethylthio-4-chloro-6-nitro-trifluoromethylacetanilide (melting point 99°–100° C.) and from this 3-trifluoromethylthio-4-chloro-6-amino-trifluoromethylacetanilide (melting point: 88°–90° C.) was prepared.

Example 21b 0.2 mol of 3-bromo-5-trifluoromethyl-phenylene-diamine were heated at the reflux temperature with 150 ml of trifluoroacetic acid for 3 hours. For working up, excess trifluoroacetic acid was distilled off and the residue was partitioned between 100 ml of water and 300 ml of ethyl acetate. The organic phase was separated off, washed successively with in each case 100 ml of aqueous sodium bicarbonate solution and water, dried over sodium sulphate and concentrated in vacuo. The residue was purified by chromatography over silica gel (mobile phase: cyclohexane/ethyl acetate 1:1).

4-Bromo-6-trifluoromethyl-2-trifluoromethyl-1H-benzimidazole of melting point 149°–151° C. was obtained.

Example 22b 0.03 mol of 4-bromo-6-trifluoromethyl-2-trifluoromethyl-1H-benzimidazole and 0.06 mol of powdered potassium carbonate were heated at the reflux temperature in 70 ml of ethyl acetate for 15 minutes, 3.9 g (0.04 mol) of chloromethyl methyl thioether in 20 ml of ethyl acetate were then added, and the mixture was heated at the reflux temperature for a further 4 hours, while stirring. For working up, the cooled reaction mixture was washed twice with in each case 40 ml of water, dried over sodium sulphate and concentrated in vacuo and the residue was purified by chromatography over silica gel (mobile phase: methylene chloride).

1-Methylthiomethyl-4-bromo-6-trifluoromethyl-2-trifluoromethyl-benzimidazole of melting point 56°–60° C. was obtained.

170

We claim:

1. A method of treating parasitic protozoa in an animal or insect, said method comprises administering an effective amount of a compound of the formula

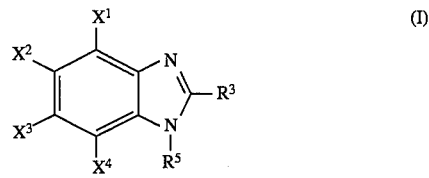

in which $X^1$, $X^2$, $X^3$ and $X^4$ independently of one another in each case represent hydrogen, halogen or cyano, or represent in each case optionally substituted alkyl, alkoxy, alkylthio, alkylsulphinyl, alkylsulphonyl or cycloalkyl, or represent optionally substituted, fused dioxyalkylene, or represent hydroxycarbonyl, alkylcarbonyl, alkoxycarbonyl or cycloalkyloxycarbonyl, or represent in each case optionally substituted amino or aminocarbonyl, or represent in each case optionally substituted aryl, aryloxy, arylthio, arylsulphinyl, arylsulphonyl, arylsulphonyloxy, arylcarbonyl, aryloxycarbonyl, arylazo or arylthiomethylsulphonyl, but wherein am least one of the substituents $X^1$, $X^2$, $X^3$ and $X^4$ is other than hydrogen and halogen, $R^3$ represents fluoroalkyl and $R^5$ represents alkyl which is mono- or polysubstituted by identical or different substituents from the group comprising OH, CN, $NH_2$, cycloalkyl, alkenyl, alkinyl, alkoxy, halogenoalkoxy, alkylthio, halogenoalkylthio, alkenoxy, alkinoxy, aminocarbonyl, optionally substituted alkoxycarbonyl (alkO-CO-), optionally substituted alkoxycarbonyloxy (alkO-COO-), optionally substituted (het-)aryl, optionally substituted (het-)aryloxy, optionally substituted (het-)arylthio, optionally substituted (het-)arylsulphonyl, dialkoxyphosphonyl

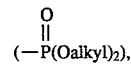

optionally substituted alkylcarbonyl (-CO-alkyl), optionally substituted (het-)arylcarbonyl (-CO-aryl), optionally substituted (het-)aryloxycarbonyl (arylO-CO-), optionally substituted (het-)arylcarbonyloxy (arylCOO-), aminosulphonyl (-$SO_2NH_2$), optionally substituted mono- or dialkylaminosulphonyl, acylated amino or monoalkylamino or optionally substituted dialkylamino, or $R^5$ furthermore represents optionally substituted alkoxycarbonyl, optionally substituted (het-)aryloxycarbonyl, (het-)arylsulphonyl, (het-)arylaminocarbonylaminocarbonyloxy (arylNH-CO-NH-COO-) or -$SO_2$-$NR^1R^2$, wherein $R^1$ and $R^2$ represents H or alkyl which is optionally substituted by one or more of the radicals mentioned above for $R^5$, to an animal or insect in need thereof.

2. The method according to claim 1, wherein the protozoa is coccidia.

3. The method according to claim 1, in which the concentration of active compound is 0.5 to 90 percent by weight.

4. The method according to claim 1, in which the concentration of active compound is 1 to 50 percent by weight.

5. The method according to claim 1, wherein 0.5 to 50 mg of active compound per kg of active compound is employed.

6. The method according to claim 1, wherein 1 to 20 mg of active compound per kg of body weight is employed.

7. The method according to claim 1, in which $X^1$, $X^2$, $X^3$ and $X^4$ independently of one another in each case represent hydrogen, fluorine, chlorine, bromine, iodine, or represent in each case straight-chain or branched alkyl, alkoxy, alkylthio, alkylsulphinyl or alkylsulphonyl having in each case 1 to 8 carbon atoms, or represent in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, or represent divalent dioxyalkylene which has 1 to 5 carbon atoms and is optionally mono- or polysubstituted by identical or different substituents from the group comprising halogen and/or straight-chain or branched alkyl having 1 to 4 carbon atoms and/or straight-chain or branched halogenoalkyl having 1 to 4 carbon atoms and 1 to 9 identical or different halogen atoms but wherein at least one of the substituents $X^1$, $X^2$, $X^3$ and $X^4$ is other than hydrogen and halogen, $R^3$ represents 1–15 fluoro-$C_1$–$C_7$-alkyl, and $R^5$ represents $C_{1-4}$-alkyl which is mono- or polysubstituted by identical or different substituents from the group comprising OH, CN, $NH_2$, $C_5$–$C_{10}$-cycloalkyl, $C_2$–$C_6$-alkenyl, $C_1$–$C_6$-alkinyl, $C_{1-6}$-alkoxy, 1–5 -halogeno-$C_{1-6}$-alkoxy, $C_{1-6}$-alkylthio, 1–5-halogeno-$C_{1-6}$-alkylthio, $C_{2-6}$-alkenoxy, $C_{3-6}$alkinoxy, optionally substituted $C_{1-6}$-alkoxycarbonyl, alkoxycarbonyloxy, aminosulphonyl ($NH_2SO_2$-), monoor di ($C_{1-6}$-alkyl)-aminosulphonyl, acylated amino or acylated mono-($C_{1-6}$-alkyl)amino, phenoxycarbonyl, phenoxycarbonyloxy and di($C_{1-6}$)alkylamino, or $R^5$ furthermore represents the radicals of optionally substituted $C_{1-6}$-alkoxycarbonyl, phenylsulphonyl, optionally substituted phenoxycarbonyl, phenylaminocarbonylaminocarbonyloxy or -$SO_2$-$NR^1R^2$, wherein $R^1$ and $R^2$ represents hydrogen or $C_{1-4}$-alkyl which is optionally substituted by one of the radicals mentioned above for $R^5$.

8. The method according to claim 1, in which $R^3$ represents $C_{1-7}$-alkyl which is halogenated by fluorine, $X^1$ and $X^4$ represent identical or different radicals selected from the group consisting of H, $C_{1-4}$-alkyl which is optionally perhalogenated by fluorine or chlorine, halogen, $C_{1-4}$-alkoxy, amino, acetyl-amino and -$COOR^6$;

$R^6$ represents $C_{1-4}$-alkyl, or cycloalkyl having up to 6 C atoms; and one of the radicals $X^2$ or $X^3$ represents a radical selected from the group consisting of optionally substituted $C_{1-4}$-alkyl, cycloalkyl having up to 6 C atoms, $C_{1-4}$-alkoxy, $C_{1-4}$-alkylthio, $C_{1-4}$-alkylsulphonyl and $C_{1-4}$-alkylsulphonyloxy, and the other radical $X^2$ or $X^3$ represents hydrogen or halogen, or $X^2$ and $X^3$, together with the adjacent C atoms, represent a dioxolanyl or dioxanyl ring which is optionally substituted by halogen, or $C_{1-4}$-halogenoalkyl, or represent optionally substituted phenyl or represent rings of the formulae

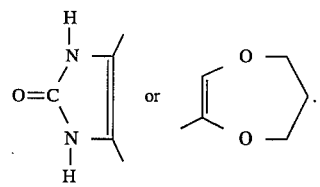

$R^5$ represents methyl or ethyl, which is substituted by OH, CN, $C_{1-4}$-alkoxy, $C_{1-4}$-halogenoalkoxy or $C_{2-4}$-alkoxycarbonyl, or represents aminosulphonyl, mono- or di($C_{1-4}$-alkyl)amino-sulphonyl, mono- or di($C_{1-4}$-halogenoalkyl) amino-sulphonyl, aminocarbonyl, amino or mono-($C_{1-4}$-alkyl)-amino, which can be acylated by $C_{1-4}$-alkoxycarbonyl, acetyl, $C_{2-4}$-alkenylcarbonyl or di($C_{1-4}$-alkyl)amino, or $R^5$ furthermore represents the radical amino-sulphonyl ($NH_2SO_2$-), mono- or di($C_{1-4}$-alkylamino)sulphonyl which are optionally substituted by halogen or carbonyl, or phenylsulphonyl which is optionally substituted by one of the radicals mentioned earlier above.

9. The method according to claim 1, in which $R^3$ represents 1–7-fluoro-$C_{1-4}$-alkyl, $X^1$ and $X^4$ represent hydrogen, halogen, $C_{1-4}$-alkyl, 1–7-halogeno-$C_{1-4}$-alkyl, or $C_{1-4}$-alkoxy, one of the radicals $X^2$ or $X^3$ represents a radical selected from the group consisting of 1–7-halogeno-$C_{1-4}$-alkyl and $C_{1-6}$-alkyl, and the other radical $X^2$ or $X^3$ represents hydrogen or halogen, or the radicals $X^2$ or $X^3$, together with the adjacent C atoms, represent a ring of the following formulae:

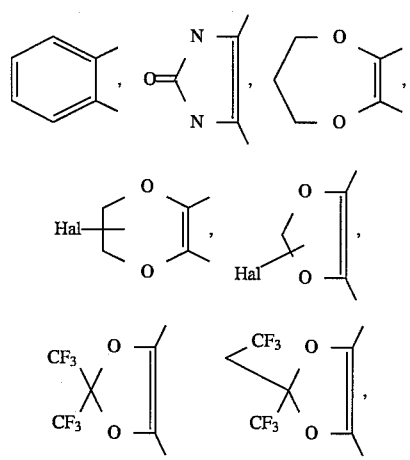

Hal represents fluorine or chlorine and $R^5$ represents the radicals mentioned earlier above.

10. The method according to claim 1, wherein the compound is selected from the group consisting of

| $X^1$ | $X^2$ | $X^3$ | $X^4$ | $R^5$ | $R^3$ |
|---|---|---|---|---|---|
| $CF_3$ | H | Br | H | —CH$_2$Ct.Butyl (C=O) | $CF_3$ |
| Br | H | $CF_3$ | H | —CH$_2$—Ct.Butyl (C=O) | $CF_3$ |
| H | $CF_3$ | Br | H | —CH$_2$—OC$_2$H$_5$ | $CF_3$ |
| H | Br | $CF_3$ | H | —CH$_2$—OC$_2$H$_5$ | $CF_3$ |
| $CF_3$ | H | Br | H | —CH$_2$—CH=CH$_2$ | $CF_3$ |
| $CF_3$ | H | Br | H | —CH$_2$N—CO$_2$C$_2$H$_5$ (i-Propyl) | $CF_3$ |
| $CF_3$ | H | Br | H | —CH$_2$N—CO$_2$C$_2$H$_5$ (C$_5$H$_{11}$) | $CF_3$ |
| H | Cl | $CF_3$ | H | —CH$_2$—O—C$_2$H$_5$ | $CF_3$ |
| H | $CF_3$ | Cl | H | —CH$_2$—O—C$_2$H$_5$ | $CF_3$ |
| $CF_3$ | H | Cl | H | —CH$_2$CN | $CF_3$ |
| $CF_3$ | H | Cl | H | —CH$_2$—OC$_2$H$_5$ | $CF_3$ |
| Br | H | $CF_3$ | H | —CH$_2$N—CO$_2$CH$_3$ (CH$_3$) | $CF_3$ |
| H | —OCF$_3$ | Br | H | —CH$_2$—CN | $CF_3$ and |
| H | Br | —OCF$_3$ | H | —CH$_2$—CN | $CF_3$. |

11. The method according to claim 1, wherein
$X^1$, $X^2$, $X^3$ and $X^4$ each independently is selected from the group consisting of H, Br, CF$_3$ and OCF$_3$,
$R^3$ is CF$_3$, and
$R^5$ is selected from the group consisting of —CH$_2$C(=O)t.Butyl, —CH$_2$—OC$_2$H$_5$, —CH$_2$—CH=CH$_2$, —CH$_2$N—CO$_2$C$_2$H$_5$ (i-Propyl)

—CH$_2$—N—CO$_2$C$_2$H$_5$ (C$_5$H$_{11}$), —CH$_2$CN and

—CH$_2$N—CO$_2$CH$_3$ (CH$_3$).

12. The method according to claim 11, wherein
$X^4$ is H, and
at least one of $X^1$, $X^2$ and $X^3$ also is H.

13. The method according to claim 9, wherein
$X^1$ represents H, Br, or CF$_3$
$X^2$ represents H, Cl, Br, CF$_3$ or -OCF$_3$
$X^3$ represents Cl, Br, CF$_3$ or OCF$_3$,
$X^4$ represents H,
$R^3$ represents CF$_3$, and
$R^5$ represents —C$_2$—C(=O)—t-butyl,

—CH$_2$—OC$_2$H$_5$, —CH$_2$—CH=CH$_2$,

—CH$_2$—N—CO$_2$C$_2$H$_5$ (i-propyl), —CH$_2$N—CO$_2$C$_2$H$_5$ (C$_5$H$_{11}$)

—CH$_2$CN, and —CH$_2$—N—CO$_2$CH$_3$ (CH$_3$).

14. The method according to claim 1, wherein such compound is

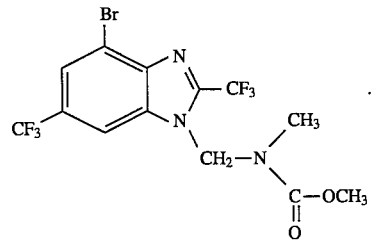

15. The method according to claim 1, wherein such compound is

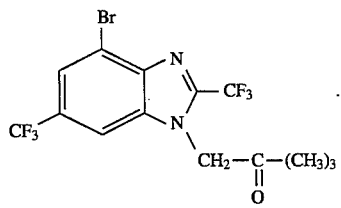

16. The method according to claim 1, wherein such compound is

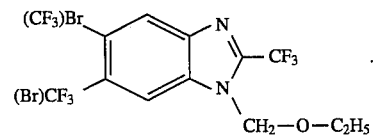

17. The method according to claim 1, wherein such compound is

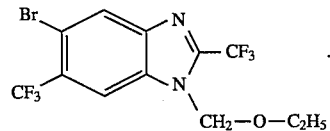

18. The method according to claim 1, wherein such compound is

175
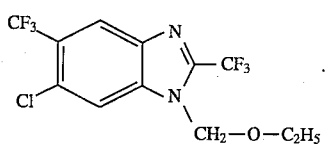
19. The method according to claim 1, wherein such compound is
176
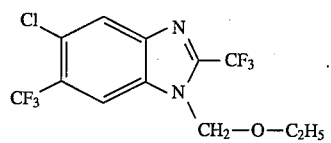
* * * * *

UNITED STATES PATENT AND TRADEMARK OFFICE
CERTIFICATE OF CORRECTION

PATENT NO. : 5,482,956                                    Page 1 of 2
DATED      : January 9, 1996
INVENTOR(S): Lunkenheimer, et al.

It is certified that error appears in the above-indentified patent and that said Letters Patent is hereby corrected as shown below:

Title Page, Item [56]; U.S. PATENT DOCUMENTS:  Insert
                       -- 4,801,598, 1/1989, cooper et al. --

Col. 170, line 28    Delete " am " and substitute -- at --

Col. 174, line 35    Delete " 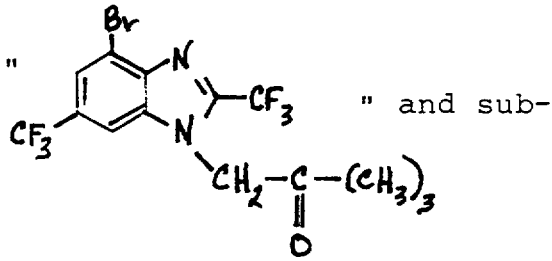 " and sub-

UNITED STATES PATENT AND TRADEMARK OFFICE
CERTIFICATE OF CORRECTION

PATENT NO. : 5,482,956
DATED : January 9, 1996
INVENTOR(S) : Lunkenheimer, et al.

It is certified that error appears in the above-indentified patent and that said Letters Patent is hereby corrected as shown below:

Col. 174, line 35
Cont'd         stitute -- 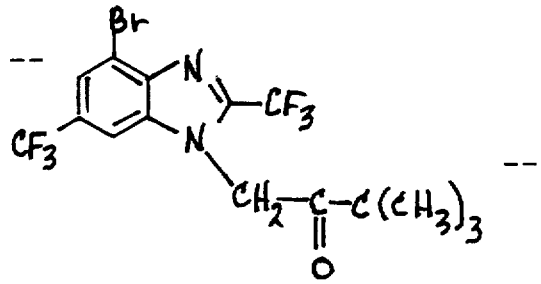 --

Signed and Sealed this

Third Day of September, 1996

Attest:

BRUCE LEHMAN

Attesting Officer      Commissioner of Patents and Trademarks